(12) United States Patent
Dresser et al.

(10) Patent No.: US 12,257,112 B2
(45) Date of Patent: Mar. 25, 2025

(54) CONTACT COUPLED DELIVERY OF RADIATION FOR DENTAL HARD TISSUE TREATMENT

(71) Applicant: Enamel Pure, Worcester, MA (US)

(72) Inventors: Charles Holland Dresser, Wayland, MA (US); Nathan Paul Monty, Shrewsbury, MA (US)

(*) Notice: Subject to any disclaimer, the term of this patent is extended or adjusted under 35 U.S.C. 154(b) by 0 days.

(21) Appl. No.: 18/142,320

(22) Filed: May 2, 2023

(65) Prior Publication Data

US 2023/0277285 A1 Sep. 7, 2023

Related U.S. Application Data

(63) Continuation of application No. 18/092,346, filed on Jan. 2, 2023, now Pat. No. 12,144,695, which is a continuation of application No. 17/876,444, filed on Jul. 28, 2022, now Pat. No. 11,607,297, which is a continuation of application No. PCT/US2021/015567, filed on Jan. 28, 2021.

(60) Provisional application No. 62/969,115, filed on Feb. 2, 2020, provisional application No. 62/968,910, filed
(Continued)

(51) Int. Cl.
| | |
|---|---|
| A61C 17/00 | (2006.01) |
| A61C 1/00 | (2006.01) |
| A61N 5/06 | (2006.01) |
| A61N 5/067 | (2006.01) |
| G02B 5/00 | (2006.01) |
| G02B 19/00 | (2006.01) |

(52) U.S. Cl.
CPC .......... *A61C 17/005* (2013.01); *A61C 1/0046* (2013.01); *A61N 5/0603* (2013.01); *A61N 5/067* (2021.08); *G02B 5/001* (2013.01); *G02B 19/0014* (2013.01); *G02B 19/0047* (2013.01); *A61N 2005/0606* (2013.01)

(58) Field of Classification Search
CPC ...... A61C 17/005; A61C 19/06; A61N 5/067; A61N 5/06; A61N 2005/0606; A61N 2005/067; A61B 18/20
See application file for complete search history.

(56) References Cited

U.S. PATENT DOCUMENTS

| | | | | |
|---|---|---|---|---|
| 4,069,823 A | * | 1/1978 | Isakov ................... | A61B 18/20 D24/170 |
| 4,627,435 A | * | 12/1986 | Hoskin .................. | A61B 18/20 219/233 |

(Continued)

FOREIGN PATENT DOCUMENTS

DE 102004027621 A1 1/2006

OTHER PUBLICATIONS

International Search Report; PCT/US2021/015567; Date: May 28, 2021; By: Authorized Officer Lee Young.

*Primary Examiner* — Nicholas D Lucchesi

(57) ABSTRACT

Embodiments relate to a systems and methods for preventative irradiative dental treatment. In accordance with one embodiment, a system and method include using a radiation source to generate a radiation; using an optic disposed to accept the radiation to internally reflect he radiation at a first end; using at least one side of the optic to contact a dental hard tissue; using the optic to couple some of the radiation into the dental hard tissue; and, using a controller to control a parameter of the radiation to heat a surface of the dental hard tissue.

14 Claims, 34 Drawing Sheets

Related U.S. Application Data on Jan. 31, 2020, provisional application No. 62/968,922, filed on Jan. 31, 2020.

(56) References Cited

U.S. PATENT DOCUMENTS

| | | | | |
|---|---|---|---|---|
| 4,979,180 A | * | 12/1990 | Muncheryan | H01S 3/093 |
| | | | | 372/71 |
| 5,066,294 A | * | 11/1991 | Cosmescu | B23K 26/02 |
| | | | | 356/138 |
| 5,090,908 A | * | 2/1992 | Teumim-Stone | A61C 1/0046 |
| | | | | 606/17 |
| 5,320,620 A | * | 6/1994 | Long | A61B 18/22 |
| | | | | 606/2 |
| 5,898,530 A | * | 4/1999 | Braun | F21V 31/03 |
| | | | | 362/318 |
| 5,908,416 A | * | 6/1999 | Costello | A61B 5/1411 |
| | | | | 606/17 |
| 2007/0100330 A1 | | 5/2007 | Tilleman et al. | |
| 2007/0244527 A1 | | 10/2007 | Hatayma et al. | |
| 2010/0160906 A1 | * | 6/2010 | Jarrard | A61B 18/1492 |
| | | | | 606/41 |
| 2012/0035540 A1 | * | 2/2012 | Ferren | A61B 5/076 |
| | | | | 604/95.01 |
| 2012/0296325 A1 | * | 11/2012 | Takashino | A61B 18/1442 |
| | | | | 606/41 |
| 2014/0065570 A1 | * | 3/2014 | Chen | A61N 5/0603 |
| | | | | 433/29 |
| 2014/0363784 A1 | | 12/2014 | Monty et al. | |
| 2016/0015489 A1 | * | 1/2016 | Atiya | G02B 5/3083 |
| | | | | 433/29 |
| 2018/0325622 A1 | | 11/2018 | Groves, Jr. et al. | |
| 2019/0124888 A1 | * | 5/2019 | Coyle | A61N 5/0603 |
| 2021/0138261 A1 | * | 5/2021 | Bhawalkar | A61M 35/003 |
| 2021/0193295 A1 | * | 6/2021 | Bhawalkar | A61N 5/0613 |

* cited by examiner

CONTACT COUPLED DELIVERY OF RADIATION FOR DENTAL HARD TISSUE TREATMENT

CROSS REFERENCE TO RELATED APPLICATIONS

This application claims benefit of priority to U.S. Non-Provisional application Ser. No. 18/092,346, filed on Jan. 2, 2023 and entitled "PREVENATIVE DENTAL HARD TISSUE LASER TREATMENT SYSTEMS AND METHODS," which, in turn, claims the priority of U.S. Non-Provisional application Ser. No. 17/876,444, filed on Jul. 28, 2022 and entitled "PREVENTATIVE DENTAL HARD TISSUE LASER TREATMENT SYSTEMS AND METHODS," the entirety of both of which is incorporated herein by reference. U.S. Non-Provisional application Ser. No. 17/876,444 claims the benefit of priority to PCT App. No. PCT/US21/15567, filed on Jan. 28, 2021 and entitled "PREVENATIVE DENTAL HARD TISSUE LASER TREATMENT SYSTEMS, METHODS, AND COMPUTER-READABLE MEDIA," the entirety of which is incorporated herein by reference. PCT App. No. PCT/US21/15567 in turn claims priority benefit to U.S. Prov. App. No. 62/969,115, filed on Feb. 2, 2020 and entitled "SYSTEMS AND METHODS FOR DISTRIBUTION OF SINGLE USE PREVENTATIVE DENTAL HARD TISSUE TREATMENTS," U.S. Prov. App. No. 62/968,910, filed on Jan. 31, 2020 and entitled "LASER DELIVERY OF TRANSVERSE ELECTROMAGNETYIC MODES FOR EVEN PREVENTATIVE DENTAL HARD TISSUE TREATMENT," U.S. Prov. App. No. 62/968,922, filed on Jan. 31, 2020 and entitled "CONTACT COUPLED DELIVERY OF RADIATION FOR DENTAL HARD TISSUE TREATMENT," all of which are incorporated herein in their entirety by reference.

TECHNICAL FIELD

This invention generally relates to systems and methods for preventative dental laser treatment and, more particularly but not exclusively, to systems and methods for delivery of laser beams with certain transverse electromagnetic modes during dental treatment.

BACKGROUND

Research has long showed the ability of some lasers to make dental hard tissue (e.g., enamel) less susceptible to acidic dissolution. For example, in 1998, J. Featherstone et al. demonstrated inhibition of caries progression ranging from 40% to 85% after irradiation with infrared laser sources in an article entitled "$CO_2$ Laser Inhibitor of Artificial Caries-Like Lesion Progression in Dental Enamel," incorporated herein by reference, published in the Journal of Dental Research. These results have been corroborated and repeated throughout the years. Another notable project involved researchers for University of California San Francisco and Indiana University both evaluating laser treatment for caries-inhibition in different intra-oral models. The project was documented in an article entitled "Effect of Carbon Dioxide Laser Treatment on Lesion Progression in an Intraoral Model," published in 2001 in Proc. SPIE by J. Featherstone et al. and incorporated herein by reference.

A mechanism that is believed to contribute to this inhibition of acid dissolution in laser treated hard tissue is carbonate removal. Human dental enamel is primarily (96%) comprised of hydroxyapatite (HA). Specifically, the HA found in dental enamel is non-stoichiometric carbonate-substituted hydroxyapatite $(Ca_{10}(PO_4)_{6-x}(OH)_{2-y})(CO_3)_{x+y}$, where $0 \leq x \leq 6$, $0 \leq y \leq 2$, which contains trace amounts of fluoride (F), sodium (Na), magnesium (Mg), zinc (Zn) and strontium (Sr)), as reported by C. Xu et al., in an article published in 2014 in J. Material Sci., entitled "The Distribution of Carbonate in Enamel and its Correlation with Structure and Mechanical Properties," incorporated herein by reference. Xu et al. describe that increases in carbonate content within enamel correlate with decreases in mechanical properties, for example crystallinity, modulus, and hardness. It has also been long reported that increased carbonate content within enamel correlates with an increased susceptibility to acid. For example, J. Featherstone et al. reported in "Mechanism of Laser-Induced Solubility Reduction of Dental Enamel," first published in SPIE Proc. in 1997, incorporated herein by reference, that carbonate removal from enamel correlates to increased resistance to caries, with complete carbonate removal correlating with the optimum resistance to caries. Caries are formed by acid dissolution or demineralization. Removal of carbonate within dental enamel is achieved through elevating a temperature of the enamel.

The temperature range required for removing carbonate from dental tissue has long been taught, for example by Zuerlein et al. in an article, published in 1999 in Lasers in Surgery and Medicine, entitled "Modeling the Modification Depth of Carbon Dioxide Laser-Treated Dental Enamel" and incorporated herein by reference. Zuerlein et al. found that carbonate loss began when enamel reached temperatures in excess of 400° C. during laser irradiation, but complete carbonate removal was not achieved until the enamel reached its melting point. The melting point of dental enamel is about 1280° C. as reported by Fried et al. in an article, published in 1998 in Applied Surface Science, entitled "IR Laser Ablation of Dental Enamel: Mechanistic Dependence on the Primary Absorber," incorporated herein by reference.

For over 20 years it has been known to the dental research community that momentarily elevating a temperature of dental enamel to temperature in a range between 400° C. and 1300° C. will reduce carbonate content and increase the enamel's resistance to acid (e.g., caries and erosion). However, the difficulties associated with momentarily raising a patient's tooth surface to a temperature more consistent with that of liquid magma (e.g., lava) than human tissue, presents a number of problems, which have yet to be satisfied in a commercial product.

SUMMARY

While the results of the scientific research have shown great promise for over 20 years, careful scrutiny of the literature will reveal, in most cases (with a few notable exceptions), that after undergoing laser irradiation, dental hard tissue surfaces are often damaged by the laser. Commonly, much of the surface of the dental hard tissue will melt, crack, or partially ablate as a result of overheating during treatment, or sections of the enamel are unknowingly left untreated due to the treatment parameters variability. This typically does not negatively affect most acid dissolution (e.g., caries inhibition) measurements, but it nevertheless remains an undesirable result of treatment.

As mentioned above, some references in the literature have taken special care not to cause melting or cracking of dental hard tissue during preventative laser treatment. These references are pointed out below. M. Esteves-Oliveira et al.

describe achieving caries resistant effects without thermal damage in "$CO_2$ Laser (10.6 µm) Parameters for Caries Prevention in Dental Enamel," published in Caries Research and incorporated herein by reference. J. W. Kim et al. also demonstrated that lower fluences can cause acid resistance in teeth without also melting or cracking in "Influence of a Pulsed $CO_2$ Laser Operating at 9.4 µm on the Surface Morphology, Reflectivity, and Acid Resistance of Dental Enamel Below the Threshold for Melting," published in the Journal of Biomedical Optics in 2017 and incorporated herein by reference. Both, J. W. Kim et al. and M. Esteves-Oliveira et al. demonstrate that it is possible in vitro to induce acid dissolution resistance in an enamel surface without also melting the enamel using a $CO_2$ laser with a Gaussian energy profile, however additional problems are presented by attempts to commercialize the technology. For example, how to ensure that the enamel is never overheated in tens of thousands of treatments?

Some recent steps have been made toward addressing these problems for potential commercialization. For example, U.S. patent application Ser. No. 15/976,272 by Groves et al., incorporated herein by reference, describe a laser system for preventative dental hard tissue treatment. Specifically, Groves et al. describes controlling a $CO_2$ laser beam pulse energy in order to deliver a controlled amount of energy (e.g., not too much energy), to prevent surface modifications (defined within the application to mean cracking or melting) while still achieving a therapeutic effect. In order to achieve this Groves et al. describe a number of power and energy feedback systems that measure pulsed laser energy interpulse and intrapulse. Real-time (e.g., less than 500 nS) measurement of infrared (e.g., wavelength of 8 µm or greater) laser energy requires use of specialized photodiodes (e.g., Mercury Cadmium Telluride [HgCdTe] sensors). Additionally, these photodiodes only provide a relative intrapulse measurement of laser power. Therefore, the systems must be calibrated by the user (e.g., before every treatment), typically with a thermopile to measure absolute average power of the laser beam. Thermopiles are notoriously inaccurate and typically provide a measurement that is within a range of +/−5% of actual laser power. Additionally, $CO_2$ lasers drift in power output during normal operation, in a range of about +/−10%. With so many sources of uncertainty, precise control of pulse energy is imperfect in a commercially realizable device. It is for this reason that systems like those described by Groves et al. must reduce the peak irradiance (or fluence) delivered to the dental hard tissue and produce non-optimal heating of dental tissue in order to ensure that overheating does not occur. Exemplary non-optimal results are shown by Groves et al. in FIGS. 7C and 7D, which indicate incomplete carbonate removal of the treated surface.

Additionally, unlike many of the tools presently used in dental operatories, Groves et al. describe a system that must use a non-contacting dental laser hand piece. The hand piece must be used by a dental clinician to aim a laser beam at every tooth surface undergoing treatment. This places a large burden on the dental clinician to accurately aim the laser, treat the enamel surfaces (without missing a spot), avoid hitting unintended oral surfaces with the laser, and do all of this quickly (with as little "patient chair time" as possible). A system as taught by Groves et al., if realizable in a commercial product, would require substantial amounts of training on the part of the dental clinician prior to proficient use of the system.

While the results of the scientific research have shown great promise for over 20 years, commercialization and adoption of this technology has not occurred anywhere in the world. A commercial impediment to the adoption of this groundbreaking technology is the relatively high cost of mid-infrared (e.g., wavelength between 9 and 11 µm) laser sources and other high-tech components (e.g., optical components, beam scanning systems, and articulated arms) required to perform the laser treatment. For example, at the time of writing the Solea dental laser system (from Convergent Dental of Needham, Massachusetts, U.S.A.) which is not FDA cleared for preventative dental laser treatment, but which does comprise a mid-infrared laser source costs over $120,000. This high price point is commonplace for medical and dental systems that employ laser sources and typically prices adoption of these systems out of reach of medical and dental practitioners that do not place a high premium on using the latest technology.

Systems and methods for preventative dental laser treatment have been known to science for decades. However, the known state-of-the-art (including all of the above mentioned references) fail to (i) produce a laser beam that optimally heats the enamel, without generating central areas of peak temperature that are prone to overheating; (ii) a system that may be used in contact with the laser tissue, like tools already known to dental hygienists and dentists; or, (iii) teach a way for the required high tech (and high cost) technology to be implemented in ordinary dental operatories and thereby be made accessible to all dental patients, without great upfront investment being required by individual dental practitioners. In order for dental patients to benefit from decades of scientific breakthroughs in preventative dental laser treatments, laser systems and methods must be developed that (i) reliably introduce even heating of the dental hard, while simultaneously preventing overheating; (ii) are easily adopted and quickly and safely used by dental clinicians; and, (iii) can be made available with a cost structure, which the dental market can comfortably bear.

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

In one aspect, embodiments relate to a system for preventative dental laser treatment that ensures even irradiation of a laser beam. The system includes, a laser arrangement configured to generate the laser beam. The laser beam has at least one of a super-Gaussian energy profile and a transverse ring mode. The system also includes a focus optic. The focus optic is configured to converge the laser beam with a numerical aperture of 0.1 or less to a focal region. The system also includes a hand piece configured to direct the laser beam at a surface of a dental hard tissue. The system additionally includes a controller. The controller is configured to control at least one parameter of the laser source, such that a portion of the surface of the dental hard tissue is heated to a temperature in a range between 40° and 1300° Centigrade.

In some embodiments of the system, the system also includes a turning mirror positioned down beam from the focus optic. The turning mirror is configured to reflect the laser beam toward the dental hard tissue.

In some embodiments of the system, the laser arrangement includes a beam shaper. The beam shaper is configured to shape the laser beam into the at least one of the super-Gaussian energy profile and the transverse ring mode. In some versions, the beam shaper includes at least one of an axicon, a spatial filter, a deformable mirror, and an annular slit.

In some embodiments of the system, the laser beam has a wavelength in at least one of a first range of 200 to 500 nm and a second range of 4,000 to 11,000 nm.

In some embodiments of the system, the laser arrangement also includes at least one of an intra-cavity polarization generator and a polarization converter. In some cases, the laser beam has a polarization that comprises at least one of circular, radial, tangential, and azimuthal.

In some embodiments of the system, the at least one laser parameter of the laser beam controlled by the controller includes at least one of: repetition rate, pulse energy, pulse duration, average power, peak power, and wavelength.

In some embodiments of the system, the system additionally includes a beam scanning system. The beam scanning system is configured to scan the focal region over a portion of the surface of the dental hard tissue.

In some embodiments of the system, the transverse ring mode has an inner diameter that is 50% less than its outer diameter.

In some embodiments of the system, the transverse ring mode is a transverse electromagnetic mode (TEM) 01*.

In some embodiments of the system, the focus optic has a focal length that is greater than 100 mm.

In some embodiments of the system, the laser arrangement includes a laser source having an intra-cavity device configured to generate the at least one of the super-Gaussian energy profile and the transverse ring mode.

In some embodiments of the system, the laser arrangement includes a laser source having an intra-cavity device configured to control a power of the laser beam.

In another aspect, embodiments relate to a method for preventative dental laser treatment that ensures even irradiation of a laser beam. The method includes generating, using a laser arrangement, a laser beam having at least one of a super-Gaussian energy profile and a transverse ring mode; converging, using a focus optic, the laser beam with a numerical aperture no greater than 0.1 to a focal region; directing, using a hand piece, the laser beam at a surface of a dental hard tissue; and, controlling, using a controller, at least one parameter of the laser beam, such that a portion of the surface of the dental hard tissue is heated to a temperature in a range of 400 to 1300° C.

In some embodiments of the method, the method also includes reflecting, using a turning mirror, the laser beam toward the dental hard tissue. The turning mirror is located down beam from the focus optic.

In some embodiments of the method, generating the laser beam having the at least one of the super-Gaussian and the transverse ring mode includes shaping, using a beam shaper, the laser beam. In some versions, the beam shaper includes one or more of an axicon, a spatial filter, a deformable mirror, and an annular slit.

In some embodiments of the method, the laser beam has a wavelength in at least one of a first range of 200 to 500 nm and a second range of 4,000 to 11,000 nm.

In some embodiments of the method, the laser arrangement also includes at least one of an intra-cavity polarization generator and a polarization converter. In some cases, the laser beam has a polarization that comprises at least one of circular, radial, tangential, and azimuthal.

In some embodiments of the method, the at least one parameter controlled by the controller is at least one of: repetition rate, pulse energy, pulse duration, average power, peak power, and wavelength.

In some embodiments of the method, the method also includes scanning, using a beam scanning system, the focal region over a portion of the surface of the dental hard tissue.

In some embodiments of the method, the transverse ring mode has an inner diameter that is 50% less than its outer diameter.

In some embodiments of the method, the transverse ring mode is a transverse electromagnetic mode (TEM) 01*.

In some embodiments of the method, the focus optic has a focal length that is greater than 100 mm.

In some embodiments of the method, the laser arrangement includes a laser source having an intra-cavity device configured to generate the transverse ring mode.

In some embodiments of the method, the laser arrangement includes a laser source having an intra-cavity device configured to control a power of the laser beam.

In one aspect, embodiments relate to a system for preventative irradiative dental treatment. The system includes, a radiation source configured to generate a radiation. The radiation has a wavelength within one of two ranges, a first range of 100-500 nm and a second range of 8,000-12,000 nm. The system also includes an optic disposed to accept the radiation at a first end, internally reflect the radiation, and contact a dental hard tissue with at least one side of the optic. The optic is additionally configured to couple at least a portion of the radiation into the dental hard tissue when placed in contact with the dental hard tissue on the at least one side. The system also includes a controller configured to control at least one parameter of the radiation to heat a surface of the dental hard tissue to a temperature of at least 400° Celsius.

In some embodiments of the system, the optic comprises one or more of a waveguide, a rod, and a prism.

In some embodiments of the system, the optic has an index of refraction that is no greater than an index of refraction of the dental hard tissue and no less than an index of refraction of a dental soft tissue.

In some embodiments of the system, the optic is configured to couple at least a portion of the radiation into the dental hard tissue using at least one of attenuated total internal reflection (ATIR), frustrated total internal reflection (FTIR), and an evanescent wave.

In some embodiments of the system, the optic is additionally configured to couple substantially no portion of the radiation into a dental soft tissue when placed in contact with the dental soft tissue on the at least one side.

In some embodiments of the system, the optic is further configured to be placed in contact with an inter-proximal surface of the dental hard tissue.

In some embodiments of the system, the optic includes at least one of quartz, zinc sulfide, barium fluoride, magnesium fluoride, calcium fluoride, zinc selenide, and diamond.

In some embodiments of the system, the system additionally includes a detector configured to detect at least one characteristic of the radiation as it exits a second end of the optic.

In some embodiments of the system, the system additionally includes a cooling system configured to cool the optic.

In some embodiments of the system, the system additionally includes a homogenizer disposed between the radiation source and the optic to homogenize the radiation.

In another aspect, embodiments relate to a method for preventative irradiative dental treatment. The method includes generating, using a radiation source, a radiation having a wavelength within one of two ranges, a first range between 100 and 500 nm and a second range between 8,000 and 12,000 nm; internally reflecting the radiation within an optic disposed to accept the radiation at a first end; contacting a dental hard tissue with at least one side of the optic; coupling, using the optic, at least a portion of the radiation into the dental hard tissue; and, controlling, using a controller at least one parameter of the radiation to heat a surface of the dental hard tissue to a temperature of at least 400° Celsius.

In some embodiments of the method, the optic comprises one or more of a waveguide, a rod, and a prism.

In some embodiments of the method, the optic has an index of refraction that is no greater than an index of refraction of the dental hard tissue and no less than an index of refraction of a dental soft tissue.

In some embodiments of the method, coupling, using the optic, at least a portion of the radiation into the dental hard tissue includes at least one of attenuated total internal reflection (ATIR), frustrated total internal reflection (FTIR), and an evanescent wave.

In some embodiments of the method, the method additionally includes contacting a dental soft tissue with the at least one side of the optic; and, coupling, using the optic, substantially no portion of the radiation into the dental soft tissue.

In some embodiments of the method, the method additionally includes contacting, using the optic, an inter-proximal surface of the dental hard tissue.

In some embodiments of the method, the optic includes at least one of quartz, zinc sulfide, zinc selenide, barium fluoride, magnesium fluoride, calcium fluoride, sapphire, and diamond.

In some embodiments of the method, the method also includes detecting, using a detector, at least one characteristic of the radiation as it exits a second end of the optic.

In some embodiments of the method, the method also includes cooling the optic, using a cooling system.

In some embodiments of the method, the method also includes homogenizing the radiation, using a homogenizer.

As disclosed above, much research has been done on the use of a laser for affecting an increase in acid resistance in dental hard tissue. However, acquiring a laser system typically requires dental practices to pay an expensive upfront cost ($50,000 or more). The high upfront cost of the laser system is expected to slow the adoption of this potentially paradigm shifting technology. Furthermore, it is expected that because of this high upfront cost dental practices treating patients most likely to benefit from the treatment (e.g., patients from communities having worse dental hygiene), in some cases, will be last to gain access to this laser technology. In order to speed adoption of this remarkable technology and combat this access problem new systems and methods for preventative laser treatment distribution are disclosed.

In accordance with one embodiment, an upfront cost of a dental laser system is partially defrayed after installation of the laser system by small recurring costs. For example, in some versions a dental laser system is provided at a reduced cost to a dental practice (minimizing upfront costs) and the dental practice pays small recurring payments to use the dental laser system. In some cases, the recurring payments are made on a subscription basis (e.g., per day, per week, per month, or per year). Alternatively, the recurring payments are made per treatment (or per a certain number of treatments).

Commercially, a reduction in price of a high-tech laser system cannot be warranted unless recurrent sales are virtually guaranteed to the dental laser system manufacturer. Unfortunately, unauthorized use is possible either by unknowing clinicians who fall victim to counterfeiters, or by fraudulent users. Unauthorized use of the laser system (without recurrent payment), therefore poses a threat to the recurrent payment distribution method and therefore to the widespread adoption of preventative dental laser treatment. At least for these reasons, embodiments of systems and methods are presented herein that aim to prevent and expose unauthorized use of a preventative dental laser system.

In one aspect, embodiments relate to a method for preventative dental laser treatment. The method includes a reading a machine-readable code; verifying, using a processor, the machine-readable code; performing a laser treatment, based upon the verified machine-readable code; applying a dental fluoride treatment dose; and, preventing, using the processor, future verification of the machine-readable code. Performing the laser treatment includes generating, using a laser arrangement, a laser beam; directing, using an optical arrangement, the laser beam toward a dental hard tissue; and, controlling, using a laser controller, a parameter of the laser beam in order to heat at least a portion of a surface of the dental hard tissue to a temperature above 400° Celsius.

In some embodiments of the method, the dental fluoride dose comprises one or more of Sodium Fluoride, Stannous Fluoride, Titanium Tetrafluoride, Acidulated-Phosphate Fluoride, and Amine Fluoride.

In some embodiments of the method, the dental fluoride dose comprises one or more of a gel, a varnish, a paste, and a foam.

In some embodiments of the method, the machine-readable code comprises one or more of a barcode, a two-dimensional (2D) barcode, a data matrix, a digital signature, a cryptocurrency, a magnetic strip, a transponder device, a microchip, and a radio-frequency identification (RFID) tag.

In some embodiments of the method, verifying the machine-readable code includes one or more of querying a ledger; broadcasting to a ledger; decrypting the machine-readable code; recognizing a digest within the machine-readable code; querying a write once read many (WORM) memory; and, querying a coupon authority.

In some embodiments of the method, preventing future verification of the machine-readable code includes one or more of broadcasting to a ledger; submitting to a coupon authority; destroying the machine-readable code; writing to a write once read many (WORM) memory; and, overwriting the machine-readable code.

In some embodiments of the method, the method also includes measuring a laser variable during the laser treatment. In some cases, the laser variable includes one or more of a duration of laser treatment, an electrical energy delivered to the laser source during the laser treatment, and a relative measure of laser energy generated by the laser source during laser treatment.

In some embodiments of the method, the method also includes attaching a consumable laser attachment to a hand piece prior to the laser treatment. In some cases, the consumable laser attachment comprises the machine-readable code.

In one aspect, embodiments relate to a system for preventative laser treatment. The system includes a code reader, a processor, and a laser treatment system. The code reader is configured to read a machine-readable code. The processor is configured to verify the machine-readable code and prevent future verification of the machine-readable code. The laser treatment system includes a laser arrangement configured to generate a laser beam, an optical arrangement configured to direct the laser beam toward a dental hard tissue, and a laser controller configured to control a parameter of the laser beam in order to heat at least a portion of a surface of the dental hard tissue to a temperature above 400° Celsius.

In some embodiments of the system, the optical arrangement includes one or more of a beam delivery system, a hand piece, and a beam scanning system.

In some embodiments of the system, the optical arrangement includes a hand piece configured to attach to a consumable laser attachment. In some cases, the consumable laser attachment includes the machine-readable code.

In some embodiments of the system, the machine-readable code includes one or more of a barcode, a two-dimensional (2D) barcode, a data matrix, a digital signature, a cryptocurrency, a magnetic strip, a transponder device, a microchip, and a radio-frequency identification (RFID) tag.

In some embodiments of the system, the processor is configured to verify the machine-readable code by performing one or more of querying a ledger; broadcasting to a ledger; decrypting the machine-readable code; recognizing a digest within the machine-readable code; querying a write once read many (WORM) memory; and, querying a coupon authority.

In some embodiments of the system, the processor is configured to prevent future verification of the machine-readable code by performing one or more of broadcasting to a ledger; submitting to a coupon authority; destroying the machine-readable code; writing to a write once read many (WORM) memory; and, overwriting the machine-readable code.

In some embodiments of the system, the system includes a meter configured to measure a laser variable during treatment. In some cases, the laser variable includes one or more of a duration of laser treatment, an electrical energy delivered to the laser source during laser treatment, and a relative measure of laser energy generated by the laser source during laser treatment.

In one aspect, embodiments relate to a distribution system for preventative dental laser treatment. The distribution system includes a hermetically sealed package, a single use dental fluoride treatment dose located within the package, and a machine-readable code collocated with the package. The machine-readable code is substantially inaccessible so long as the package remains intact. The machine-readable code, once verified, is configured to allow use of a laser-based treatment system.

In some embodiments of the distribution system, the dental fluoride treatment dose includes one or more of Sodium Fluoride, Stannous Fluoride, Titanium Fluoride, Acidulated-Phosphate Fluoride, and Amine Fluoride.

In some embodiments of the distribution system, the dental fluoride treatment dose includes one or more of a gel, a varnish, a paste, and a foam.

In some embodiments of the distribution system, the machine-readable code includes one or more of a barcode, a two-dimensional (2D) barcode, a data matrix, a digital signature, a cryptocurrency, a magnetic strip, a transponder device, a microchip, and a radio-frequency identification (RFID) tag.

In some embodiments of the distribution system, the machine-readable code includes one or more of a digital signature, a private key, a public key, and a unique identifier; and the machine-readable code is associated with data accessible to the dental laser system.

In some embodiments of the distribution system, the distribution system includes a consumable laser attachment. The consumable laser attachment is configured to attach to a hand piece. The consumable laser attachment includes the machine-readable code. In some cases, the consumable laser attachment includes one or more of an authentication chip, a one-wire chip, and a radio-frequency identification (RFID) tag. In some cases, the consumable laser attachment is configured to be used intra-orally. In some cases, the consumable laser attachment is configured to direct a laser beam.

In some embodiments of the distribution system, the distribution system also includes a fluoride applicator. The fluoride applicator includes one or more of a tray, a brush, a swab, a needle, a syringe, and a cloth.

In another aspect, some embodiments relate to one or more non-transitory computer-readable media storing instructions that are executable by a processing device. The execution of the instructions cause the processing device to read a machine-readable code; verify the machine-readable code; perform a laser treatment, based upon the machine-readable code; and, prevent future verification of the machine-readable code. In some cases, the laser treatment includes generating, using a laser arrangement, a laser beam; directing, using a laser arrangement, the laser beam toward a dental hard tissue; and, controlling, using a laser controller, a parameter of the laser beam in order to heat at least a portion of a surface of the dental hard tissue to a temperature of at least 400° Celsius.

In another aspect, some embodiments relate to another distribution system for preventative dental laser treatment. The distribution system includes a hermetically sealed package, a machine-readable code collocated with the package, and a consumable laser attachment configured to attach to a hand piece located within the hermetically sealed package. The machine-readable code is substantially inaccessible so long as the package remains intact. The code, once verified, is configured to allow use of a laser-based treatment system. In some cases, the consumable laser attachment comprises the machine-readable code.

In some embodiments of the distribution system, the dental fluoride treatment dose includes one or more of Sodium Fluoride, Stannous Fluoride, Titanium Fluoride, Acidulated-Phosphate Fluoride, and Amine Fluoride.

In some embodiments of the distribution system, the dental fluoride treatment dose includes one or more of a gel, a varnish, a paste, and a foam.

In some embodiments of the distribution system, the machine-readable code includes one or more of a barcode, a two-dimensional (2D) barcode, a data matrix, a two-dimensional (2D) barcode, a data matrix, a digital signature, a cryptocurrency, a magnetic strip, a transponder device, a microchip, and a radio-frequency identification (RFID) tag.

In some embodiments of the distribution system, the machine-readable code includes one or more of a digital signature, a private key, a public key, and a unique identifier; and the machine-readable code is associated with data accessible to the dental laser system.

In some embodiments of the distribution system, the consumable laser attachment includes the machine-readable code. In some cases, the consumable laser attachment is configured to be used intra-orally. In some cases, the consumable laser attachment is configured to direct a laser beam.

In some embodiments of the distribution system, the distribution system also includes a fluoride applicator. The fluoride applicator includes one or more of a tray, a brush, a swab, a needle, a syringe, and a cloth.

In another aspect, some embodiments relate to another method for preventative dental treatment. The method includes reading a machine-readable code; verifying, using a processor, the machine-readable code; performing a laser treatment, based upon the machine-readable code; and, preventing, using the processor, future verification of the machine-readable code. The laser treatment includes generating, using a laser arrangement, a laser beam; directing, using an optical arrangement, the laser beam toward a dental hard tissue; and controlling, using a laser controller, at least one parameter of the laser beam in order to heat at least a portion of a surface of the dental hard tissue to a temperature no less than 400° Celsius.

Any combination and permutation of embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
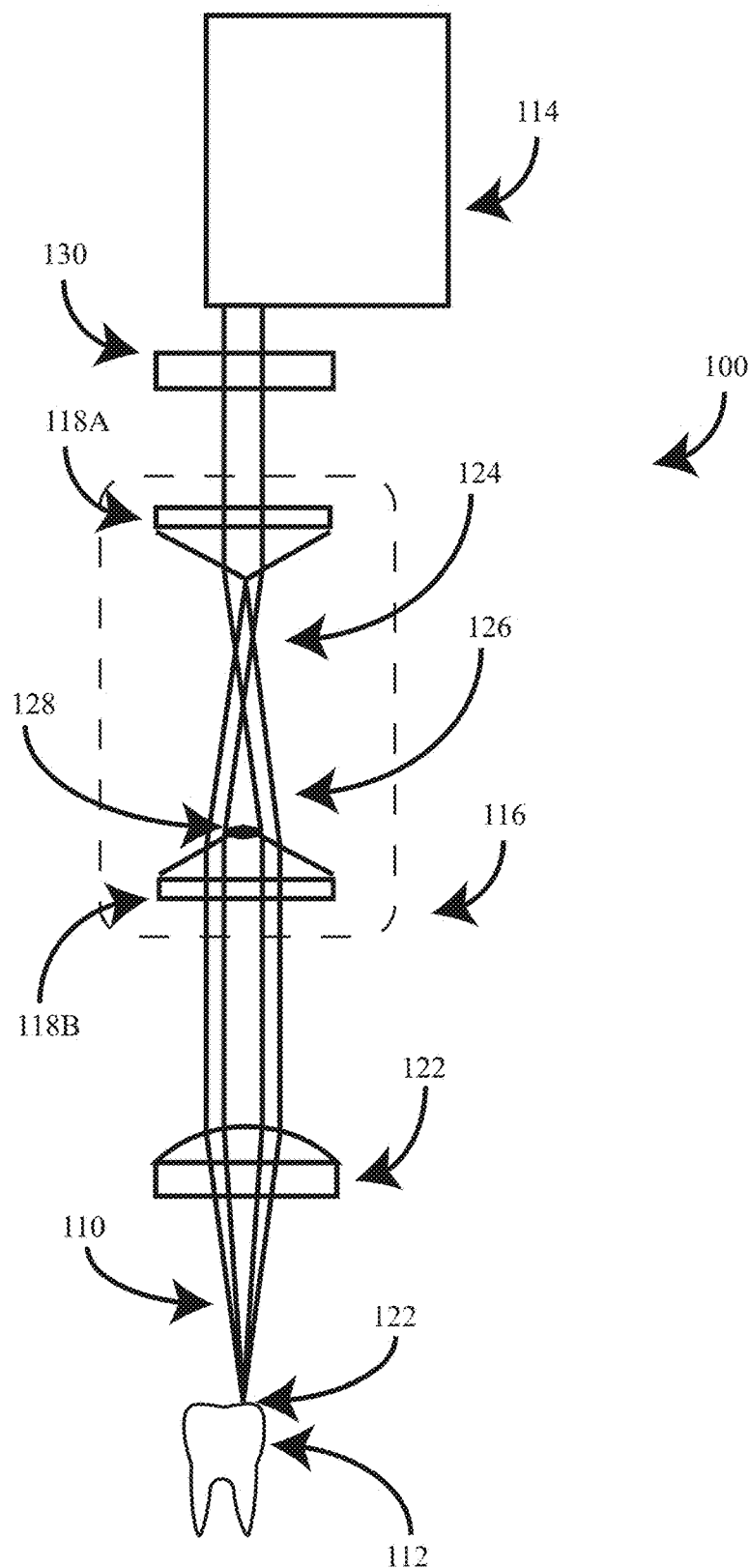
FIG. 1 illustrates a laser system, in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. The following detailed description is, therefore, not to be taken in a limiting sense.

Transverse Electromagnetic Modes for Even Treatment

As disclosed above, much research has been done on the use of a laser for affecting an increase in acid resistance in dental hard tissue, however all of the existing research discloses using a laser having a Gaussian energy profile output. Different wavelengths, energy levels, measurement and control techniques have been explored, but to date there is no solution described in the literature that uses an alternative laser energy profile.

Use of a Gaussian energy profiles (or near-Gaussian energy profiles like those produced by slab $CO_2$ lasers which are Gaussian in one axis and unstable in a second axis) limit performance of laser treatment. For example, see "Nondestructive Assessment of the Inhibition of Enamel Demineralization by $CO_2$ Laser Treatment Using Polarization Sensitive Optical Coherence Tomography," by Hsu et al., published in J. Biomed Optics in 2008 and incorporated herein by reference. Hsu et al. show that melting of the enamel is easily achieved (see FIG. 3a, which shows melted enamel) and a Gaussian energy profile causes variable treatment effectiveness over a focal region of the laser beam (see FIG. 3b, which shows uneven melting of enamel). Consistently effective laser treatment requires that surface temperatures of a tooth experiencing laser heating are held very precisely. However, use of a Gaussian energy profile introduces uneven heating of dental tissue by its very nature. An energy dense peak, at a center of a Gaussian beam will introduce peak heating at the tissue surface. And, a low energy circumference of the laser beam (encompassing the "wings" or "tails" of the Gaussian energy profile) will result in, relatively speaking, much less heating of the tissue. For this reason, there is effectively no way to eliminate variable heating of the tissue with a laser beam having a Gaussian laser energy profile. Laser systems for delivering non-Gaussian energy profiles specifically for the even heating of dental hard tissue are therefore sought.

Further complicating consistent and even heating of dental hard tissue with a laser is that an energy density of a laser beam varies substantially at locations away from the focal region. Energy density of the laser beam varies based upon distance away from the focal region at a rate that depends on a rate of convergence (e.g., numerical aperture [NA]) of the laser beam. A highest energy density occurs at the focal region. Typically, the focal region is located a prescribed distance (e.g., focal length) away from the focus optic, which is in a system (commonly within a hand piece). A distance between the hand piece and the dental surface being treated, therefore, must be carefully maintained in order to control the energy density of the beam as it affects the surface. Additionally, a density of energy absorbed into the dental surface varies depending on an angle of an optical axis relative the dental surface (more energy is absorbed by the dental surface at more orthogonal angles). A commercially viable hand piece ultimately must be used by a dental practitioner in a real-world clinic. So, precise placement of the focal region coincident and parallel with the surface of the dental tissue being treated cannot reasonably be expected in situ. Instead, carefully specifying a laser beam having an energy profile and a rate of convergence that is insensitive to small deviations from the focal region is preferred. Exemplary embodiments are disclosed herein that address these above-mentioned problems.

FIG. 1 illustrates a preventative dental laser system 100 in accordance with one embodiment. The preventative dental laser system 100 delivers a laser beam 110 to a dental hard tissue 112 (e.g., enamel, dentin, or cementum). The laser beam is generated by a laser source 114. An exemplary laser source 114 is a carbon dioxide ($CO_2$) laser, for example HPP DL-500 from Access Laser of Everett, Washington, U.S.A. Typically, the laser source is selected to generate a laser beam 110 that is well absorbed (e.g., has a wavelength having an absorption coefficient greater than 1 $cm^{-1}$, 100 $cm^{-1}$, or 1,000 $cm^{-1}$) by the dental hard tissue 112. The laser beam has a transverse electromagnetic mode (TEM) that is non-Gaussian. For example, in accordance with one embodiment, the laser beam 110 has a TEM that comprises at least one ring (e.g., TEM 01*). According to some embodiments, the system 100 comprises a beam shaper 116. The beam shaper 116 in some embodiments introduces the transverse ring mode to the laser beam 110. Exemplary beam shapers 116 for introducing a transverse ring mode to the laser beam can include: one or more of axicons 118A-B, an aperture (e.g., annular slit located at a back focal plane of a convergent lens), a spatial light modulator, fiber optics or waveguides, a tunable acoustic gradient (TAG) lens, a diffractive optical element (DOE), spiral phase plates (SPP), optical phase plates, a rod homogenizer, and spatial phase masks. Alternatively, in some embodiments, the laser beam 110 is generated having a non-Gaussian (e.g., transverse ring) mode. Exemplary laser sources 114 that can produce a laser beam 110 having a non-Gaussian (e.g., transverse ring) mode are DC series $CO_2$ lasers from ROFIN-SINAR Laser GmbH of Hamburg, Germany. The laser beam 110 is focused by a focus optic 120 to a focal region 122. An exemplary focus optic is (Thorlabs PN: LA7728-G) a 1" diameters ZnSe plano-convex lens, with a focal length of 200.0 mm having an antireflective coating in a range from 7 to 12 μm. In some embodiments, the laser beam 110 at the focal region 122 maintains its non-Gaussian (e.g., transverse ring) energy profile. The focal length of the focus optic, in some embodiments, can be specified in order to control rate of convergence (and/or divergence) of the laser beam. A reduced rate of convergence (i.e., slower optical system) reduces changes in energy profile away from the focal region. For example, a collimated laser beam having a diameter of 10 mm acted upon by a focus optic having a 200 mm focal length converges at a numerical aperture (NA) of 0.025. Comparatively, the same 10 mm laser beam being focus by a 50 mm focal length focus optic will converge at a NA of 0.1. Beam widths are shown for a 0.025 NA beam and a 0.1NA at certain distances away from focus in the table below:

| | | |
|---|---|---|
| Numerical Aperture (NA) (-) | 0.025 | 0.1 |
| Wavelength (micron) | 10.6 | |
| Focal Region Width (micron) | 135.0 | 33.7 |
| Rayleigh Length (mm) | 5.4 | 0.3 |
| Width of Beam 0.1 mm from Focal Region (micron) | 135.0 | 35.2 |
| Change in Area (or Energy Density) 0.1 mm from Focal Region (%) | 0.0% | 8.8% |
| Width of Beam 1 mm from Focal Region (micron) | 137.3 | 105.5 |
| Change in Area (or Energy Density) 1 mm from Focal Region (%) | 3.4% | 878.4% |
| Width of Beam 10 mm from Focal Region (micron) | 284.1 | 1000.6 |
| Change in Area (or Energy Density) 10 mm from Focal Region (%) | 343.1% | 87839.1% |

As is manifest in the table above, a smaller numerical aperture (e.g., less than 0.1) allows small deviations from the focal region (e.g., +/−0.5, 1, 2, 3, or 5 mm) to have relatively small differences in energy density (e.g., 10%, 25%, or 50%). Use of the system typically includes a clinician placing a hand piece within a patient's mouth and directing the laser beam toward a dental hard tissue surface. The location of the focal region relative the surface is therefore affected by an optical path length (between the focus optic and the surface). The optical path length must be controlled by the clinician. Accurate control of a distance between the hand piece and the dental hard tissue is impractical in situ. For this reason, selection of focal length (or numerical aperture [NA]) in some embodiments is made to provide a pseudo-invariable energy density near the focal region (for example, less than a 10% change in energy density [e.g., fluence] in 1 mm from focus). In accordance with one embodiment, the non-Gaussian mode is imparted upon the laser beam 110 by a beam shaper comprising one or more axicons 118A-118B. As shown in FIG. 1, a first axicon in some embodiments is used to form a quasi-Bessel beam 124 and then a diverging transverse ring beam 126. In some embodiments, the diverging ring beam 126 is focused directly by the focus optic 122. Alternatively, a second axicon 118B having a wedge angle substantially equal to that of the first axicon 118A is used to collimate the diverging ring beam 126 into a collimated laser beam 110 having a transverse ring mode. In some embodiments, a mask 128 is used to partially occlude the laser beam 110, in order to ensure that a center portion of the laser beam 110 is substantially free from laser energy.

According to one embodiment, the system additionally includes a beam scanning system. Exemplary beam scanning systems include Risley prisms, spinning polygon mirrors, voice coil scanners (e.g., Part No. MR-15-30 from Optotune of Dietikon, Switzerland), galvanometers (e.g., Lightning II 2-axis scan head from Cambridge Technology of Bedford, Massachusetts, U.S.A.), and a gantry with a translating focus optic. Scanning methods related to dental laser systems are described in U.S. Pat. No. 9,408,673 by N. Monty et al., incorporated herein by reference.

According to one embodiment, a polarization of the laser beam 110 is controlled. In some cases, an intra-cavity polarization generator is used (not shown) (e.g., a leaky-mode polarizing grating mirror at an output coupler of a waveguide $CO_2$ laser). Alternatively, in other cases an external polarization converter 130 is used to convert the laser beam to a desired polarization state. Exemplary polarization converters 130 include one half waveplate, one quarter waveplate, and a linear to radial/tangential polarization converter that is composed of 8 low-order half-wave segments and which has a fixed and well-defined fast-axis orientation. The laser beam 110 in certain exemplary embodiments has a cylindrical polarization (i.e., axially symmetric polarization) (e.g., radial or tangential). Alternatively, in other certain exemplary embodiments, the laser beam 110 has a polarization that is linear, circular, random, or azimuthal. Polarization of the laser beam in some embodiments affects the amount of energy delivered into the dental hard tissue.

An amount of reflection (e.g., reflectivity) of a radiation at a surface of a material is related to polarization. In some situations, it is appropriate to understand a relationship between polarization and reflectivity according to Fresnel equations. Reflectivity of an s-polarized light is described by a first Fresnel equation as:

$$R_s = \left| \frac{n_1 \cos \theta_i - n_2 \sqrt{1 - \left(\frac{n_1}{n_2}\sin \theta_i\right)}}{n_1 \cos \theta_i - n_2 \sqrt{1 - \left(\frac{n_1}{n_2}\sin \theta_i\right)}} \right|^2$$

where $R_s$ is reflectivity for s-polarization, mi is index of refraction of a first medium (e.g., air), $n_2$ is an index of refraction of a second medium (e.g., dental hard tissue), $\theta_i$ is an angle of incidence the radiation is reflected from the surface about. Reflectivity for p-polarization, $R_p$, is described by a second Fresnel equation as:

$$R_p = \left| \frac{n_1 \sqrt{1 - \left(\frac{n_1}{n_2}\sin \theta_i\right)} - n_2 \cos \theta_i}{n_1 \sqrt{1 - \left(\frac{n_1}{n_2}\sin \theta_i\right)} + n_2 \cos \theta_i} \right|^2$$

Finally, energy transmitted into the material is all of the energy not reflected as described by $$T_s = 1 - R_s$$

and, $$T_p = 1 - T_p$$

where $T_s$ is s-polarized radiation transmitted into the material; and, $T_p$ is p-polarized radiation transmitted into the material.

Figure 2A:
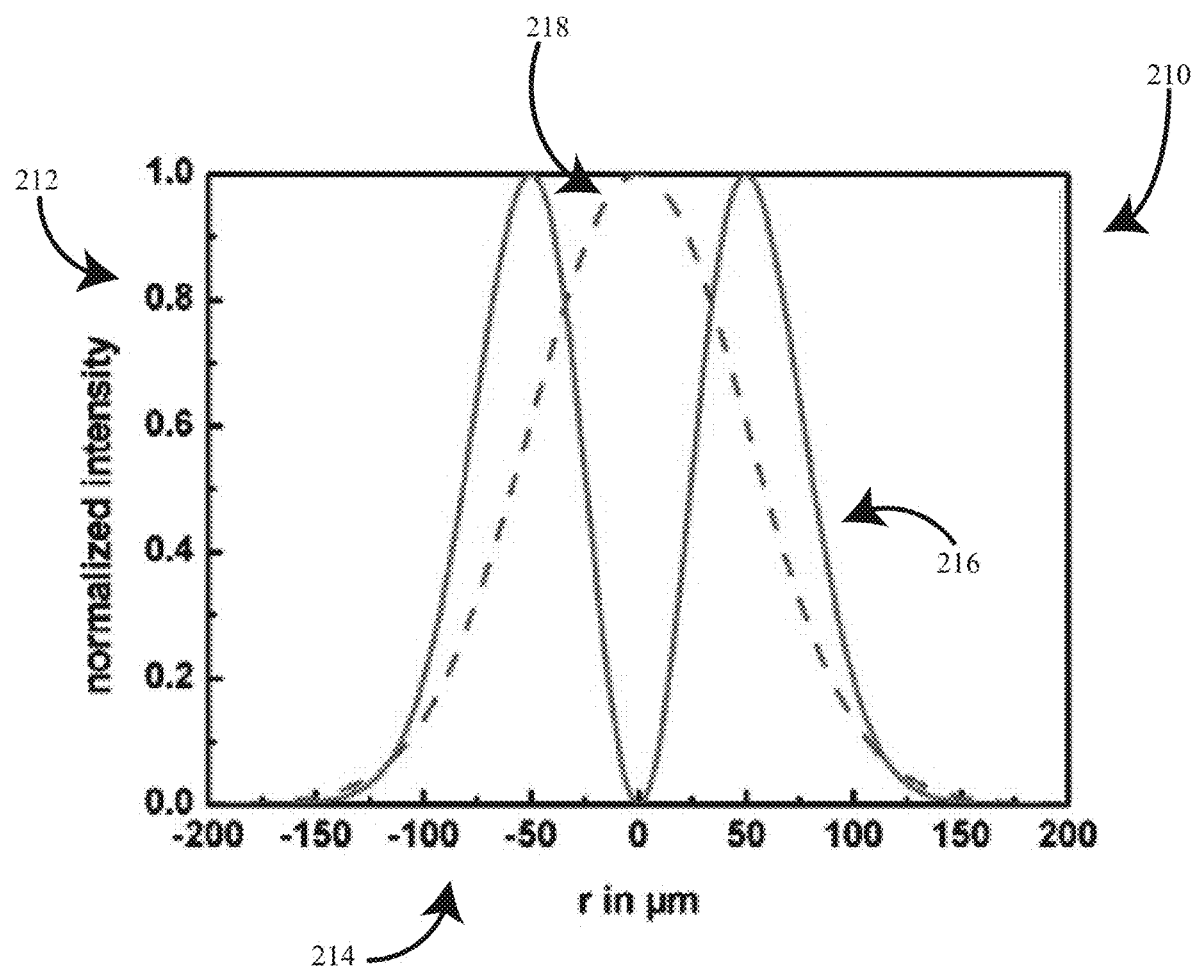
FIG. 2A illustrates a transverse ring mode energy profile compared to a Gaussian energy profile, in a certain exemplary embodiment.
Figure 2B:
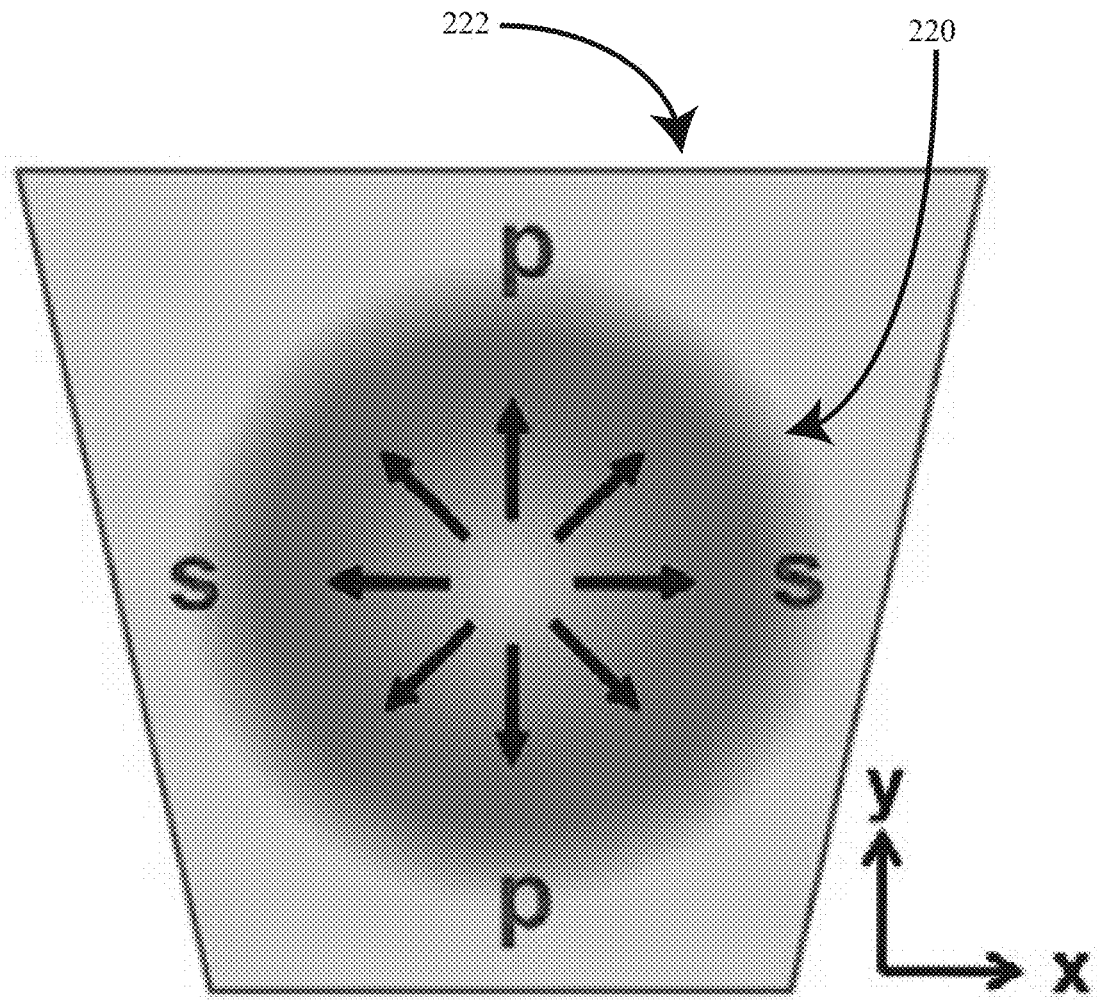
FIG. 2B illustrates a transverse ring mode subtended upon a tilted surface, in an exemplary embodiment.
Figure 2C:
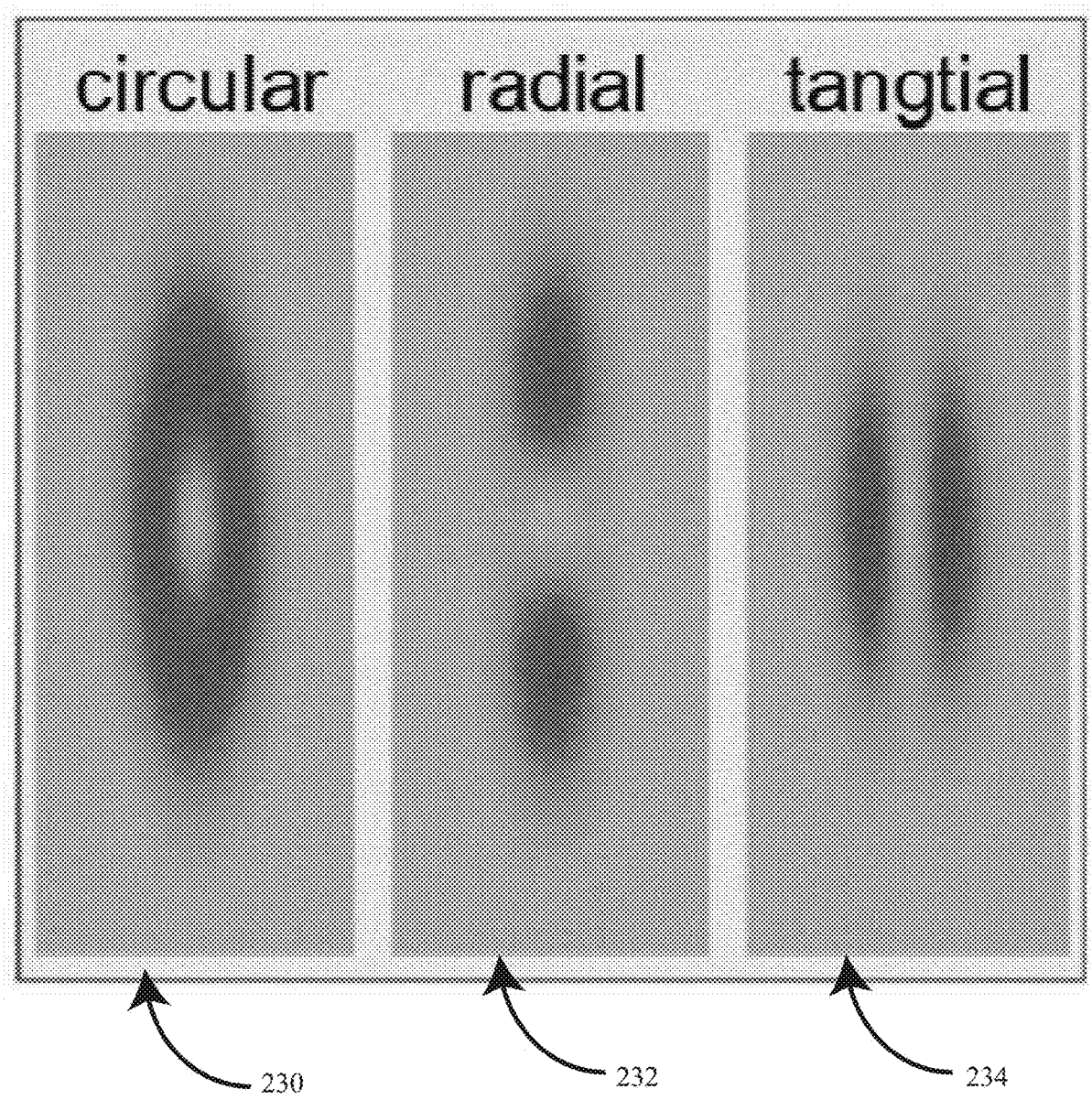
FIG. 2C illustrates relative energy absorption from the configuration shown in FIG. 2B with varying polarization arrangements, in an exemplary embodiment.

Polarization of laser radiation is known to affect industrial laser applications, such as laser welding. In "Effects of Radial and Tangential Polarization in Laser Material Processing" by R. Weber et al., published in Physics Procedia in 2011, incorporated herein by reference, an overview is given on polarization control and polarization effects as they relate to state-of-the-art industrial laser processing activities, including laser cutting, laser welding, and laser annealing. FIGS. 2A-C illustrates an example showing how polarization effects transmission from R. Weber et al. FIG. 2A is an energy profile graph 210 having normalized intensity in normalized units along a first vertical axis 212 and radial position in micron along a first horizontal axis 214. A transverse ring mode 216 is compared with a Gaussian mode 218 within the graph. Referring now to FIG. 2B, a laser beam 220 is shown irradiating a surface 222. The surface is not normal to the laser beam 220, but instead is tilted at 80° relative the laser beam 220. Absorbed energy resulting from the configuration shown in FIG. 2B is illustrated in FIG. 2C. A first image 230 of the surface 222 illustrates absorbed energy when the laser beam 220 is circularly polarized. A second image 232 image of the surface 222 illustrates absorbed energy when the laser beam is radially polarized. A third image 234 of the surface illustrates absorbed energy when the laser beam is tangentially polarized. In the configuration described with reference to FIG. 2B, absorption of energy is more constant over the entire area irradiated by the laser beam with circular polarization 230. The phenomenon described in reference to FIGS. 2A-C can be understood mathematically using the Fresnel equations described above.

Other forms of beam shaping have been identified that produce energy profiles that are constant (e.g., top hat or flat-top) or near-constant (super-Gaussian). Flat-top (i.e., top hat) laser energy profiles are not defined as free space modes, as the energy profile changes as the beam propagates. Flat-top energy profiles can be shaped by diffractive optical elements (DOE), for example PN: ST-273-A-Y-A from Holo/OR of Ness Ziona, Israel. Other DOEs can be used to produce a diffuse or homogenized laser beam. Generally, all of these DOEs only produce a flat-top energy profile at focus (e.g., beam waist) and outside of focus the energy profile is indeterminate. For this reason, flat-top and top-hat energy profiles (which would theoretically be ideal for the described application) in practice are difficult to implement. Specifically, the flat-top energy profile must be configured so its position along the optical axis coincides with the surface of the tooth. Away from the flat-top profile position (e.g., focus) along the optical axis, the flat-top profile changes and exhibits "hot spots" (or areas of peak energy density). These "hot spots" when positioned at the surface of the tooth typically cause unwanted thermal damage to the tooth (e.g., melting, cracking, and ablation). In order to prevent this with a flat-top energy profile, the optical path length to the surface of the tooth must remain constant during treatment. This is difficult in practice, as every treatment surface of each tooth within the mouth must be irradiated at a clinically viable speed (e.g., a total treatment time of less than 30 minutes) and because of the complex nature of working within an oral cavity. Like the flat-top energy profile a super-Gaussian energy profile changes with propagation distance. However, unlike the flat-top energy profile the changes are slow and predictable. For example, short distances (e.g., +/−1 mm or +/−10 mm) away from the super-Gaussian energy profile location (e.g., focus) the energy profile shape changes only slightly. Typically, changes away from the super-Gaussian energy profile are toward a shape that is more Gaussian or more donut (i.e., dog ears) in its energy profile. This is again unlike the flat-top energy profiles described above that can introduce peak fluence "hot spots" in indeterminate locations during propagation. In some embodiments, a transverse energy profile of the laser beam 110 is not a ring mode, but instead has a more constant energy distribution, for example a super-Gaussian.

A standard Gaussian laser beam energy (or power) profile at focus can be modeled according to:

$$I_{(r)} = I_0 e^{-2\left(\frac{r}{\omega_0}\right)^2}$$

where, $I_{(r)}$ is a transverse energy (or power) density profile, $I_0$ is a peak energy (or power) density value (which is typically located at a center of the beam), r is a dependent variable for radius or distance away from the center of the beam, and $\omega_0$ is a $1/e^2$ half width of the laser beam. A higher-order Gaussian (e.g., super-Gaussian) laser beam energy (or power) profile at focus can be modeled according to:

$$I_{(r)} = I_0 e^{-2\left(\frac{r}{\omega_0}\right)^n}$$

where, n is an order of the super-Gaussian, for example 4, 6, 8, etc. In accordance with one embodiment, the system comprises a laser source configured to generate a laser beam having a super-Gaussian beam profile.

In some embodiments, a phase-graded mirror is employed within a laser resonator to generate the laser beam having a super-Gaussian beam profile. For example, researchers have shown that generation of a super-Gaussian beam using a phase-grated mirror can increase energy extraction within a carbon dioxide laser. "Super-Gaussian Output from a $CO_2$ Laser by using a Graded-Phase Mirror," by P. Belanger et al., published in Optics Letters in 1992, incorporated herein by reference, teaches formation of super-Gaussian output resonators with orders of 4 and 6 in a transverse excited atmospheric pressure (TEA) $CO_2$ laser. Later in 1998, G. Bourdet et al. taught that a slab $CO_2$ could theoretically experience increased energy extraction from the gain medium by using a graded-phase mirror to generate a quasi-super-Gaussian laser mode in "Theoretical investigations of a slab $CO_2$ Laser Resonator with Graded-Phase Mirror," published in Optics Communications and incorporated herein by reference.

In some embodiments, active optical elements are used to generate or shape a mode of the laser beam. For example, T. Cherezova et al. reported formation of super-Gaussian modes having orders of 4, 6, and 8 using a deformable mirror in a carbon dioxide laser resonator in 2001 in a paper entitled "Active laser resonator performance; formation of a specified intensity output," published in Applied Optics and incorporated herein by reference.

Figure 3:
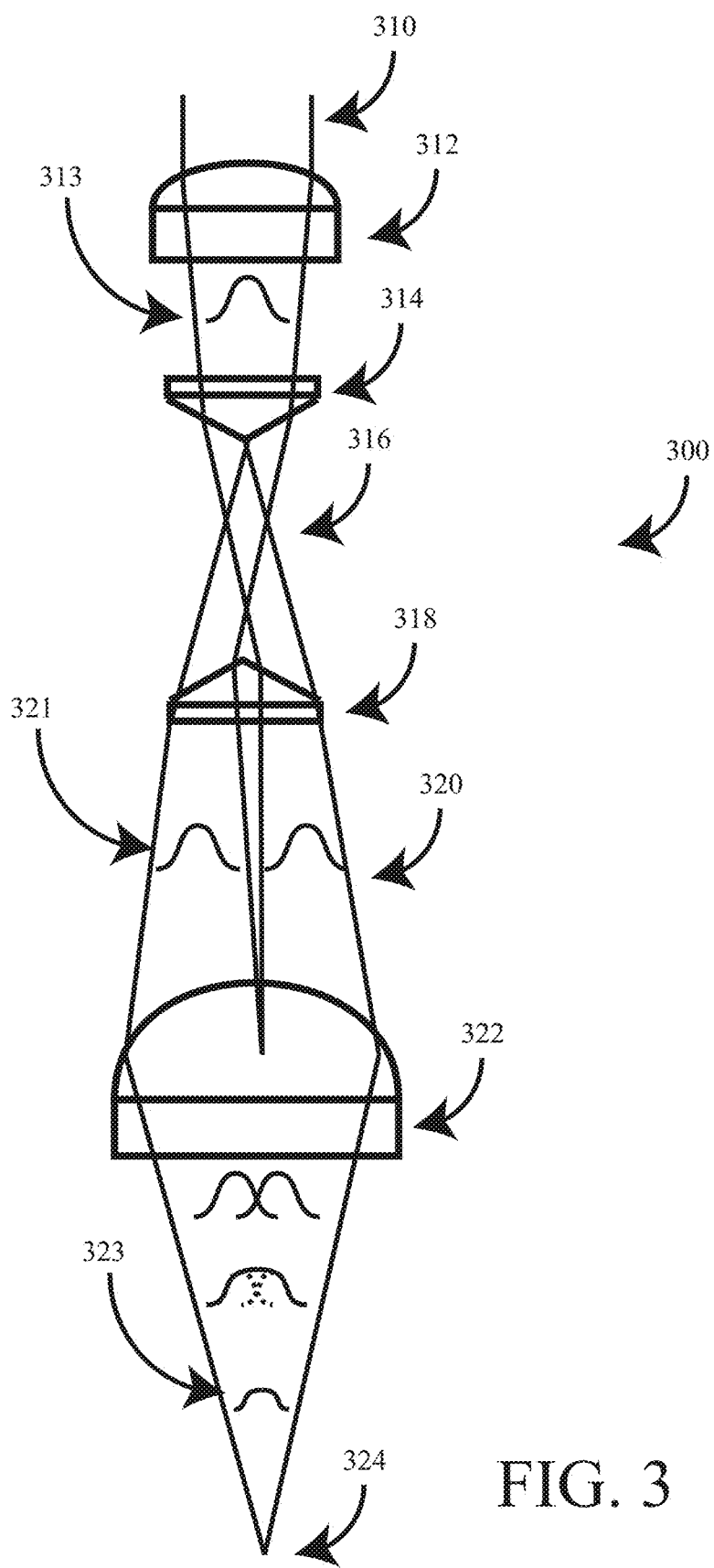
FIG. 3 illustrates an optical arrangement for laser beam shaping, in accordance with one embodiment.

According to a certain embodiment illustrated in FIG. 3, an optical arrangement 300 is used to shape a laser beam 310 into an energy profile having a more uniform energy distribution. A collimated laser beam 312 having a substantially Gaussian profile 313 is converged to a waist proximal a first axicon 314. The waist of the converging laser beam is generally centered on the first axicon 314. Down beam from the first axicon 314, the laser beam passes through a Bessel beam region 316 then a diverging annulus ring region 318. A second axicon 320 is located down beam from the first axicon a specified distance along an optical axis, such that the diverging annulus ring is of a certain annulus diameter, where the laser beam is incident the second axicon 320. The second axicon 320 then corrects (e.g., collimates) the diverging ring mode into a ring mode that has a substantially constant diameter (D) as it propagates. The ring mode has an annular Gaussian energy profile 321 over the annulus. However, because the waist of the converging beam was located near the first axicon 314, the laser beam was diverging as it was acted on by the first axicon 314 as well as the second axicon 320. As a result, an annulus width (w) of the ring mode continues to diverge as the laser beam propagates. A focus optic is located a predetermined distance down beam from the second axicon 320, such that at the location of the focus optic the diameter (D) of the annulus is generally equal to the width (w) of the annulus. Here, because of the partially overlapping annular energy profiles, the laser beam has a more constant energy profile 323. Finally, the focus optic 322 converges the laser beam to a focal region. Alternatively, in some certain embodiments, a more constant energy profile (e.g., super-Gaussian) is formed by an intra-cavity spatial filter or a spatial filter external to a laser cavity.

To understand and demonstrate effects of energy profile on heating of dental enamel a mathematical model is disclosed. The mathematical model assumes Beers radiation absorption, Newtonian convection, and Fourier conduction. The model was coded using a nodal finite element analysis, which is described by J. Van de Ven et al. in "Laser Transmission Welding of Thermoplastics-Part I: Temperature and Pressure Modeling" published in J. Manuf. Sci. Eng. In October of 2007 and incorporated herein by reference. For the model, a 9.3 µm wavelength radiation is assumed to have a reflectivity of 0.4 and an absorption coefficient of 0.5 µm$^{-1}$ in dental enamel. An optical pulse of 100 μS is also assumed having an instantaneous rise and fall time. Temperature within the enamel immediately after the laser pulse is found from the model.

Figure 4:
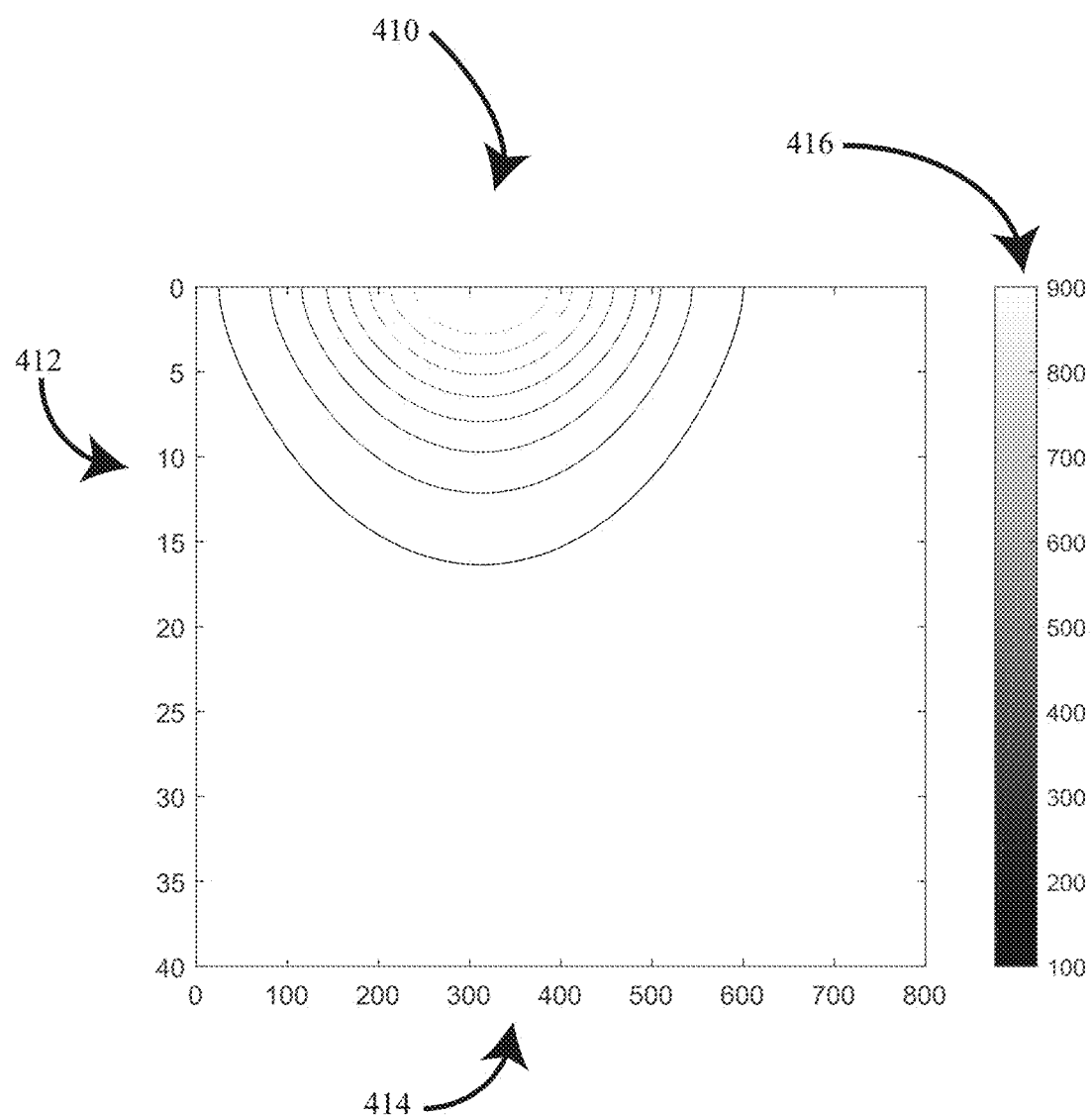
FIG. 4 illustrates an analytically modeled temperature graph of enamel irradiated by a Gaussian beam, in accordance with one embodiment.

A first temperature plot 410 is illustrated in FIG. 4. The first temperature plot shows depth into the enamel in micron along a first vertical axis 412 and width of the laser beam 110 in micron along a first horizontal axis 414. Temperature is grayscale coded in degrees Centigrade according to a color bar 416. The laser beam 110 for the first temperature plot comprises a purely Gaussian energy profile with a $1/e^2$ beam diameter of 0.25 mm.

Figure 5:
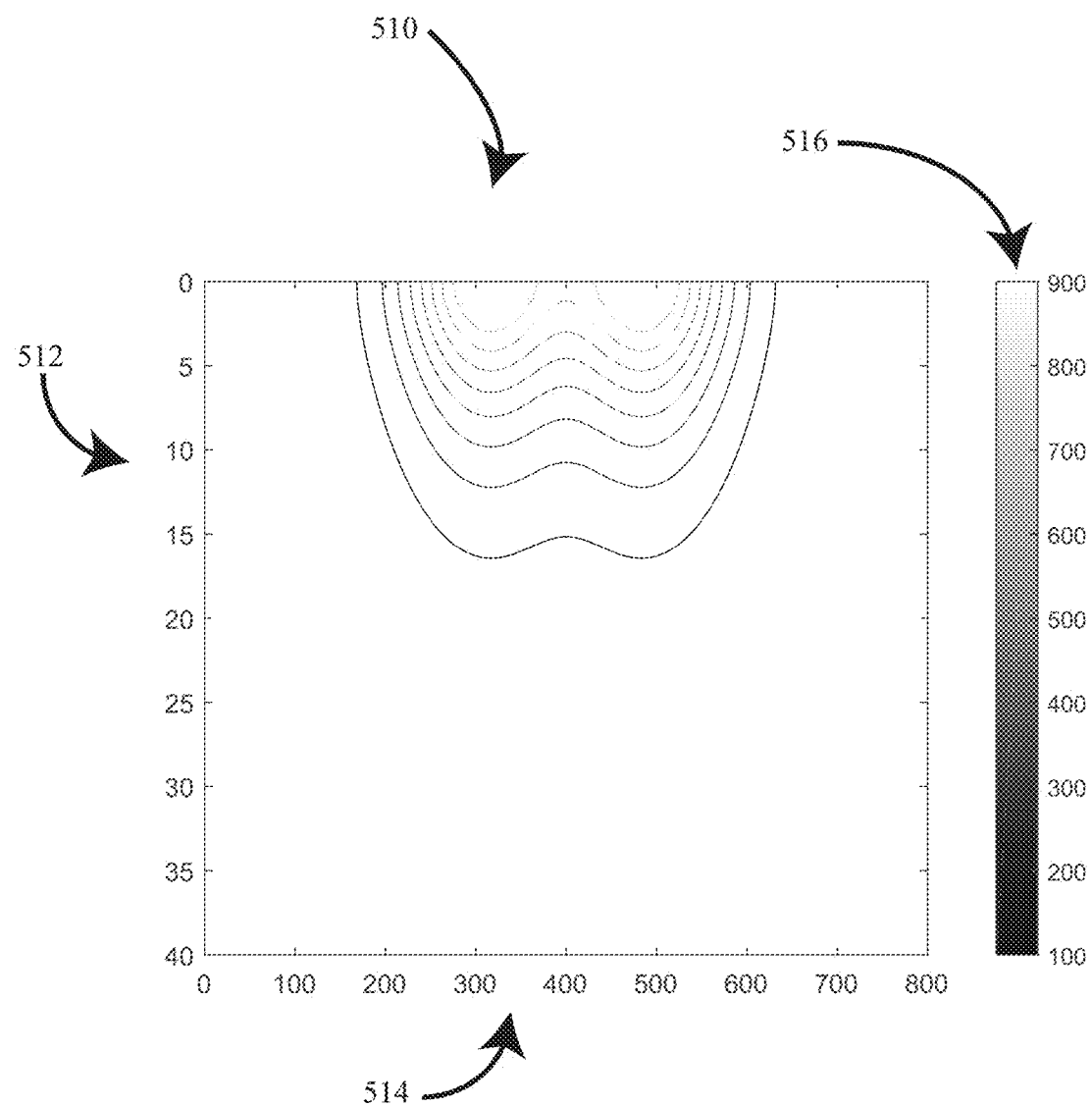
FIG. 5 illustrates an analytically modeled temperature graph of enamel irradiated by a first annular beam, in accordance with one embodiment.

A second temperature plot 510 is illustrated in FIG. 5. The second temperature plot 510 shows depth into the enamel in micron along a second vertical axis 512 and width of the laser beam 510 in micron along a second horizontal axis 414. Temperature is grayscale coded in degrees Centigrade according to a color bar 516. The laser beam 110 for the second temperature plot comprises a transverse ring mode with a Gaussian annular energy profile having a $1/e^2$ beam width of 0.125 mm and annular diameter of 0.175 mm.

Figure 6:
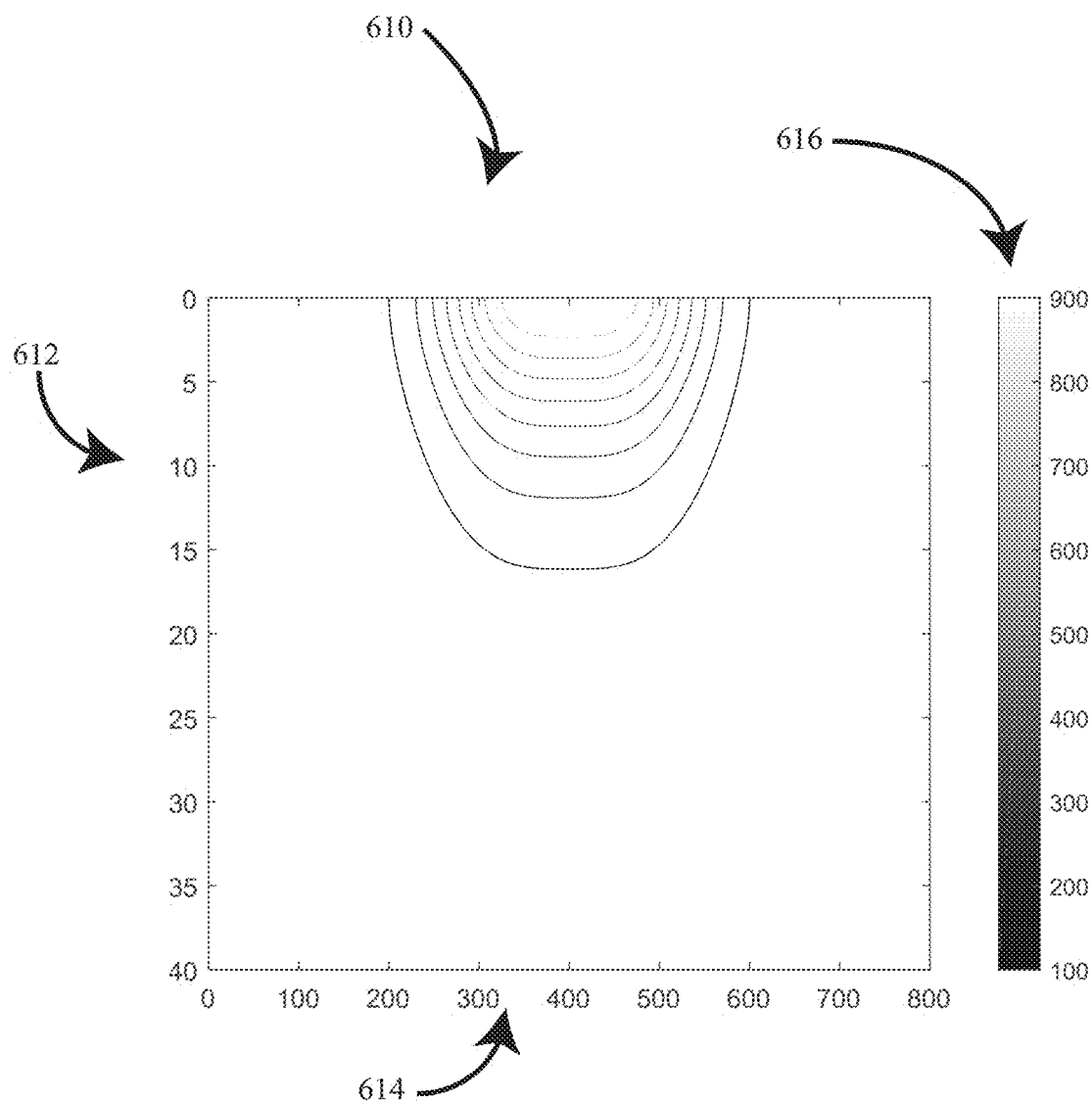
FIG. 6 illustrates an analytically modeled temperature graph of enamel irradiated by a second annular beam, in accordance with one embodiment.

A third temperature plot 610 is illustrated in FIG. 6. The third temperature plot 610 shows depth into the enamel in micron along a third vertical axis 612 and width of the laser beam 610 in micron along a third horizontal axis 614. Temperature is grayscale coded in degrees Centigrade according to a color bar 616. The laser beam 110 for the third temperature plot comprises a transverse ring mode with a Gaussian annular energy profile having a $1/e^2$ beam width of 0.125 mm and annular diameter of 0.125 mm. Review of FIGS. 4-6, shows that a greater area of tissue is heated to a constant temperature with transverse ring mode laser irradiation.

Figure 7:
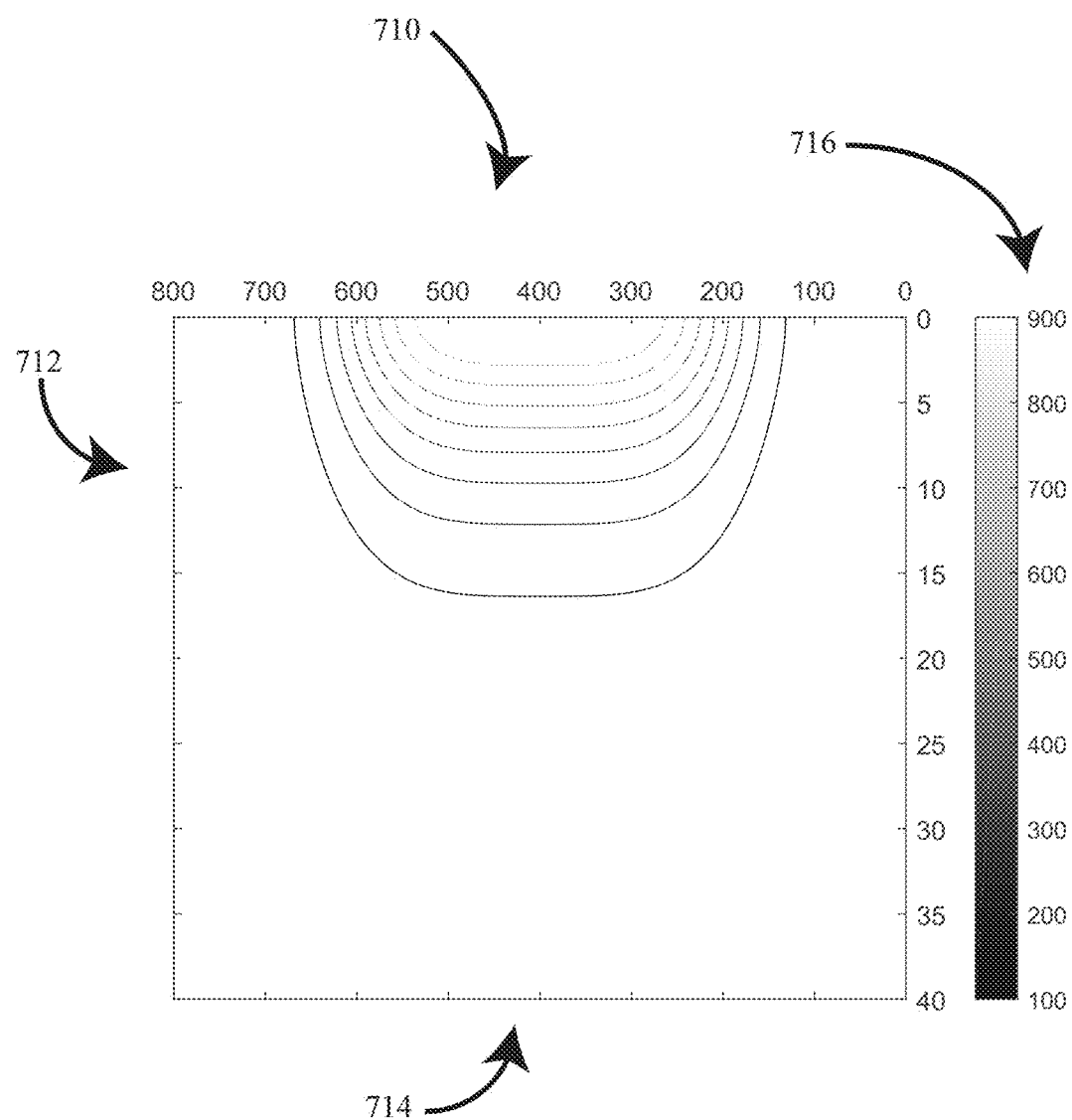
FIG. 7 illustrates an analytically modeled temperature graph of enamel irradiated by a super-Gaussian beam, in accordance with one embodiment.

A fourth temperature plot 710 is illustrated in FIG. 7. The fourth temperature plot 710 shows depth into the enamel in micron along a fourth vertical axis 712 and width of the laser beam 710 in micron along a fourth horizontal axis 614. Temperature is grayscale coded in degrees Centigrade according to a color bar 716. The laser beam 110 for the fourth temperature plot comprises a super-Gaussian energy profile with an order of 4 and a beam width of 0.125 mm. Review of FIGS. 4-7, shows that a greater area of tissue is heated to a constant temperature with a non-Gaussian (i.e., super-Gaussian and transverse ring) mode laser irradiation.

Figure 8:
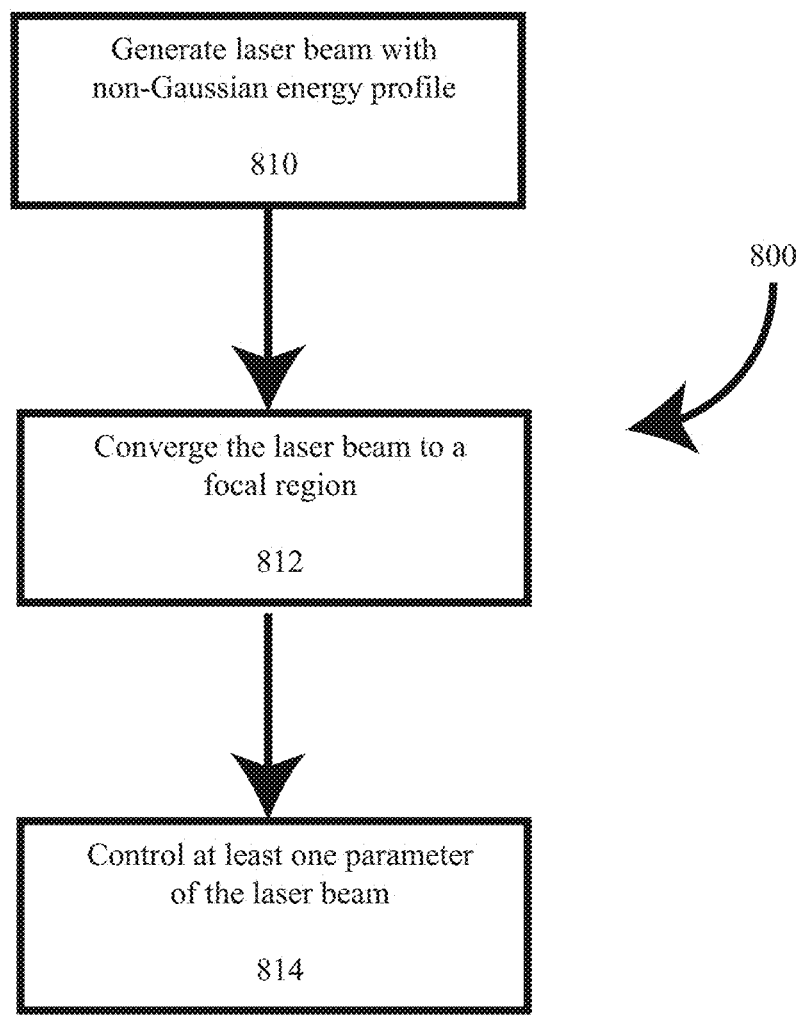
FIG. 8 presents a flowchart of a method for preventative dental laser treatment, in accordance with one embodiment.

FIG. 8 presents a flowchart of a method 800 for preventative dental laser treatment in accordance with one embodiment. A laser source generates a laser beam having a non-Gaussian energy profile (e.g., a transverse ring mode) 810. In some cases, the laser source first generates the laser beam and then an energy profile of the laser beam is converted into a non-Gaussian energy profile. In other cases, the laser sources generates the laser beam having a non-Gaussian energy profile natively. In accordance with one embodiment, the non-Gaussian energy profile comprises a transverse ring mode. Examples of transverse ring modes include TEM 01* modes, Laguerre-Gaussian modes, Hermite-Gaussian modes, Bessel, and Bessel-Gaussian modes. In some embodiments, the non-Gaussian energy profile is used to produce a constant or near-constant energy profile (e.g., super-Gaussian) somewhere along the propagation of the laser beam (e.g., a focal region). Next, the laser beam is converged to a focal region 812, typically using a focus optic. The focal region is located near a surface of dental hard tissue (e.g., tooth enamel). Finally, at least one parameter of the laser beam is controlled 814 to deliver a controlled irradiation and evenly heat a portion of the surface of the dental hard tissue to within a range of between about 400° C. and about 1300° C. Examples of laser parameters include: repetition rate, pulse duration, pulse energy, focal region position, laser scan speed, focal region width, wavelength, etc.

To aid in practice of the claimed invention and parameter selection a table is provided below with exemplary ranges and nominal values for relevant parameters.

| Parameter | Min. | Max. | Nom. |
| --- | --- | --- | --- |
| Repetition Rate | 1 Hz | 10 KHz | 1 KHz |
| Pulse Energy | 1 μJ | 1 J | 10 mJ |
| Focal Region Width | 1 μm | 10 mm | 1 mm |
| Fluence | 0.01 J/cm$^2$ | 1 MJ/cm$^2$ | 1 J/cm$^2$ |
| Wavelength | 200-500 nm | 4000-12000 nm | 10.6 μm |
| Numerical Aperture (NA) | 0.00001 | 0.5 | 0.01 |
| Focal length | 10 mm | 1000 mm | 200 mm |
| Average Power | 1 mW | 100 W | 1 W |
| Peak Power | 50 mW | 5000 W | 500 W |
| Scan Speed | 0.001 mm/S | 100,000 mm/S | 10 mm/S |
| Scan Location Spacing | 0 | 10x Focal Region Width | 0.5x Focal Region Width |
| Polarization | Linear, circular, random, cylindrical, radial, tangential | | |
| Mode/Energy Profile | Super-Gaussian, annular ring mode, TEM 01*, flat-top, top-hat, Laguerre-Gaussian, Hermite-Gaussian, Bessel, Bessel-Gaussian | | |

Figure 9:
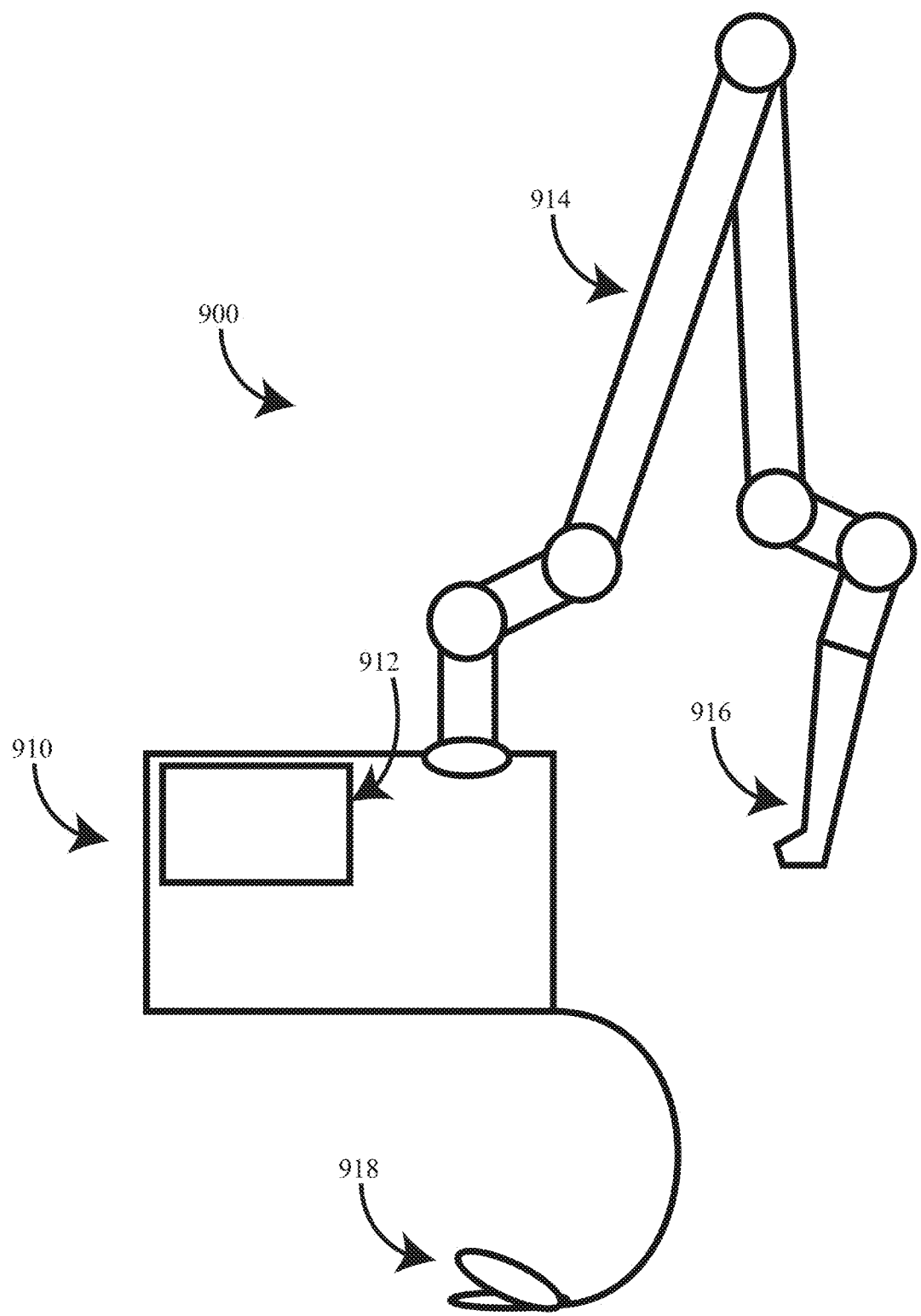
FIG. 9 illustrates an exemplary system for preventative dental laser treatment, in accordance with one embodiment.

An exemplary system 900 is shown in FIG. 9. The system 900 includes a console 910. The console 910 houses components of the system 900, for example, a laser source to generate the laser beam, a direct current (DC) power supply to power the laser source, a beam shaper to shape an energy profile of the laser beam, a compressed air system to deliver compressed air for bulk cooling of dental hard tissue being treated, and a user interface 912 for user control. A beam delivery system 914 directs the laser beam to a hand piece 916. Exemplary beam delivery systems 914 include articulated arms, waveguides, and fiber optics. An exemplary articulated arm is provided by Laser Mechanisms of Novi, Michigan, U.S.A. The hand piece 916 is configured to be used intra-orally (i.e., within an oral cavity). Typically, the hand piece 916 includes a focus optic (not shown) that converges the laser beam to a focal region outside of the hand piece 916. In accordance with one embodiment, the system 900 is operated with a foot pedal 918, which is configured to initiate the laser source.

In accordance with one embodiment, the system 900 is used by a clinician. First, the clinician inputs operating parameters into the user interface 912, for example by using a touch screen. Then the clinician places the hand piece 916 within a patient's mouth and directs the hand piece 916 toward dental hard tissue. For example, the clinician positions the hand piece 916 so that a focal region of the laser beam is coincident with or near (e.g., +/−1 mm, 2 mm, 3 mm, or 5 mm) a surface of a tooth. Then, the clinician activates the laser by stepping on a foot pedal 918. The clinician moves the hand piece 916 within the patient's mouth, carefully directing the focal region of the laser beam near every treatment surface of the patient's teeth.

Contact Coupled Laser Delivery

Figure 10:
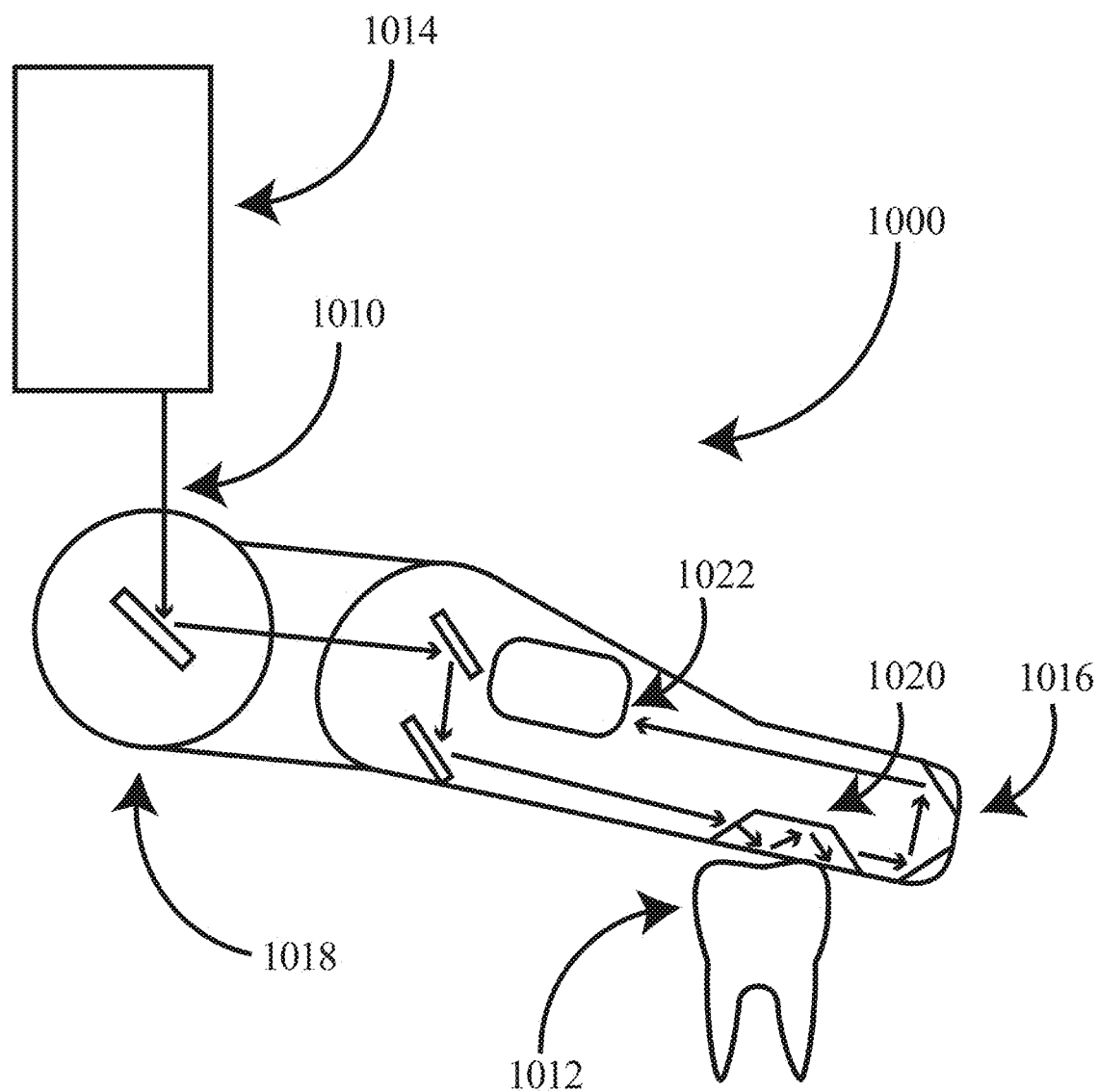
FIG. 10 illustrates a preventative dental treatment system, in accordance with one embodiment.

FIG. 10 illustrates a preventative dental treatment system 1000 in accordance with one embodiment. The preventative dental treatment system 1000 delivers a radiation (e.g., laser beam) 1010 to a dental hard tissue 1012 (e.g., enamel, dentin, or cementum). The radiation is generated by a radiation source (e.g., laser source) 1014. An exemplary laser source 1014 is a carbon dioxide ($CO_2$) laser, for example HPP DL-500 from Access Laser of Everett, Washington, U.S.A. Typically, the radiation source is selected to generate a radiation 1010 having a wavelength that is well absorbed (e.g., has an absorption coefficient greater than 1 $cm^{-1}$, 100 $cm^{-1}$, or 1,000 $cm^{-1}$) by the dental hard tissue 112. Exemplary wavelengths include wavelengths in either of a first range between 200 and 500 nm and second range between 4 and 12 μm. The radiation 1010 is delivered to a hand piece 1016 using a radiation delivery system 1018. Exemplary radiation delivery systems include articulating arms, fiber optics, and hollow wave guides. Certain exemplary articulating arms are provided by Laser Mechanisms of Novi, Michigan, U.S.A. The hand piece 1016 is configured to be used intra-orally (i.e., within an oral cavity). The hand piece 1016 comprises a coupling optic 1020. The coupling optic 1020 accepts the radiation 1010 at a first end of the coupling optic. The radiation 1010 is transmitted within the coupling optic 1020. According to one embodiment, the radiation 1010 is ultimately ejected from a second end of the coupling optic. Exemplary coupling optics include waveguides, fiber optics, rods, and prisms. As, the radiation propagates within the coupling optic 1020 it is internally reflected at interfaces (e.g., sides) of the coupling optic 1020 and its surroundings. Commonly, air surrounds the coupling optic 1020. The coupling optic in some embodiments comprises one of diamond, quartz (i.e., fused silica), glass, sapphire, zinc selenide, or zinc sulfide. In one embodiment the coupling optic 1020 is made out of diamond and produced by chemical vapor deposition (CVD). CVD diamond has an index of refraction of 2.38 at a wavelength of 10.6 μm. Index of refraction of air at a wavelength of 10.6 μm is 1.0. Because, air has a much lower index of refraction than CVD diamond the radiation 1010, in general, experiences total internal reflection (TIR) at optic-air interfaces as it propagates within the coupling optic. The coupling optic 1020 is positioned within the hand piece 116, so that a surface of the coupling optic is exposed. During use of the system 1000, the coupling optic 1020 is placed in contact with dental hard tissue 1012. Depending on radiation parameters (e.g., wavelength), coupling optic parameters (e.g., material [index of refraction]), and optical path parameters (e.g., entrance angle), a varying portion of the radiation 1010 is transmitted into the dental hard tissue 1012 at a point of contact between the coupling optic and the dental hard tissue 1012.

Optionally, after exiting out of the second end of the coupling optic 1020 radiation not delivered to the dental hard tissue 1012 is analyzed by a detector 1022. Exemplary detectors include photodiodes, spectrometers, spectrophotometers, photodetectors, pyroelectric detectors, and thermopiles. In some certain embodiments, the detector 1022 is used to determine an energy or power amount of the radiation 1010 not transmitted into the dental hard tissue. This measurement can indicate whether or not effective treatment is being performed by determining if in fact energy is being delivered into the dental hard tissue 1012. If a small portion of total radiation energy (e.g., less than or equal to 50% of total radiation energy) is detected, than an inference can be made that radiation energy is being delivered to the dental hard tissue 1012 and treatment is being effectively performed. Alternatively, if a large portion (e.g., greater than 50% of the total radiation energy) is detected, than an inference can be made that radiation energy is not effectively being delivered to the dental hard tissue 1012 and that treatment is not effectively being performed.

Figure 11:
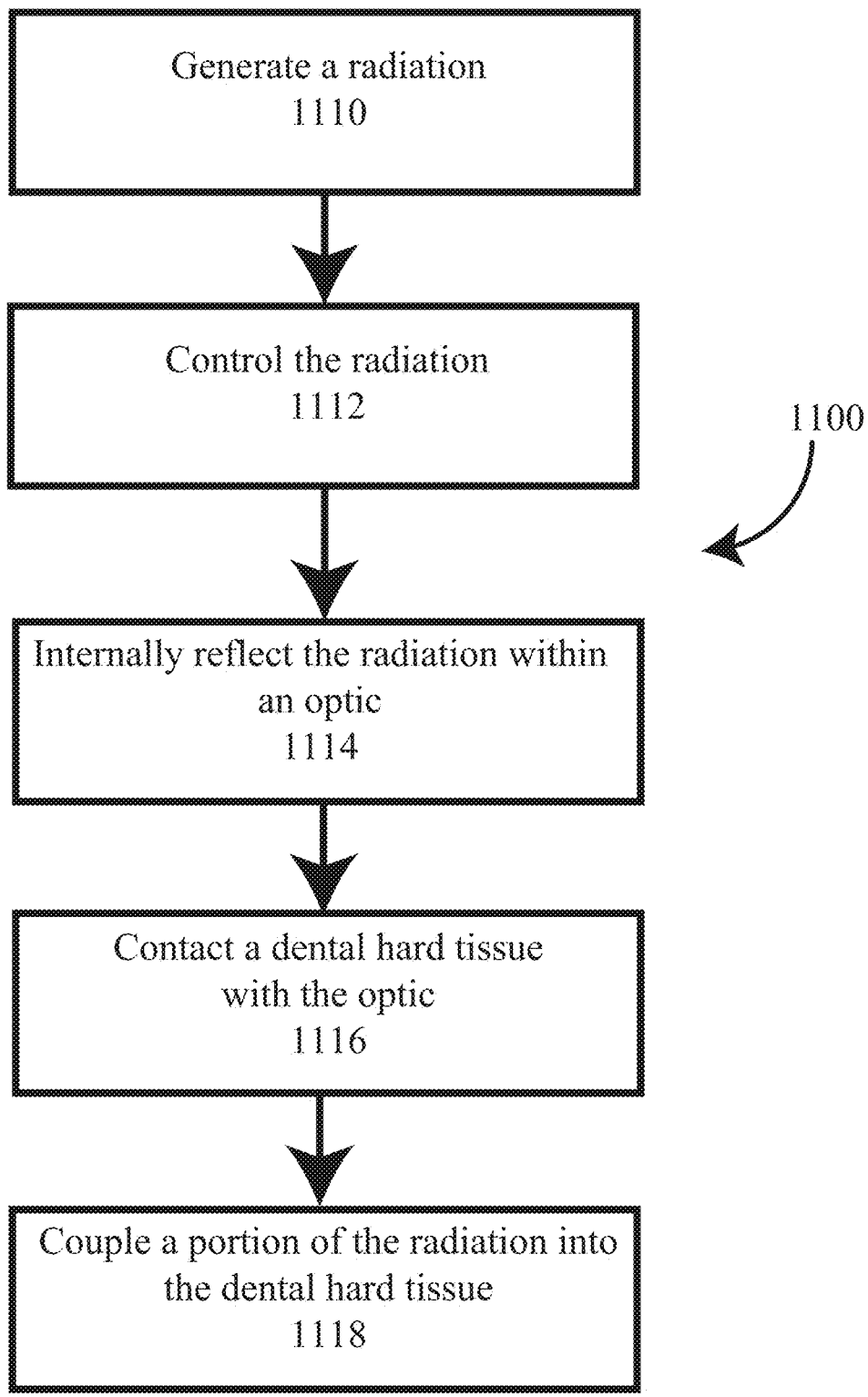
FIG. 11 illustrates a flowchart for a preventative dental treatment method, in accordance with one embodiment.

A certain exemplary method for use of the system 1000 is described with reference to a flowchart 1100 in FIG. 11. First, a radiation (e.g., laser beam) is generated 1110. Typically, the radiation is generated with a radiation source (e.g., laser source). Exemplary laser sources include carbon dioxide ($CO_2$) lasers, carbon monoxide (CO) lasers, excimer lasers, fiber lasers, diode pumped solid state (DPSS) lasers, and semiconductor lasers. The radiation is controlled 1112. Typically, one or more parameters of the radiation are controlled with a controller. Exemplary controllers include laser control boards (e.g., Maestro from LANMark Controls Inc. of Acton, Massachusetts, U.S.A.). The radiation is delivered along an optical path and coupled into an optic. Then, the radiation is internally reflected within the optic 1114. In some certain exemplary embodiments, the radiation while transmitting throughout the optic experiences total internal reflection (TIR). A dental hard tissue is then contacted with the optic 1116. For example, a side of the optic along which the radiation experiences internal reflection is placed in direct contact with a dental hard tissue (e.g., enamel or dentin). Finally, a portion of the radiation is coupled into the dental hard tissue 1118 at a point of contact between the optic and the dental hard tissue. In certain exemplary embodiments, the radiation is coupled into the dental hard tissue by at least one of frustrated total internal reflection (FTIR), attenuated total internal reflection (ATIR), and an evanescent wave.

To aid in practice of the claimed invention and parameter selection a table is provided below with exemplary ranges and nominal values for relevant parameters.

| Parameter | Min. | Max. | Nom. |
| --- | --- | --- | --- |
| Repetition Rate | 1 Hz | 100 KHz | 1 KHz |
| Pulse Energy | 1 μJ | 10 J | 10 mJ |
| Focal Region Width | 1 μm | 10 mm | 1 mm |
| Fluence | 0.01 $J/cm^2$ | 1 $MJ/cm^2$ | 1 $J/cm^2$ |
| Wavelength | 200-500 nm | 4000-12000 nm | 10.6 μm |
| Average Power | 1 mW | 100 W | 1 W |

-continued

| Parameter | Min. | Max. | Nom. |
|---|---|---|---|
| Peak Power | 50 mW | 5000 W | 500 W |
| Coupling Optic Width | 0.1 mm | 50 mm | 5 mm |
| Optic Materials | Sapphire, Quartz, Diamond, UV Fused Silica, Zinc Selenide, Zinc Sulfide, Magnesium Fluoride, Barium Fluoride, Calcium Fluoride, Germanium, and Silicon. | | |

Further description is provided below by way of certain exemplary embodiments. According to some embodiments, an ultraviolet (UV) laser source is used to produce a UV laser beam for treatment. Exemplary UV laser sources include diode pumped solid state (DPSS) lasers, frequency quadrupled Nd: YAG lasers, excimer lasers, and fiber lasers. An exemplary fiber laser series is ULM/ULR-355 Series from IPG Photonics of Oxford, Massachusetts, U.S.A. The ULM/ULR-355 Series offers a 200 W average power system that operates in a quasi-continuous wave (CW) mode with a wavelength of 355 nm, a pulse duration of 1.4 nS, and repetition rate settings of 20, 40, and 80 MHz. Hydroxyapatite (HAP) has a relatively high absorption at 355 nm. The absorption coefficient of HAP at 355 nm is approximately 0.1 µm$^{-1}$ (i.e., 1000 cm$^{-1}$). To understand the potential for a UV laser source (e.g., ULM/ULR-355) a mathematical model is disclosed. The mathematical model assumes Beers absorption, Newtonian convection, and Fourier conduction. The model was coded using a nodal finite element analysis, which is described by J. Van de Ven et al. in "Laser Transmission Welding of Thermoplastics-Part I: Temperature and Pressure Modeling," published in J. Manuf. Sci. Eng. in October of 2007 and incorporated herein by reference. The model was run assuming a 200 W irradiative power, 40% reflectivity between the air and enamel surface, 0.1 µm$^{-1}$ absorption coefficient, and a 1 mm 1/e$^2$ laser beam diameter at the enamel surface with a Gaussian profile. The modeled temperature rise for the above conditions is illustrated in the contour line plot 1200 in FIG. 12.

Figure 12:
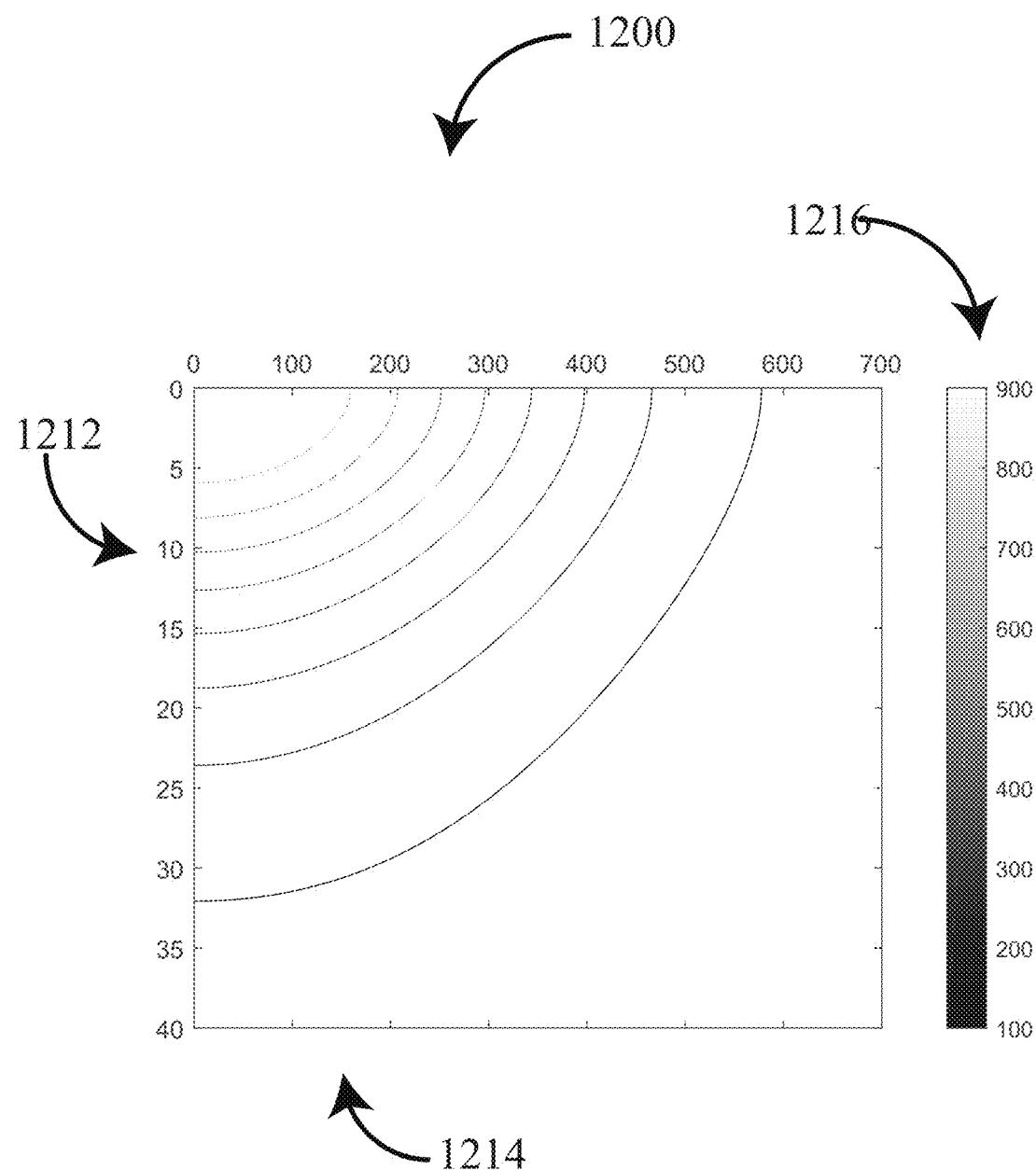
FIG. 12 illustrates a contour temperature plot for irradiated dental hard tissue, in accordance with one embodiment.

Referring to FIG. 12, the contour line plot 1200 shows depth into the enamel in µm along a first vertical axis 1212 and radial distance away from a center of the laser beam in µm along a first horizontal axis 1214. Temperature in degrees Celsius is grayscale coded according to the color bar 1216. The contour plot 1210 illustrates only half of a total width of the area of enamel affected by the laser beam. Said another way a center of the laser beam at a surface of the enamel is shown in FIG. 12 at location (0, 0). Peak surface temperature occurs at the center of the laser beam and at the surface and is modeled to be 974° C. It can be seen in FIG. 12 that temperature rise within the enamel occurs even tens of micron deep (e.g., 20 µm). This is because enamel absorbs UV radiation well, but not as highly as it absorbs mid-infrared irradiation (e.g., 9-11 µm wavelengths). For example, optical penetration depth (depth within which ~63% of irradiation is absorbed) for ultraviolet (UV) radiation is approximately 100 µm; and, optical penetration depth for 9.3 µm wavelength radiation is approximately 2 µm. In some cases, increased optical penetration depth is an advantage for treatment, because the tissue is treated less superficially. A disadvantage of increased optical penetration depth is that a greater volume of enamel must be irradiated to treat the same area of the tooth; and, as a result, more energy must be delivered to raise the temperature of the greater volume of enamel. Returning to the example above, a 200 W powered laser pulse and 100 µS pulse duration will deliver 20 mJ of pulse energy to the tooth. Finally, the laser can be pulsed at a repetition rate. Exemplary repetition rates include rates less than or equal to 100 Hz (e.g., 50 Hz). With a 20 mJ laser pulse energy and a repetition rate of 50 Hz, 1 W of laser power is delivered on average to the tooth. About 1 W of bulk heating power can be removed from a tooth by way of forced convection (e.g., blowing air or another fluid). An additional benefit of treatment with a UV radiation is from tooth whitening resulting from photobleaching. J. Schoenly et al. describe removal of extrinsic stains using a 400 nm wavelength laser in "Near-UV Laser Treatment of Extrinsic Dental Enamel Stains," published in Lasers Surg Med. in March of 2012, incorporated herein by reference. The above example modeled a Gaussian beam being delivered to a dental hard tissue in order to demonstrate feasibility of a UV laser beam for acid dissolution inhibition treatment. In certain exemplary embodiments, the UV laser beam is delivered by way of an optic that contacts the dental hard tissue.

Figure 13A:
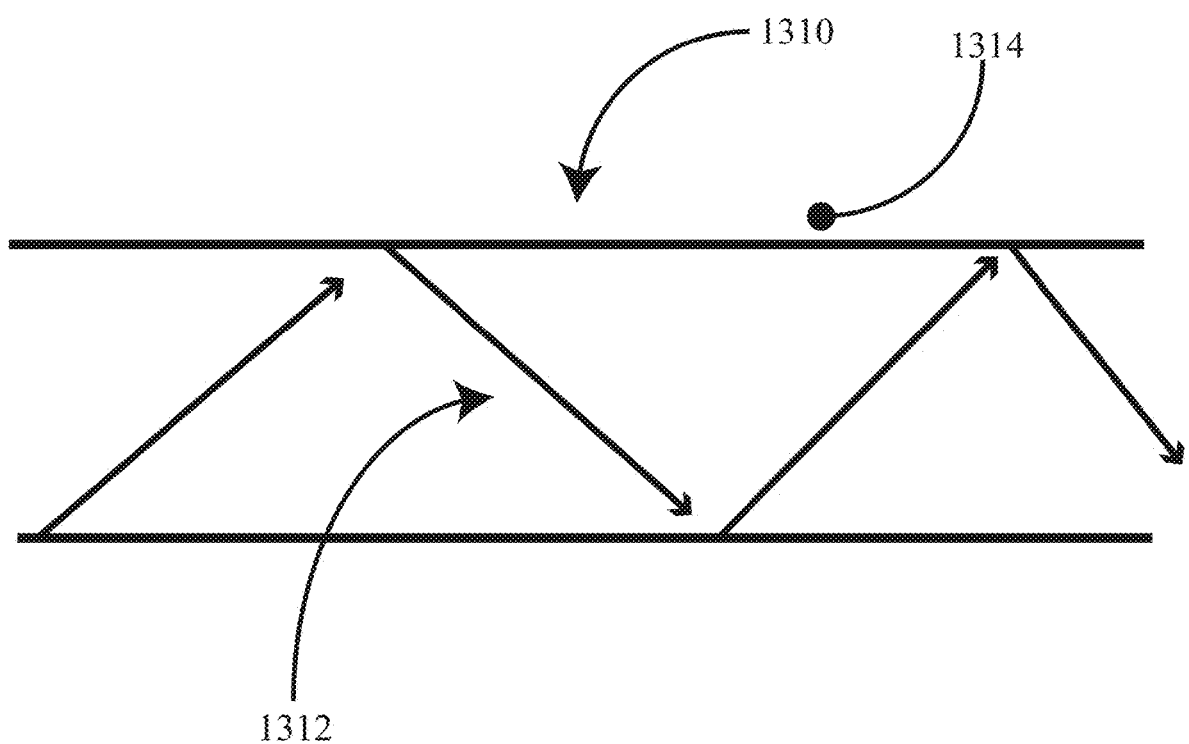
FIG. 13A illustrates internal reflection within an optic, in accordance with one embodiment.
Figure 13B:
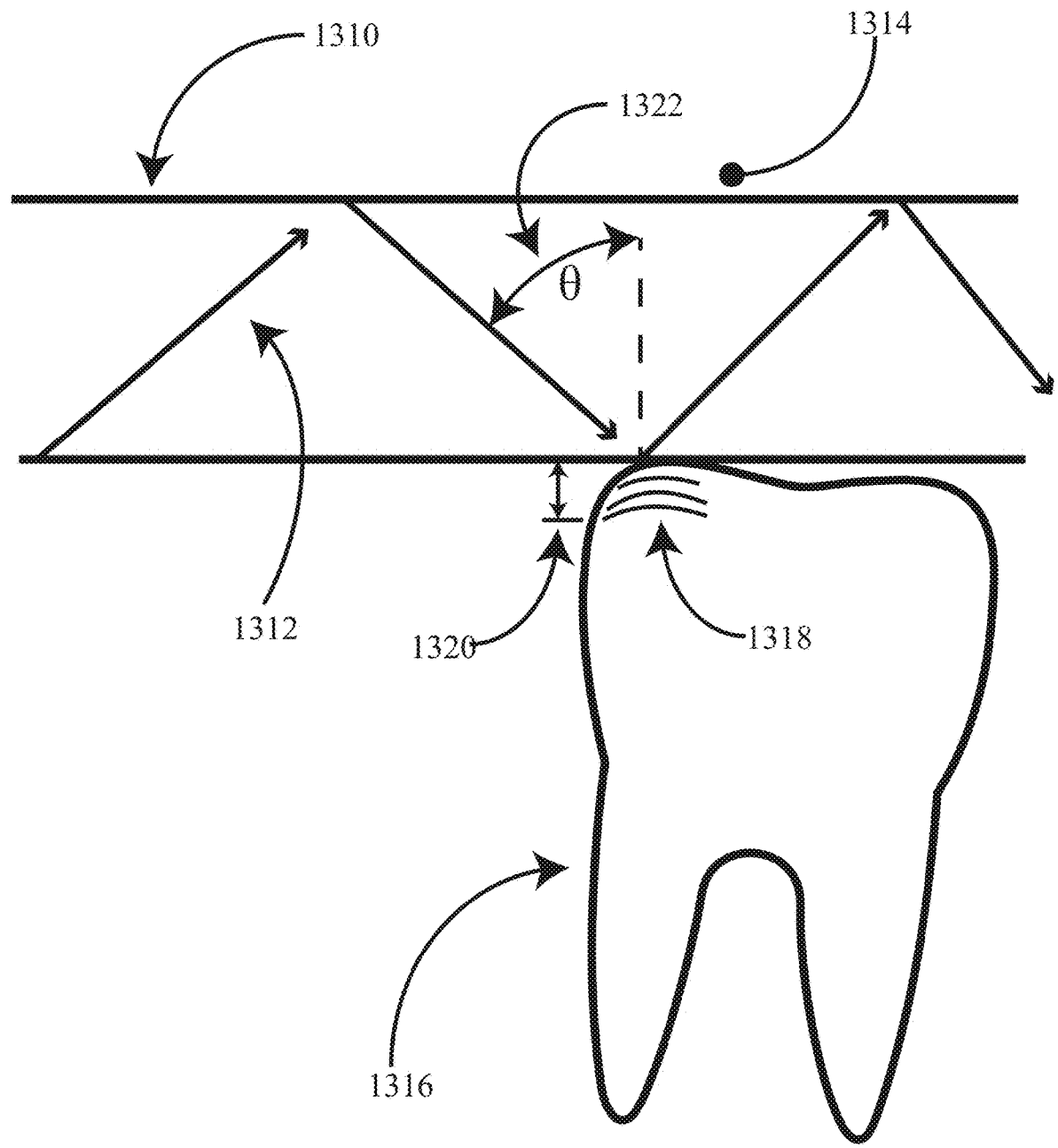
FIG. 13B illustrates a first technique for contact coupled irradiation of dental hard tissue, in accordance with one embodiment.
Figure 13C:
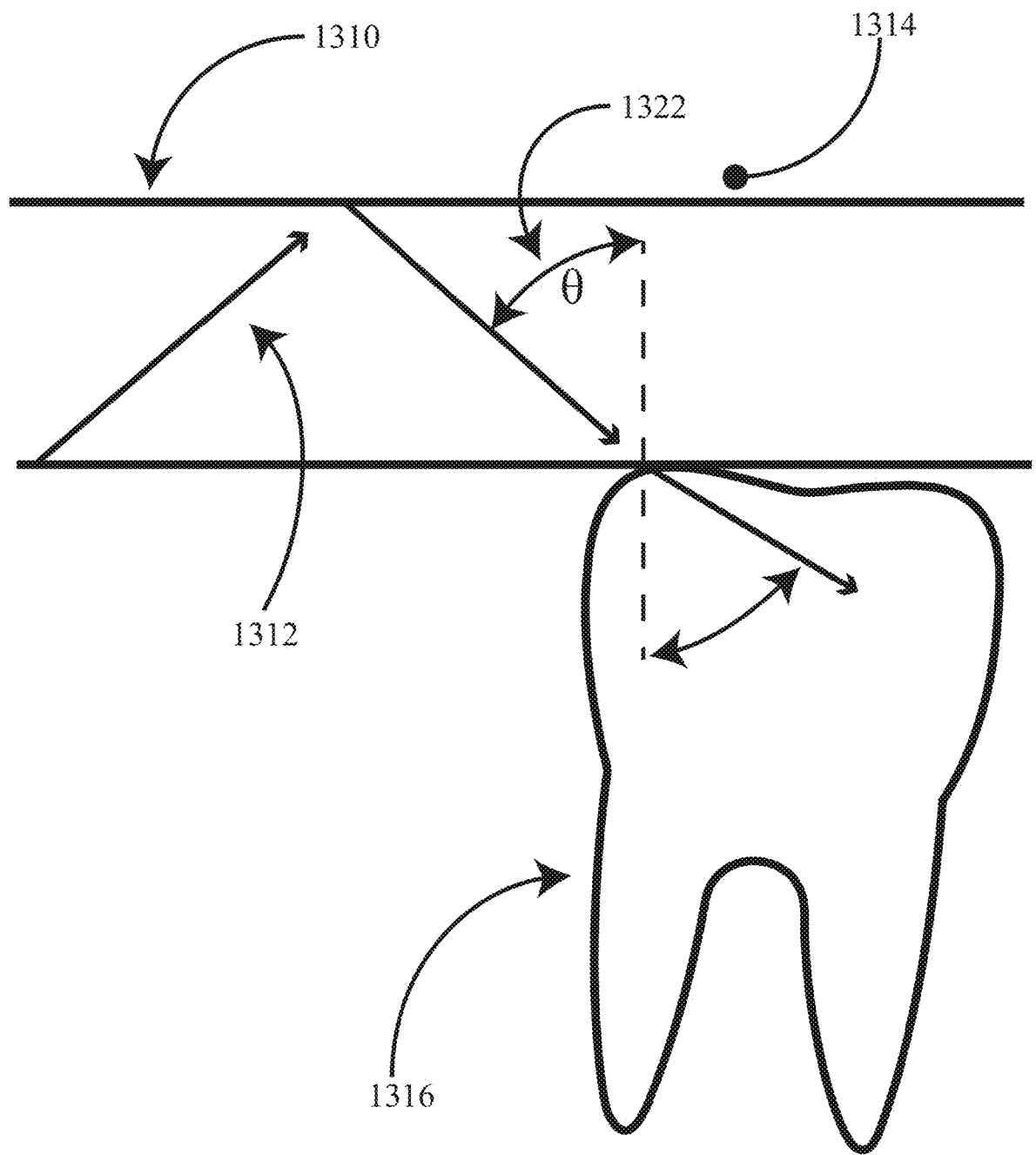
FIG. 13C illustrates a second technique for contact coupled irradiation of dental hard tissue, in accordance with one embodiment.

Referring to FIGS. 13A-C, in some embodiments, an optic (e.g., waveguide) 1310 contacts a dental hard tissue in order to transmit radiation 1312. FIG. 13A schematically illustrates a radiation 1312 propagating through the optic 1310. A medium 1314 surrounding the optic 1310 in FIG. 13A is air. Air has an index of refraction of one (1.0); and, the optic typically has an index of refraction greater than one. Generally speaking, because the surrounding medium 1314 has a lower index of refraction than that of the optic 1310, the radiation 1312 experiences internal reflection (e.g., total internal reflection [TIR]) within the optic 1310.

FIG. 13B schematically represents a first technique for contact coupling radiation 1312 into dental hard tissue 1316. In the first technique, the optic 1310 has an index of refraction that is greater than the index of refraction of the dental hard tissue. For example, in some exemplary embodiments a high index optic material is used (e.g., diamond [n=2.38], ZnSe [n=2.61], or ZnS [n=2.37]) and index of refraction for dental enamel is about 1.6. In this case, radiation 1312 reflected at an interface between the optic 1310 and the dental hard tissue 1316 experiences attenuated internal reflection (e.g., attenuated total internal reflection [ATIR]). An evanescent wave 1318 (i.e., evanescent field) comprising a portion of the radiation is formed, which penetrates the dental hard tissue 1316. The evanescent wave 1318 penetrates a certain depth 1320 into the dental hard tissue. The depth 1320 of the evanescent wave 1318 penetration can be approximated using a relationship:

$$d = \frac{\lambda_0}{2\pi\sqrt{n_1^2 \sin\theta^2 - n_2^2}}$$

where, d is penetration depth 1320 of the evanescent wave 1318; $\lambda_0$ is vacuum wavelength of the radiation 1312; $n_1$ is index of refraction of optic 1310; $n_2$ is index of refraction of material surrounding the optic (e.g., the dental hard tissue 1316 or the air 1314); and, θ is an angle of incidence 1322 of the radiation 1312 at the interface. Under conditions of total internal reflection (TIR), the angle of incidence 1322 has a value which is greater than a critical angle. The critical angle can be approximated by using a relationship:

$$\theta_{critical} = \sin^{-1}\frac{n_2}{n_1}$$

where, $\theta_{critical}$ is the critical angle, mi is index of refraction of the optic 1310, and $n_2$ is index of refraction of the material surrounding the optic (e.g., air 1314 or dental hard tissue 1316).

For example, in a certain exemplary embodiment the optic comprises CVD diamond, having an index of refraction of approximately 2.38 and the laser source comprises a $CO_2$ laser, having a wavelength of 9.3 µm. In this case, the critical angle for TIR between the CVD diamond and the dental enamel is approximately 42° and a maximum penetration depth 1320 of the evanescent wave using an angle of incidence slightly greater than the critical angle (e.g., 43°) is 5 µm. As optical penetration depth (due to absorption) of 9.3 µm radiation in dental enamel (i.e., hydroxyapatite) (e.g., ~2 µm) is less than the evanescent wave penetration depth 1320, much of the radiation 1312 will be absorbed into the dental hard tissue 1316 under these conditions.

FIG. 13C schematically represents a second technique for contact coupling radiation 1312 into dental hard tissue 1316. In the second technique, radiation 1312 is refracted into the dental hard tissue 1316. This phenomenon is sometimes understood as frustrated internal reflection (e.g., frustrated total internal reflection [FTIR]). In one embodiment of the second technique, the optic 1310 has an index of refraction that is less than the index of refraction of the dental hard tissue. For example, in some exemplary embodiments a lower index optic material is used (e.g., UV fused silica [n=1.5]) and index of refraction for dental enamel is about 1.6. In this case, radiation 1312 is refracted into the dental hard tissue 1316.

For example, a certain exemplary embodiment employs a UV laser source having a 355 nm wavelength and a fused silica optic having an index of refraction of 1.5. In this case, the critical angle for the optic 1310 using air (n=1) as the surrounding material is about 42° and evanescent field penetration 1322 within air at the optic boundary using an angle slightly greater (43°) than the critical angle is approximately 0.3 µm. However, when the optic 1310 comes in contact with the dental hard tissue 1316, the radiation 1312 is refracted into the dental hard tissue, in a manner that can be understood according to Snell's law, and absorbed by the dental hard tissue. In some circumstances, the case of a UV laser source (355 nm) and a fused silica optic (n=1.5) is additionally advantageous. This is because UV light can cause genetic damage, which can cause cancer (e.g., skin cancer). For this reason, application of UV radiation should be precisely directed only to dental hard tissue and not to soft tissue (e.g., skin and mucosa). The UV radiation will undergo TIR reflection within the optic when surrounded by air and therefore stay confined within the optic and not directed to tissue not in contact with the optic 1310. Additionally, under some cases the UV light will not fully couple out of the optic 1310 even when placed in contact with oral soft tissue. Oral soft tissue has an index of refraction (at UV wavelengths) that is near that of water and is typically less than that of fused silica, (e.g., 1.4). For example, a representative critical angle for total internal reflection between soft tissue and a fused silica optic 1310 is 69° and a maximum evanescent wave penetration depth 1322 for a 355 nm beam with a 70° angle of incidence is approximately 0.3 µm. A cell width is approximately 10 to 30 µm. Therefore, the UV radiation does not penetrate cell nuclei; and, a likelihood of genetic damage to the soft tissue is greatly reduced, even when the optic is placed in direct contact with soft tissue.

In one embodiment, the second technique as outlined in FIG. 13C and described as frustrated internal reflection can also occur when the index of refraction of the dental hard tissue is less than that of the optic 1310. Frustrated internal reflection also occurs where the angle of incidence is smaller than the critical angle between the index of refraction for the optic 1310 and the dental hard tissue 1316. For example, returning to the example above with a 9.3 µm radiation 1312 and a CVD diamond optic 1310 with an index of refraction of 2.38, a critical angle between the optic and air is about 25°, a critical angle between the optic and oral soft tissue is about 36°, and a critical angle between the optic 1310 and the hard tissue 1316 is about 42°. This means that radiation propagating at an angle of incidence between 36° and 42° will experience total internal reflection (TIR) when the optic 1310 is in air or in contact with oral soft tissue and frustrated total internal reflection (FTIR) when the optic 1310 is placed in contact with dental hard tissue 1316. Tissue specific penetration of radiation is therefore an advantage of certain embodiments, although addition advantages do exist. For example, use of a contacting laser delivery device is expected to be more easily adapted to use in a dental operatory, where most dental tools are used in contact with dental hard tissue.

Figure 14:
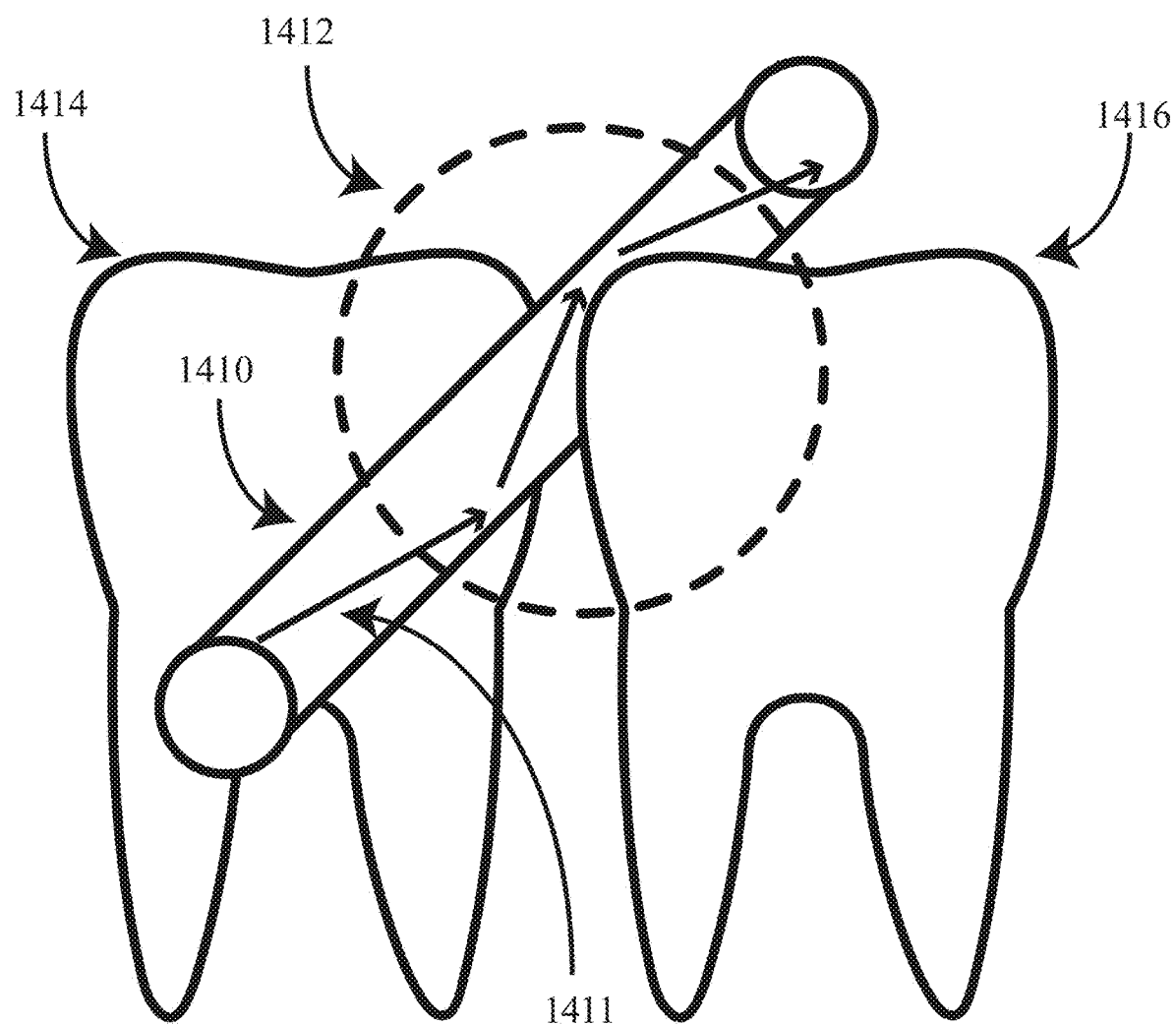
FIG. 14 illustrates a system for preventative inter-proximal dental treatment, in accordance with one embodiment.

Another advantage of certain embodiments is that contact coupling of radiation can be used to treat areas of dental hard tissue that a conventional free space laser treatment cannot. For example, inter-proximal dental regions (i.e., space between the teeth) are common locations for caries formation and a location that convention lasers cannot always irradiate, as there is no free space direct line of sight of the inter-proximal regions. In certain exemplary embodiments, an optic 1410 is configured to access and deliver radiation 1411 to inter-proximal dental hard tissue 1412. FIG. 14 schematically illustrates an optic 1410 between a first tooth 1414 and a second tooth 1414. In some embodiments, the optic 1410 comprises a rod having a diameter (e.g., less than 2 mm, less than 1 mm, or less than 0.5 mm) selected to fit inter-proximally between teeth. In some embodiments, the rod comprises a hard material (e.g., diamond or quartz) so that it does not break during use.

Figure 15:
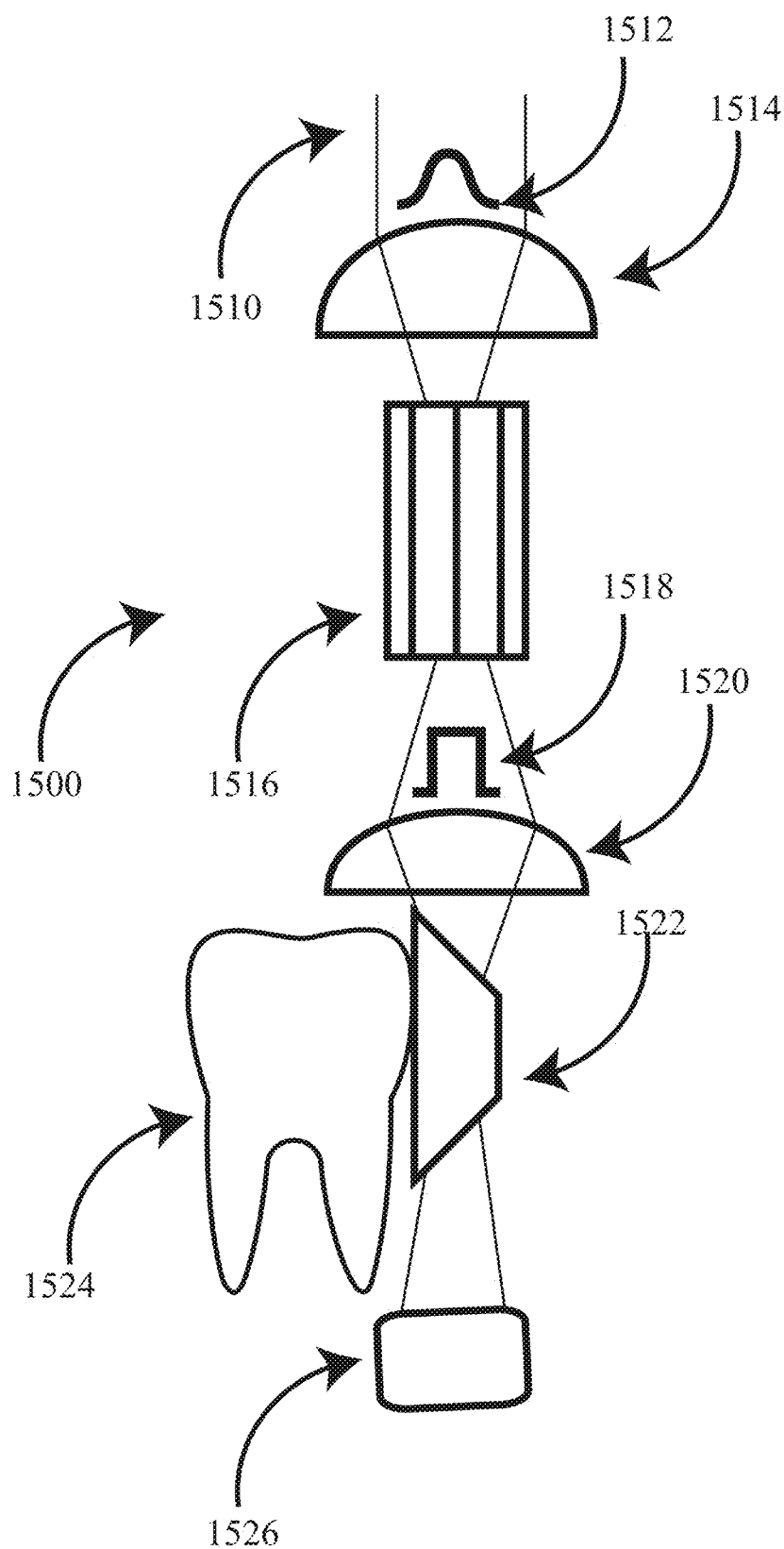
FIG. 15 illustrates a system for cooling an optic contacting dental hard tissue, in accordance with one embodiment.

FIG. 15 illustrates an optical path 1500, in accordance with an embodiment. A collimated radiation, for example a laser beam 1510, having a Gaussian energy profile 1512 is directed incident a first focus optic 1514. The first focus optic 1514 converges the radiation and directs the radiation into a homogenizer 1516. Exemplary homogenizers include diffractive optical element (DOE) homogenizers, transmissive diffusers, reflective diffusers, and rod homogenizers. An exemplary DOE homogenizer for infrared wavelengths is Part No. HM-212-A-Y-A from Holo/OR of Ness Ziona, Israel. An exemplary rod homogenizer for UV wavelengths is a 2 mm clear aperture fused silica homogenizing rod, Edmund Optics Part No. 63-092 from Edmund Optics of Barrington, New Jersey, U.S.A. Typically, the radiation 1510 diverges as it exits the homogenizer. After exiting the homogenizer 1516, the radiation has a more homogenized energy profile (e.g., flat-top, top-hat, or super-Gaussian) 1518. A second focus optic 1520 converges the radiation 1510 again and directs it into a coupling optic 1522. Exemplary coupling optics 1522 include prisms, dove prisms, waveguides, rods, ATR prisms, etc. An exemplary dove prism is a 10 mm dove prism Part No. 85-156 from Edmund Optics. According to some embodiments, the optical path 1500 also comprises a waveguide or fiber optic. An exemplary prism assembly that additionally comprises a fiber optic is Diamond Probe, Part No. DMP-PRB from Harrick Scientific Products of Pleasantville, New York, U.S.A. Radiation is at least partially transmitted into a dental hard tissue 15624 when it is placed in contact with the coupling optic 1522. Finally, the radiation 1510 not transmitted into the dental hard tissue exits the coupling optic 1522 and is directed toward either a sensor or a beam dump 1526. Irradiative treatment of the dental hard tissue 1524 raises the temperature of the surface of the dental hard tissue to an elevated temperature (e.g., between 400° C. and 1200° C.) momentarily. For this reason, the coupling optic in some embodiments is constructed from a material that can handle these high temperatures (e.g., diamond, sapphire, fused silica, and quartz). Alternatively, in some embodiments, the coupling optic is consumed during each treatment and the material is inexpensively produced, for example optical salts (e.g., barium fluoride, magnesium fluoride, and calcium fluoride).

Figure 16:
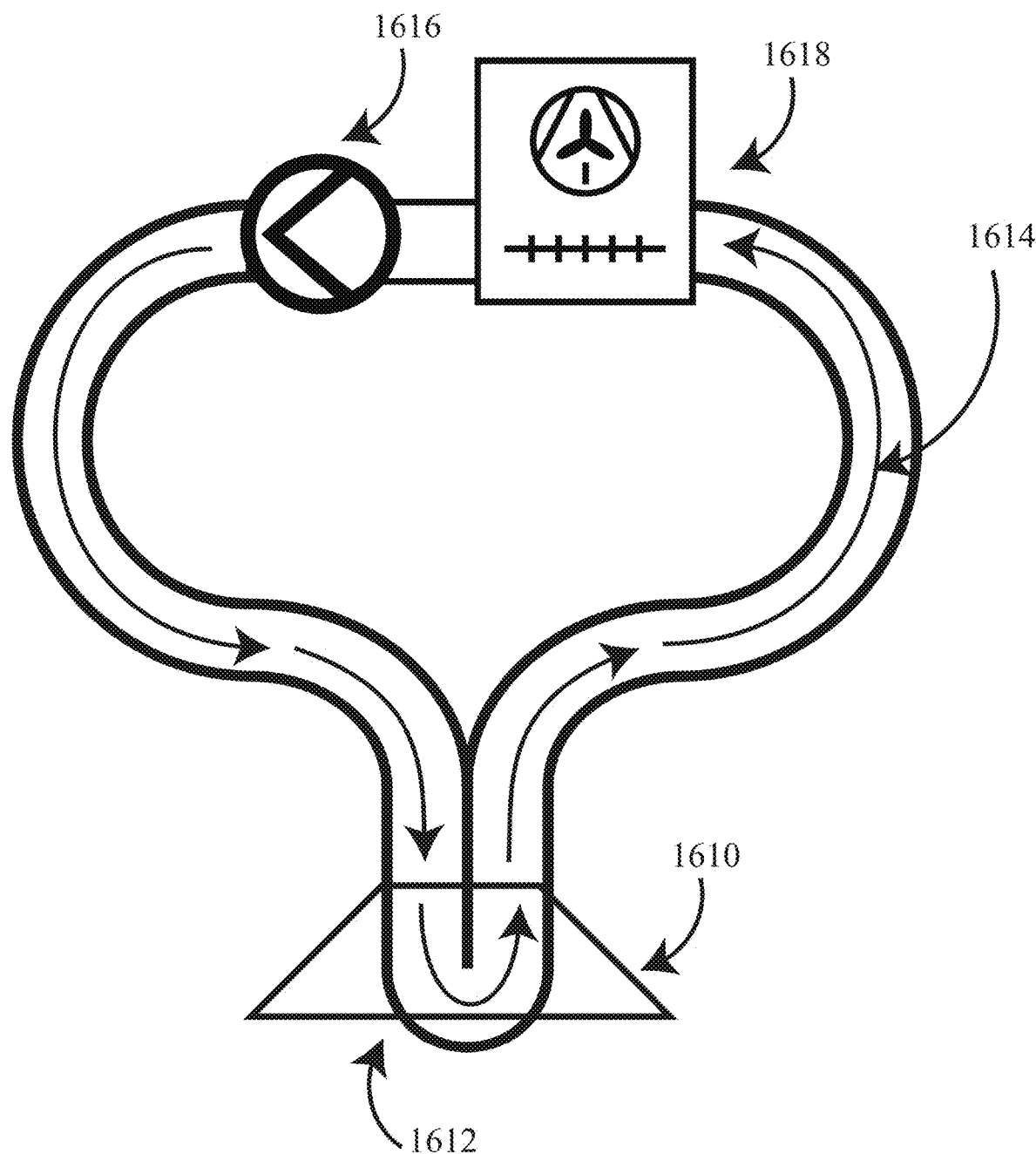
FIG. 16 illustrates a system for homogenizing a radiation, in accordance with one embodiment.

Additionally, in some certain exemplary embodiments, the coupling optic is actively cooled to prevent bulk heating of the dental hard tissue (e.g., tooth) and/or the optic itself. It is widely accepted that in order to prevent the possibility of thermal damage to a tooth, nerves within a pulpal chamber of the tooth must not be raised to a temperature greater than 5.5° C. above normal. Delivering irradiative energy to the tooth can result in bulk heating of the tooth. In order to prevent thermal damage, in some embodiments, contact cooling of the tooth is achieved by way of cooling the coupling optic. FIG. 16 illustrates an embodiment in which a cooling system 1600 cools a coupling optic 1610. The coupling optic 1610 is at least partially enclosed within a fluidic pathway through which a coolant 1614 flows. In some cases, the fluidic pathway provides a seal about the coupling optic, such that the coolant can come in direct contact with the coupling optic 1610. Alternatively, the fluidic pathway 1612 is entirely separate from the coupling optic 1610, such that the coolant cools the fluidic pathway 1612 and then the fluidic pathway 1612 cools the coupling optic 1610. The coolant 1614 circulates within the fluidic pathway 1612 using a pump 1616. The coolant is cooled by a chiller 1618. Exemplary chillers include Peltier junctions. The coolant 1614 is chilled to a temperature that is low enough to prevent bulk heating of the dental hard tissue (e.g., tooth) and not too low to cause discomfort for the patient (e.g., in a range between −20° C. to 20° C.).

Although, exemplary systems disclosed above describe use of a laser source to deliver radiation for treatment, non-laser-based systems are envisioned. For example, in some embodiments, radiation is non-coherent. The non-coherent radiation in some cases is generated by a non-coherent light source, for example a flash lamp. In a certain specific exemplary embodiment, UV non-coherent radiation is generated by one or more of a Xeon flash lamp, a Xeon lamp, a Mercury-Xeon lamp, and a Deuterium flash lamp.

Recurrent Payment to Defray Laser System Ownership Costs

In order to minimize upfront costs associated with installation of a dental laser system, a distribution system is disclosed that allows for the secure distribution of coupons representative of individual (or multiple) uses of the dental laser system, thus achieving a recurrent payment system. Additionally, systems and methods are disclosed to ensure that unauthorized use of the dental laser system is minimized. In order to successfully minimize unauthorized use, techniques are employed that result in a cost associated with circumventing authorized use (e.g., through counterfeiting, hacking, or fraud) exceeding a cost associated with purchasing authentic coupons. Said another way, in a commercially successful practice of the disclosed distribution system and methods, a price of the coupons (representing a single use of the laser system) is interrelated with a level of technological difficulty to circumvent the coupons. Description of systems and methods that support making, distributing, and using these coupons are described below.

Figure 17A:
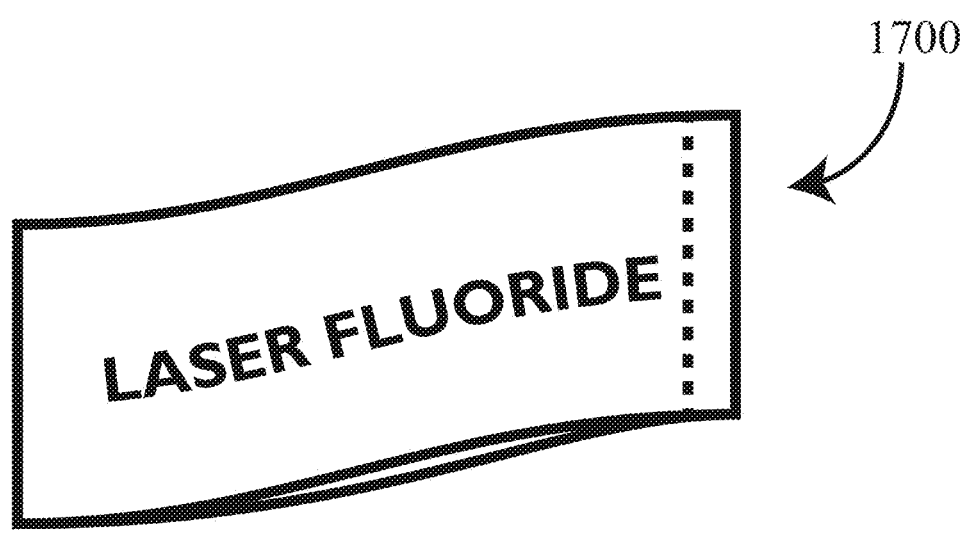
FIG. 17A illustrates a package containing consumables for a preventative dental laser treatment, in accordance with one embodiment.

FIG. 17A illustrates a distribution system for preventative laser and fluoride treatment in accordance with one embodiment. A hermetically sealed package 1700 is shown in FIG. 17A fully intact. This package is distributed to dental practices like other dental supplies (e.g., consumables). In many embodiments, many units of the package 1700 are grouped together and distributed to dental practices in multipacks (e.g., cases).

Figure 17B:
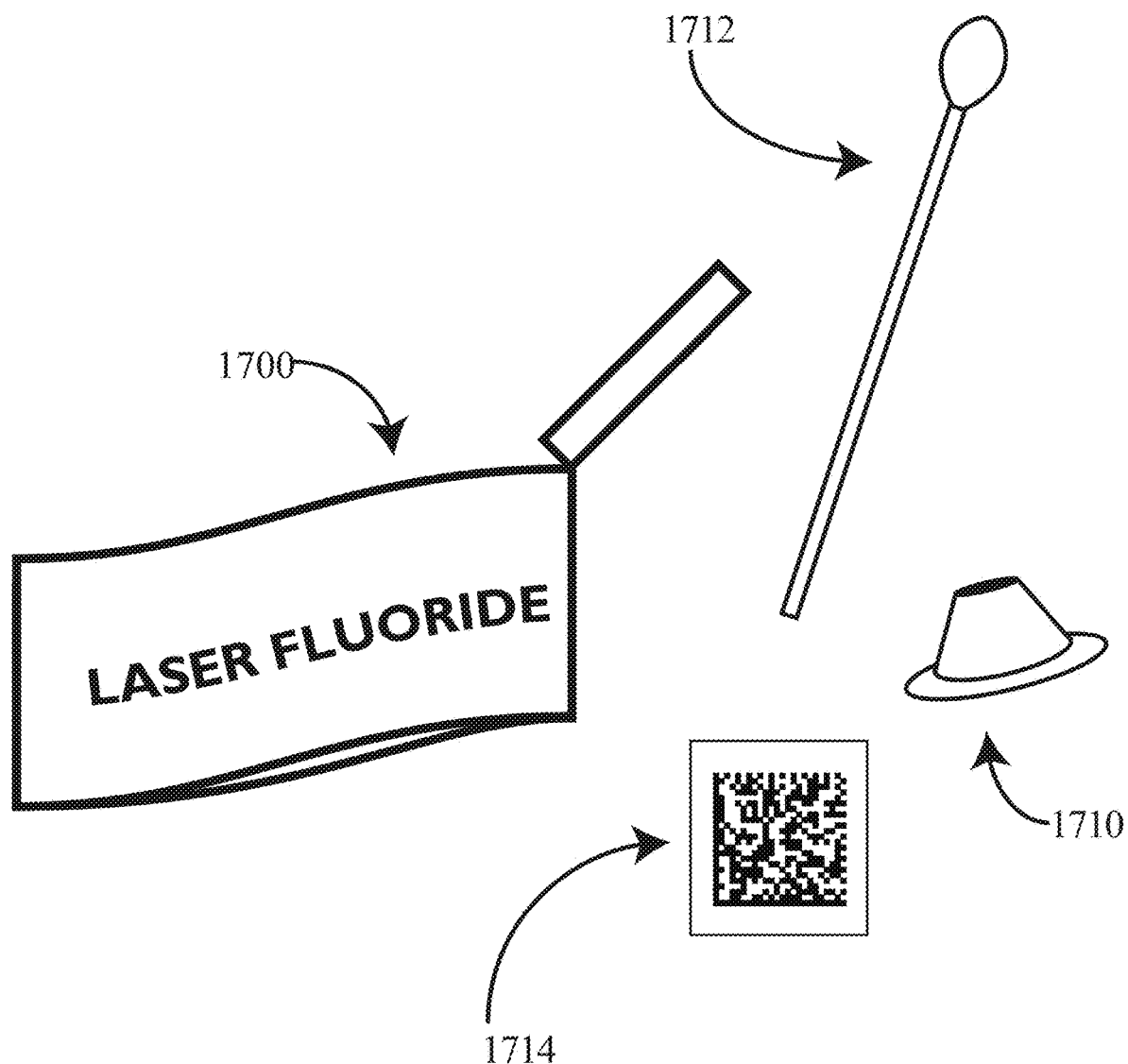
FIG. 17B illustrates an opened package containing consumables for preventative dental laser treatment, in accordance with one embodiment.

FIG. 17B illustrates the package 1070 after being opened. In accordance with one embodiment, the package contains a fluoride treatment dosage 1710, a fluoride applicator 1712, and a machine-readable code 1714. Exemplary fluoride dosages 1710 include fluoride varnishes, fluoride gels, fluoride pastes, fluoride fluids, and fluoride foams. The fluoride dosage 1710 comprises any number of fluoride compositions known to effectively treat dental surfaces, for example Sodium Fluoride (NaF) and Stannous Fluoride ($SnF_2$). Exemplary applicators 1712 include swabs, needles, syringes, and dental trays (not shown). The machine-readable code 1714 is configured to be read by the dental laser system. In one embodiment, the machine-readable code 1714 represents one (or more) dental laser treatment(s). Exemplary forms of the machine-readable code 1714 include a barcode, a 2D barcode, a magnetic strip (not shown), a transponder device (not shown), a microchip (not shown), and a radio-frequency identification (RFID) tag (not shown). Typically, the machine-readable code 1714 represents a coupon for one or more laser treatments and without a valid coupon (or number of coupons) the laser treatment cannot be performed.

Figure 18A:
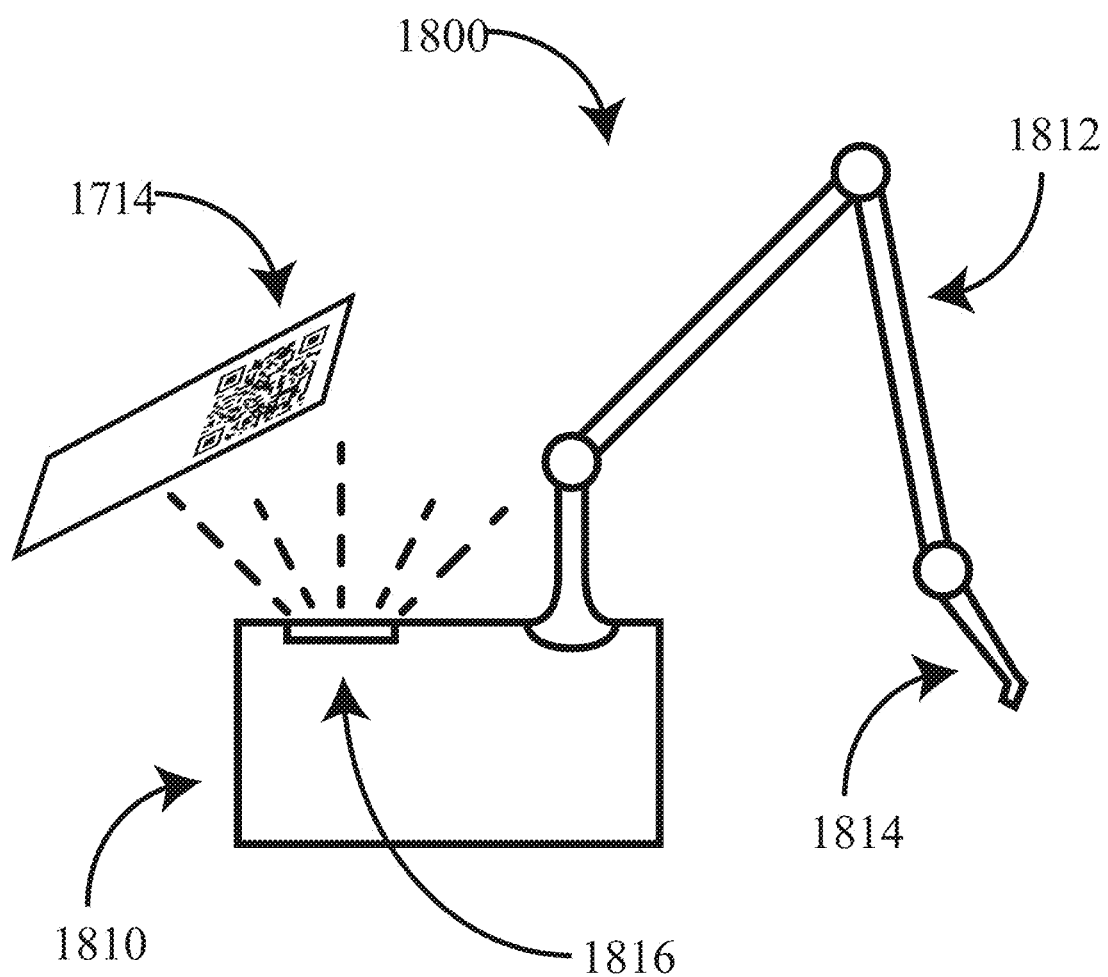
FIG. 18A illustrates a system for performing a preventative dental laser treatment, in accordance with one embodiment.

FIG. 18A illustrates a preventative dental laser system 1800 in accordance with one embodiment. The dental laser system 1800 typically includes a console 1810. Within the console 1810 a laser source and a laser controller are housed. An exemplary laser source is a carbon dioxide ($CO_2$) laser, for example HPP DL-500 from Access Laser of Everett, Washington, U.S.A. Additional exemplary laser sources include carbon dioxide ($CO_2$) lasers, carbon monoxide (CO) lasers, excimer lasers, fiber lasers, diode pumped solid state (DPSS) lasers, and semiconductor lasers. Typically, the radiation source is selected to generate a radiation 1710 having a wavelength that is well absorbed (e.g., has an absorption coefficient greater than 1 $cm^{-1}$, 100 $cm^{-1}$, or 1,000 $cm^{-1}$) by the dental hard tissue 1712. Exemplary wavelengths include wavelengths in either of a first range between 200 and 500 nm and second range between 4 and 12 μm. The laser source generates a laser beam, which is directed via a beam delivery system 1812 to a hand piece 1814. Exemplary beam delivery systems 1812 include articulated arms, hollow waveguides, and fiber optics. The hand piece 1814 is configured to be used intra-orally to deliver the laser beam to surfaces of dental hard tissue for treatment. The laser controller is configured to control at least one parameter of the laser beam during treatment. Exemplary laser parameters include pulse energy, average power, peak power, pulse duration, and repetition rate.

The laser system 1800 also includes a code reader 1816, which is configured to read the machine-readable bar code 1714. In one embodiment, the code reader 1816 employs a machine vision system, which takes a digital image of the machine-readable code 1714 and recognizes the machine-readable code 1714. In some cases, the machine vision system includes a lens assembly, an optical sensor (e.g., a charge-coupled device [CCD] or a complementary metal-oxide semiconductor [CMOS]), and a vision processor. The vision processor is configured to recognize a code within the digital image of the machine-readable code 1714. Exemplary software resources for reading the machine-readable code in a digital image include Data Matrix within OpenCV project. Alternatively, the machine-readable code 1714 can be stored on another device, for example a one-wire chip, an RFID tag, a film, and a magnetic strip. So, in alternative embodiments, the code reader 1816 comprises one or more of a one-wire chip reader (not shown), an RFID tag reader (not shown), a film reader (e.g., camera with illumination system), and a magnetic stripe reader (not shown). In order for the machine-readable code 1714 to successfully prevent fraudulent use of the laser system 1800, the code 1714 is verified.

Figure 18B:
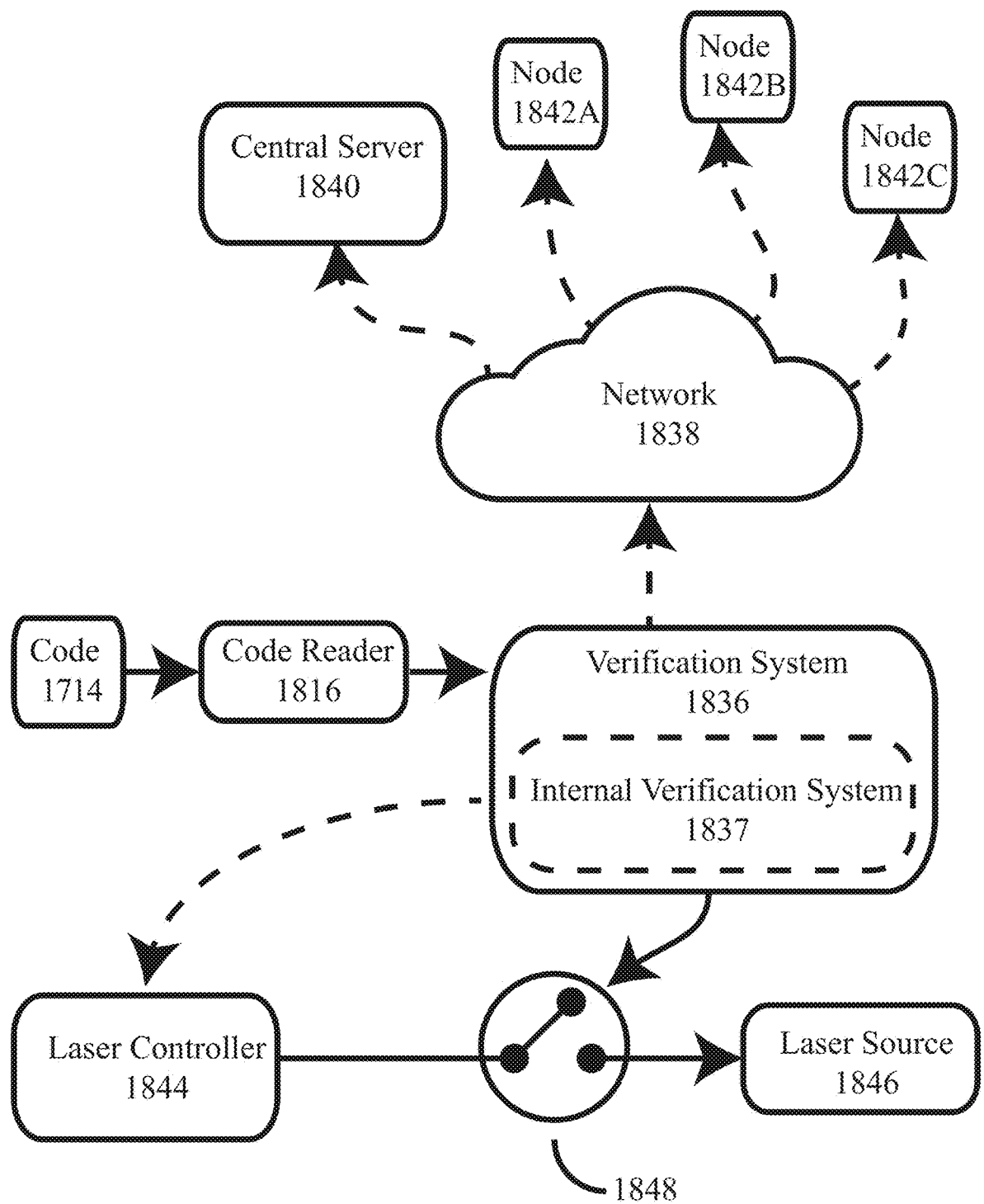
FIG. 18B illustrates a system for coupon verification, in accordance with one embodiment.

A verification system 1836, in accordance with one embodiment, is illustrated in a block diagram in FIG. 18B. A code 1714 is first read by a code reader 1816. The code reader 1816 recognizes the code and communicates the code to the verification system 1836. The verification system typically comprises a processor that is local to the dental laser system 1800. In some cases, the verification system employs an internal verification system 1837 only, which verifies the code locally. For example, in accordance with one embodiment a one-wire authentication chip and only an internal verification system 1837 is used. In an alternative embodiment, the code 1714 comprises a digital signature (e.g., cryptocurrency) that exists within memory (e.g., non-volatile memory) and the code reader comprises a processor. In some situations, the code 1714 is verified by way of remote systems.

The verification system 1836 can use one or more networks 1838. Exemplary networks include local area networks (LAN), wide area networks (WAN), wireless networks (WiFi), closed area networks (CAN), etc. In accordance with one embodiment, the verification system communicates the code 1714 with a central server 1840 by way of one or more networks 1838. In some cases, communication between the verification system 1836 and the server 1840 is encrypted (e.g., symmetric encryption or public key/private key encryption). In some cases, the verification system 1836 includes additional information in its communication with the central server 1840, for example a timestamp, a unique system identifier, or information regarding the laser treatment. The central server 1840 then compares the information as communicated from the verification system 1836 and determines an authenticity of the code 1714 and determines if the code 1714 is valid (e.g., has not been used before). Once the central server 1840 and the verification system 1836 verify the code, the verification system 1836 allows a laser treatment to be performed. In alternative embodiments, the determination performed in part by the central server is performed using one or more nodes 1842A-C. The nodes 1842A-C, in accordance with one embodiment, are communicated to by the verification system 1836 and are queried to learn if the code 1714 is authentic and unused. In some cases, a majority of node responses are used to verify the code and conflicts between nodes are satisfied in accordance with the principle of "proof of work" (for example, with a blockchain method). In some embodiments, each laser treatment system 1800 comprises a verification node.

Generally, the verification system 1836 only allows the laser controller 1844 to operate the laser source 1846 after the machine-readable code 1714 has been verified. In some cases, the verification system 1836 budgets a use of the treatment system 1800. Certain exemplary budgets are for one treatment, a certain amount of time, a certain amount of laser energy delivered, or a certain amount of energy consumption by the laser. In some cases, an interlock 1848 is closed by the verification system 1836 post-verification to permit a budgeted use. The verification system 1836 in some case communicates directly with (or is coupled to) the laser controller 1844 in order to prevent a simple defeat of the interlock 1848, which would allow a circumvention of the verification system 1836 (and an unbudgeted use). For example, in a certain embodiment, the laser controller 1844 comprises a field programmable gate-array (FPG) (e.g., Xilinx Zynq) and the verification system 1836 comprises a one-wire authentication system (e.g., MAXREFDES44 #reference design from Maxim Integrated of San Jose, California, U.S.A.) to verify the machine-readable code and communicate directly with the laser controller 1844.

After verification (or simultaneously with verification, or prior to verification), the verification system 1836 also prevents future verification of the same code 1714. In one embodiment, prevention of future validation is achieved by submitting to the central server 1840 or one or more nodes 1842A-C that the machine-readable code 1714 is no longer valid. In one embodiment, preventing future verification of the machine-readable code 1714 entails deleting, destroying, disrupting, voiding, or overwriting the machine-readable code 1714. For example, in some cases the machine-readable code 1714 is contained within a one-wire authentication chip and during reading of the chip, the machine-readable code is overwritten, for example to zero. Although many techniques are described to allow use of the system only after verification of the code 1714, unauthorized use of the system 1800 is always a technically feasible possibility. Certain exemplary attacks that could be used to circumvent the verification system 1836 include "man-in-the-middle," "replay attack," and "chip rip." As each coupon needs to be relatively cheap to produce (e.g., much less than a cost to perform one treatment), not all potential attacks can be realistically redressed. For this reason, further systems are employed, in some embodiments, to monitor system use.

Figure 18C:
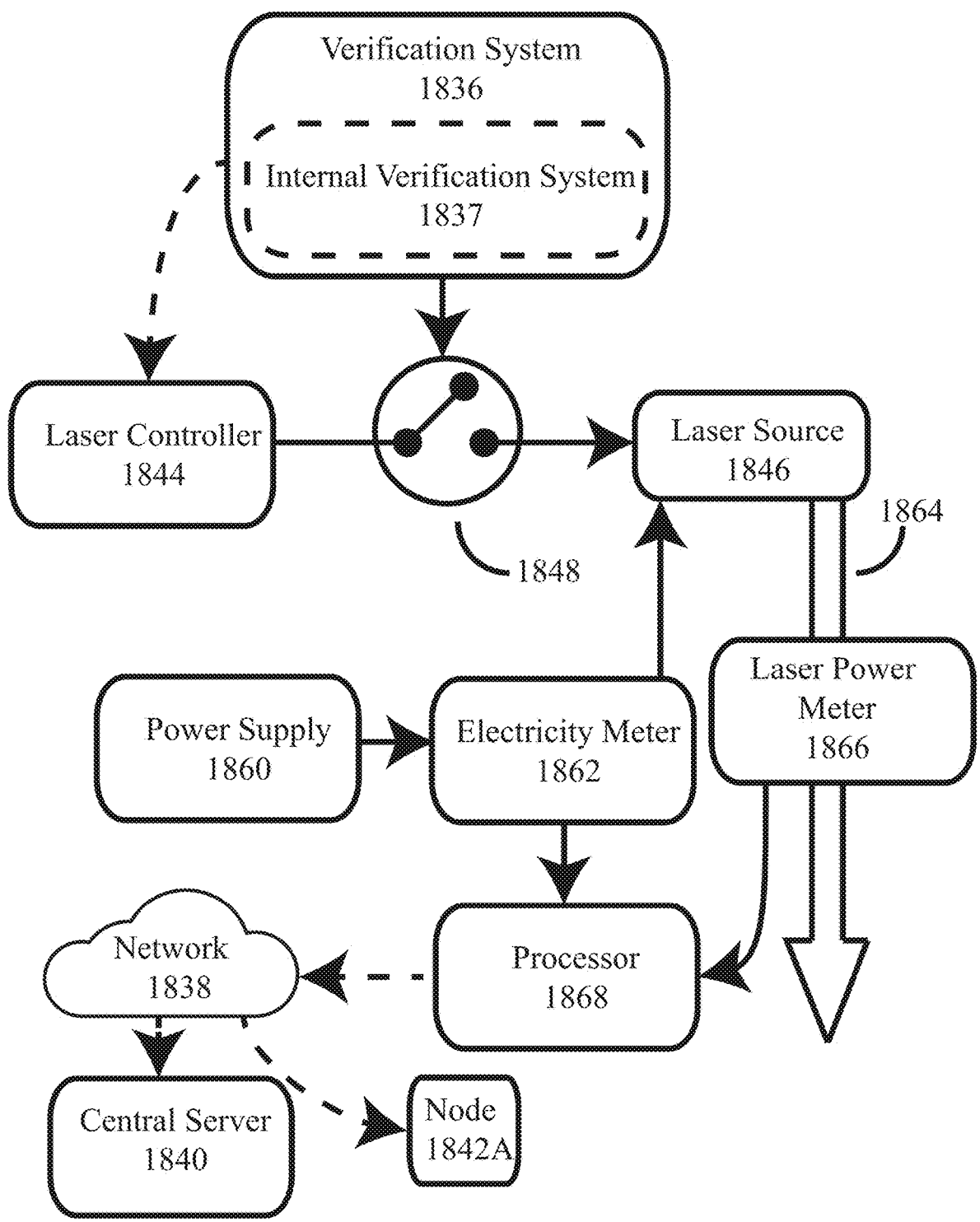
FIG. 18C illustrates a block diagram of exemplary additional subsystems of an exemplary dental laser system, in accordance with one embodiment.

FIG. 18C illustrates a block diagram of additional subsystems of the dental laser system 1800, in accordance with one embodiment. A power supply (e.g., direct current [DC] power supply) 1860 powers the laser source 1846. Located schematically between the power supply 1860 and the laser source 1846 is an electricity meter 1862. The electricity meter 1862, in some embodiments, measures an amount of electricity (e.g., energy [power multiplied by time]) that is consumed by the laser source 1846. The measured electrical energy is an indication of laser on-time and therefore use of the laser treatment system 1800. The laser source 1846 generates a laser beam 1864 during laser treatment. In accordance with one embodiment, the laser beam is continuously monitored by a laser power meter 1866 (e.g., thermopile or photodetector). In some cases, a small proportion of the total laser beam 1864 is "picked-off." The small proportion of the laser beam is then measured as representative of the total laser beam energy by the laser power meter 1866. In some cases, the measured value from the laser power meter 1866 is used as another indication of laser on-time and therefore laser treatment system use.

A processor receives the measurements form one or both of the electricity meter 1862 and the laser meter 1866. The processor in some embodiments, logs the measurements, for example, either locally, or on the central server 1840 and/or a de-centralized node 1842A by way of one or more networks 1838. Logging measurements that are indicative of use allows for an understanding of actual treatment system use time to be estimated. The estimated actual system use time can later be compared with verified use (e.g., number of verified coupons). Just as discrepancies in exit-polling and vote count indicate voter-fraud, discrepancies between estimated actual system use and verified system use (e.g., coupon use count) indicate fraudulent use of the laser system.

FIG. 19 is a flow chart 1900, which illustrates a method for preventative dental treatment, in accordance with one embodiment. First, a machine-readable code is read 1910. In some embodiments, the machine-readable code represents a coupon for one (or more) laser treatments. In some embodiments, the machine-readable code is read by a barcode reader. Alternatively, the machine-readable code is read by one or more of: a magnetic stripe reader, a radio-frequency identification (RFID) reader, a transponder reader, and a microchip interface (e.g., a one-wire device). The machine-readable code is read 1910 and then the machine-readable code is verified 1912. In some cases, the machine-readable code is verified by determining its inclusion in a list of verifiable machine-readable codes. In one embodiment, the machine-readable code is encrypted, for example by using one or more of a symmetric encryption system and an asymmetric encryption method, and verification of the machine-readable code includes decryption. In some cases, the machine-readable code is verified remotely (e.g., over a network), for example by a central server or one or more nodes. In some cases, communication over the network (during verification) is further encrypted between a verification system local to the treatment system and the central server or one or more nodes. In some cases, the central server and one or more decentralized nodes comprise ledgers (e.g., decentralized ledger). The decentralized ledgers are used to track issuance, verification, transfer, and use of coupons. In some cases, decentralized ledgers that demonstrate the greatest amount of computational work are trusted over contradicting decentralized ledgers that demonstrate achieving less computational work. A certain exemplary system for decentralized ("trustless") ledgers is a blockchain. In some embodiments, digital signatures related to individual treatment systems are used to ensure additions to the ledger(s) are honest. For example, in some cases a private key associated with an individual treatment system is used to encrypt a digital signature, which is used in one or more ledgers. In some embodiments, the digital signature sent from an individual treatment system also includes additional information that can aid in verification of honest use of coupons.

Once, the machine-readable code is verified (for example, verified as an unspent and otherwise valid coupon representing a laser treatment and/or agreed by one or more ledgers that the system verifying has a coupon to use), a laser treatment is budgeted for by the system and a laser treatment is performed 1914. A laser treatment is represented in accordance with one embodiment in FIG. 19.

Firstly, the laser treatment begins by generating a laser beam 1914A. The laser beam is typically generated using a laser source. Exemplary laser sources include: $CO_2$ lasers having a wavelength between 9 µm and 11 µm, fiber lasers, diode pumped solid state lasers (DPSS), Q-switched solid-state lasers (e.g., third harmonic Nd: YAG lasers having a wavelength of about 355 nm), Excimer lasers, and diode lasers. Commonly the laser beam has a wavelength that is well absorbed (e.g., has a wavelength having an absorption coefficient greater than 1 $cm^{-1}$, 100 $cm^{-1}$, or 1,000 $cm^{-1}$) by a dental hard tissue. The laser beam is then directed toward a surface of the dental hard tissue 1914B. In some embodiments, the laser beam is directed into an intra-oral cavity using a beam delivery system. The laser beam is often directed within the intra-oral cavity using a hand piece. In some embodiments, the laser beam is converged, using a focus optic, as it is directed toward the dental hard tissue, such that it comes to a focal region proximal the surface of the dental hard tissue. Exemplary focus optics include lenses (e.g., Zinc Selenide Plano-Convex lenses having an effective focal length of 200 mm) and parabolic mirrors. In some embodiments, the laser beam is scanned as it is directed toward the surface of the dental hard tissue by a beam scanning system. Exemplary beam scanning systems include Risley prisms, spinning polygon mirrors, voice coil scanners (e.g., Part No. MR-15-30 from Optotune of Dietikon, Switzerland), galvanometers (e.g., Lightning II 2-axis scan head from Cambridge Technology of Bedford, Massachusetts, U.S.A.), and a gantry with a translating focus optic. Scanning methods related to dental laser systems are described in U.S. Pat. No. 9,408,673 by N. Monty et al., incorporated herein by reference.

Finally, a parameter of the laser beam is controlled 1914C. Typically, the parameter of the laser beam is controlled in order to heat a portion of the surface of the dental hard tissue to a temperature within a range of 400° C. to 1300° C. Exemplary laser parameters include pulse energy, pulse duration, peak power, average power, repetition rate, wavelength, duty cycle, laser focal region size, laser focal region location, and laser focal region scan speed. During laser treatment a laser beam is generated and directed toward a surface of dental hard tissue. Typically, the laser beam is pulsed at a prescribed repetition rate and has a certain pulse duration. Alternatively, pulses can be delivered on demand, and the pulse duration can vary (for example, to control heating of the surface of the dental hard tissue). As a result of the irradiation of the surface, a temperature of the surface rises typically to within a range between 400° C. and 1300° C. momentarily (e.g., during a duration of the laser pulse) and cools back to a normal temperature range (e.g., within a range of 20° C. and 60° C.). As a result of the momentary temperature rise biological materials previously on or adhered to the surface of the dental hard tissue (e.g., pellicle, bio-film, calculus, and tartar) are at least partially removed and/or denatured. In some embodiments, this removal of biological materials substantially cleans the teeth and the laser treatment replaces other tooth cleaning procedures typically performed during a dental check-up (e.g., scaling and polishing). Additionally, as described above, heating the surface of the dental hard tissue removes impurities (e.g., carbonate) from the dental hard tissue and makes the dental hard tissue less-susceptible to acid dissolution (e.g., demineralization). In some embodiments, the laser treatment is performed after other treatments during a dental visit. For example, in some cases the dental laser treatment is performed 1914 only after one or more of removal of plaque and tartar (with one or more manual instruments), professional flossing, and power polishing (i.e., dental prophylaxis). This order of steps in some cases is considered advantageous, as the laser treatment purifies only an outer portion (e.g., 2 µm thick) of the dental enamel and some dental cleaning treatments can remove a portion of dental enamel (e.g., power polishing), potentially removing the enamel which has just been purified. After, the dental laser treatment has been performed additional steps are taken for the preventative dental treatment 1900, in accordance with one embodiment.

Next, a dental fluoride treatment is applied to at least a portion of the surface of the dental hard tissue 1916. The dental fluoride treatment dose in one embodiment has a form of a gel, a varnish, a paste, or a foam. The dental fluoride treatment dose in one embodiment comprises at least one of Sodium Fluoride, Stannous Fluoride, Titanium Tetrafluoride, Acidulated-Phosphate Fluoride, and Amine Fluoride. In one exemplary embodiment, the fluoride dose has a varnish form and is applied to a portion of a surface of the dental hard tissue using an applicator. In some embodiments, application of the dental fluoride dose 1916 is performed after the dental laser treatment. In some cases, this order is considered advantageous as plaque, pellicle, and biofilm are substantially removed from the surface of the dental hard tissue during the laser treatment.

Future verification of the machine-readable code is prevented 1918. For example, by rendering unreadable the machining readable code (e.g., overwriting a one-wire chip or RFID authentication tag). In another example, the machine-readable code is indicated as invalid (e.g., on a list or ledger). In some cases, RFID authentication tags and/or one-wire authentication chips are too expensive to use to represent a single use of the system 1800, and instead barcodes (e.g., printed on paper or film) are used to represent a coupon for one or more treatments. This drastically reduces the cost of manufacture for coupons, but also adds new difficulties to authentication.

Figure 19A:
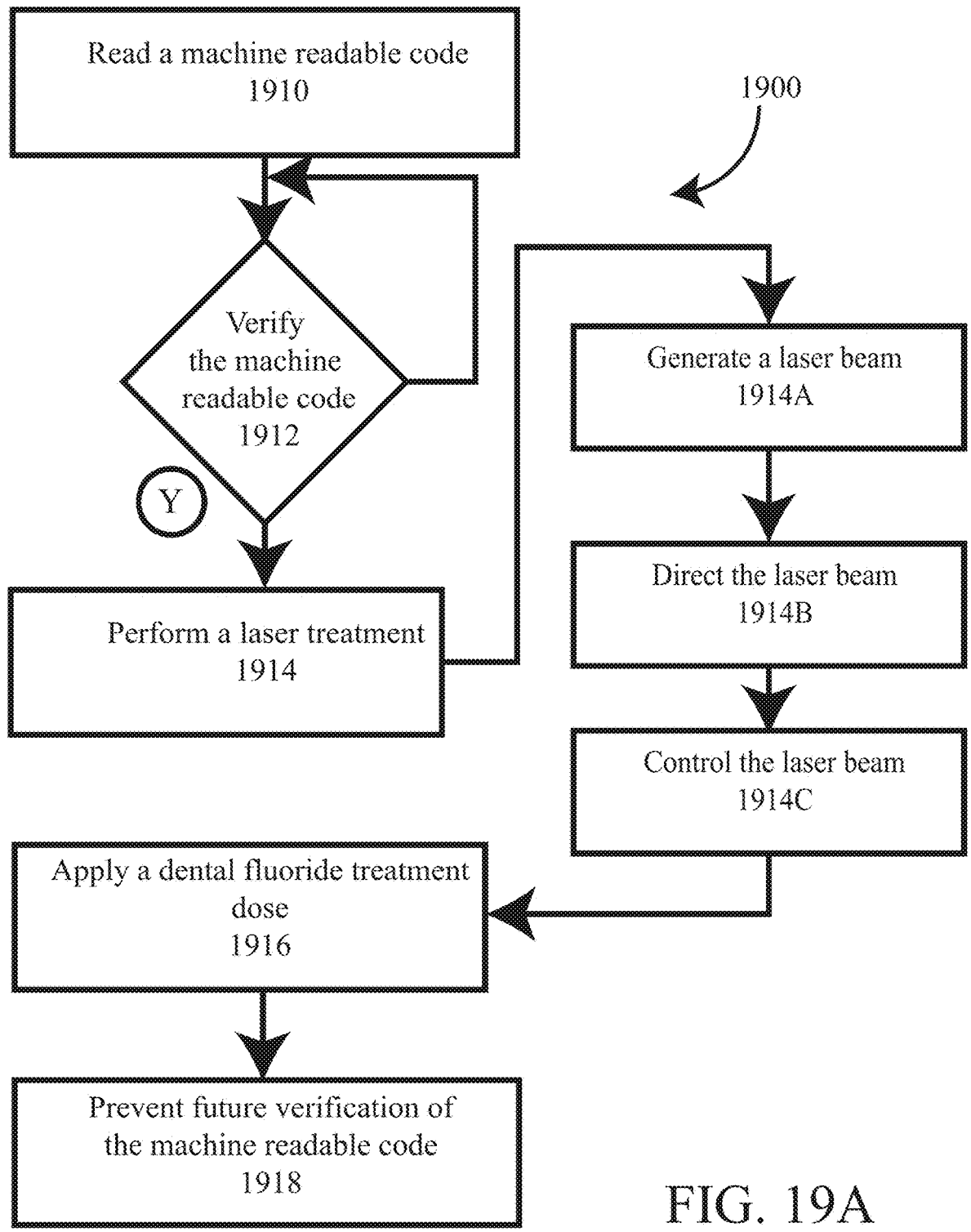
FIG. 19A illustrates a flow chart representing a method for performing a preventative dental laser treatment, in accordance with one embodiment.
Figure 19B:
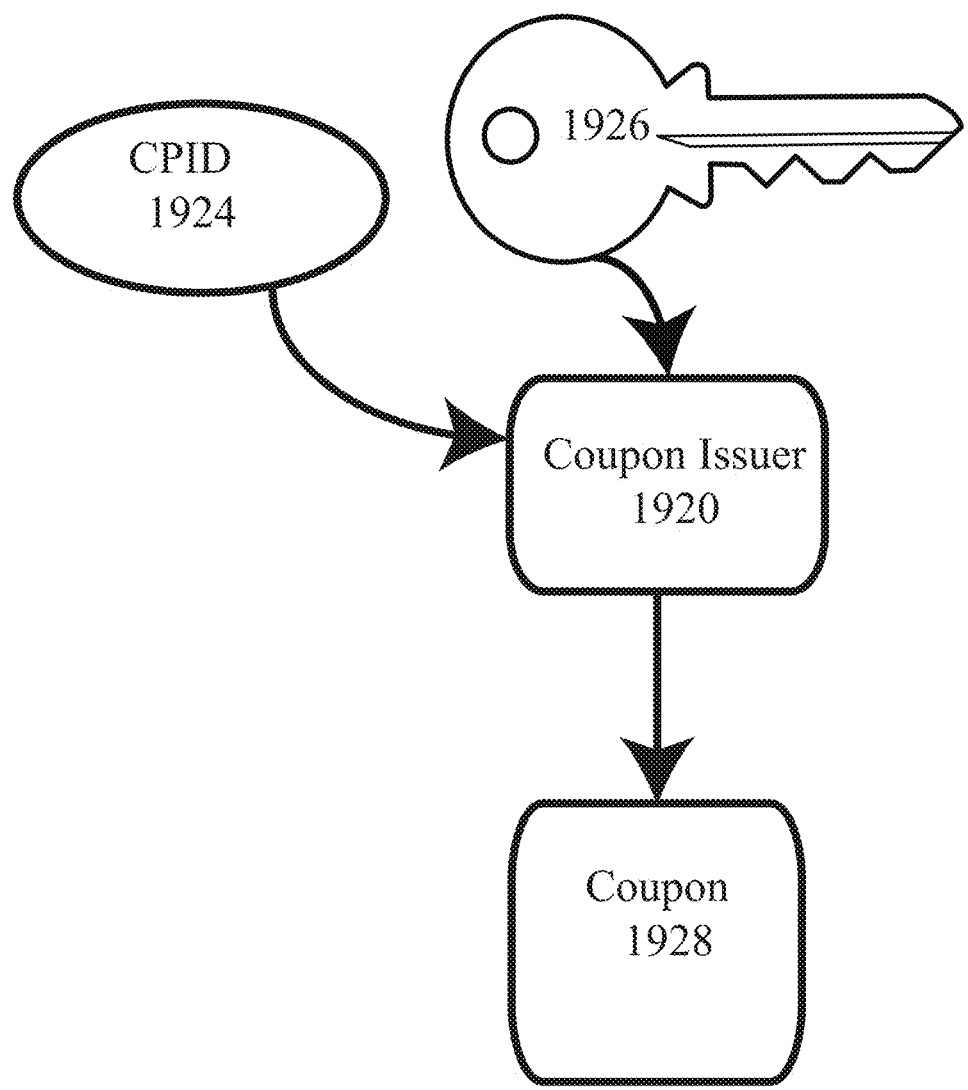
FIG. 19B illustrates a block diagram of a coupon issuance system, in accordance with one embodiment.

A number of systems and methods can be used for verification of valid coupons and rejection of non-valid coupons. A number of exemplary subsystems are described in the following paragraphs to aid in the practice of this invention. An exemplary coupon verification system and method is shown in FIG. 19B. In this case, a coupon issuer 1920 issues a coupon 1922 and generates a machine-readable code. The coupon issuer 1920 uses a coupon identification number (CPID) and an encryption key 1926 (e.g., private key) to generate a digital signature which represents a coupon 328. In an exemplary embodiment, the CPID 1924 comprises a digest and is generated, by the coupon issuer, from a message, using a cryptographic hash algorithm (e.g., SHA-3) or a pseudo-random number generating algorithm. In some embodiments, the CPID 1924 is documented and grouped by manufacturing lots, case, or package serial number. The coupon (digital signature) 1928 is then encoded into a machine-readable code (e.g., barcode, RFID, magnetic strip, a digital signature, etc.) and the machine-readable code is sequestered (e.g., packaged with a single use fluoride treatment) and ultimately distributed to a treatment system.

Figure 19C:
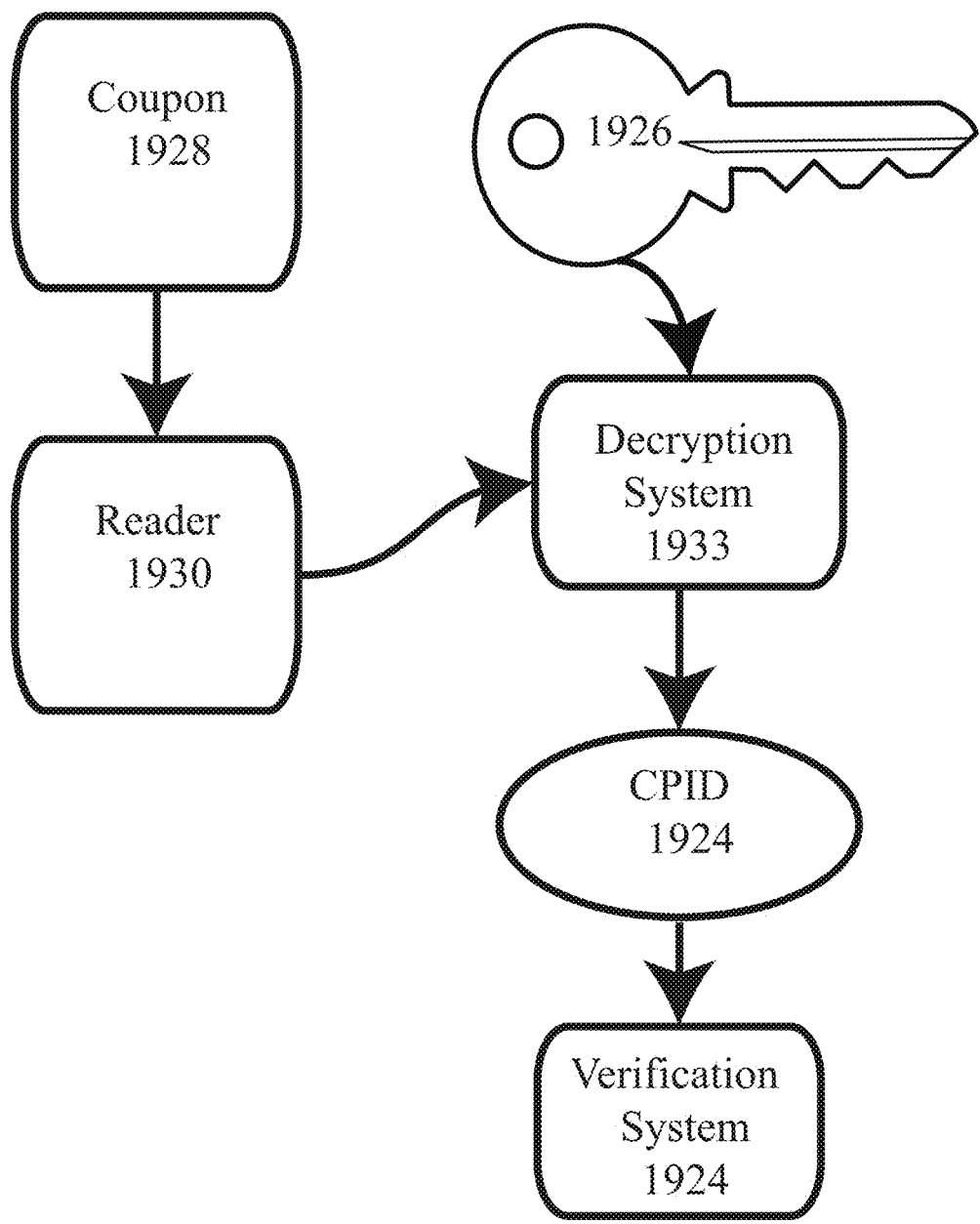
FIG. 19C illustrates a block diagram of a coupon decryption system, in accordance with one embodiment.

An exemplary coupon reading and decrypting system is described with reference to FIG. 19C. The machine-readable code 1922 is ultimately read by a reader 1930. An encryption key 1932 (e.g., public key or symmetric key) is used to decrypt the machine-readable code (for example, with a decryption system 1933) yielding the CPID 1924. The CPID 1924 can then be verified. For example, in a simple case, the CPID 1924 is generated using an algorithm (e.g., SHA-2 or SHA-3) which is duplicated on the treatment system; and, the verification system 1934 verifies a veracity of the CPID 1924 by an accordance between the CPID and the algorithm. In some embodiments, the verification system 1934 verifies that the CPID 1924 is valid using one or more authorities.

Figure 19D:
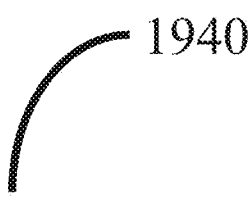
FIG. 19D represents a coupon authority system, in accordance with one embodiment.

A coupon authority 1940 is described in reference to FIG. 19D. In the simplest case the coupon authority only tracks coupon identification numbers 1924 and coupon validity 1942. In one embodiment, the coupon authority 1940 also tracks additional information 1950. The coupon authority 1940 in some cases is local to the verification system 1836 within the treatment system 1800. Alternatively, the coupon authority 1940 is remote. The coupon authority in some cases is decentralized and a local coupon authority 1940 exists within the treatment system. In some cases, the coupon authority only tracks spent (non-valid) coupons. In one embodiment, verification of the coupon includes querying the coupon authority 1940.

In another exemplary embodiment, coupons are distributed electronically using a system like bitcoin. In this system, a stock of coupons possessed by each individual treatment system is tracked by a system of decentralized ledgers (e.g., blockchain). In this case, verification of a coupon includes transferring the coupon (for example, to the distributor, to the coupon issuer, to a specified coupon collector, or to a void) and verifying that the transfer was recorded in one or more ledgers. In some cases, the transfer includes broadcasting a digital signature (for example, encrypted by a private key associated with the treatment system 1800) that includes a message comprising the transfer. In some cases, the message also includes additional information. Exemplary additional information includes, a date and time of treatment, a total energy consumed by laser system (lifetime), a total energy generated by laser system (lifetime), data related to the machine-readable code, a total number of treatments performed by the laser system, etc. In some certain exemplary embodiments, the coupons are digital in form and are distributed electronically.

Figure 20A:
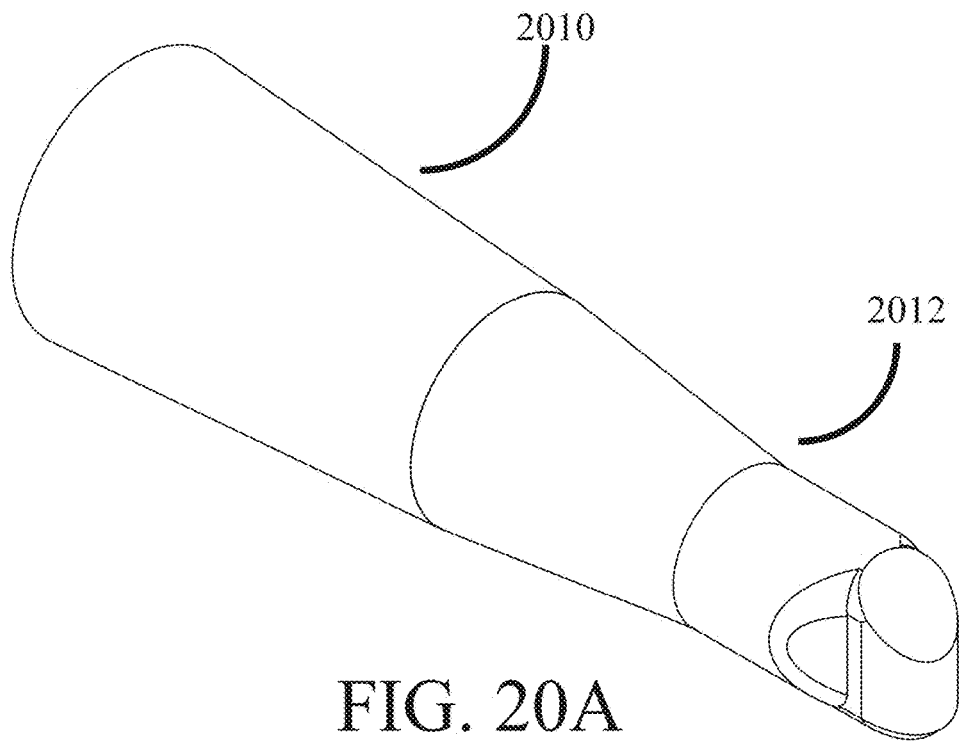
FIG. 20A illustrates a consumable dental laser attachment, in accordance with one embodiment.
Figure 20B:
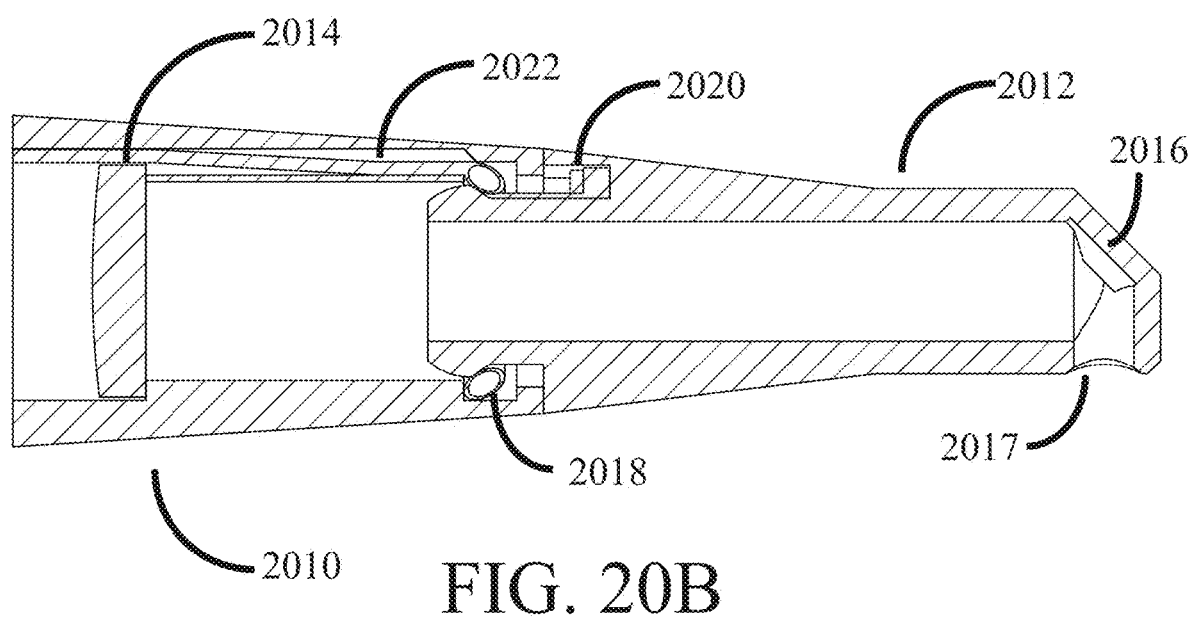
FIG. 20B illustrates a cross-sectional view of a consumable dental laser attachment, in accordance with one embodiment.

According to one embodiment, a machine-readable code 1714 is included within a consumable (e.g., single-use) hand piece attachment. FIG. 20A illustrates a view of a dental laser hand piece 2010 with an attachable tip 2012 attached. In some cases, the attachment 2012 is provided within a hermetically sealed package with a single-use fluoride dose. The attachment 2012 and hand piece 2010 of FIG. 20A is shown in a cross-sectional view in FIG. 20B. Within the hand piece 2010 a focus optic 2014 is located to converge a laser beam. Opposite the focus optic 2014, a reflector 2016 is positioned within the attachment 2012. The reflector 2016 has a high reflectivity (e.g., at least as great as 50%) at a wavelength of the laser beam. The reflector 2016 is positioned to reflect the converging laser beam out of an aperture 417 within the attachment 2012. In some cases, the attachment is made from an ejection molded polymer. The reflector 2016, in some embodiments, is coated on a surface of the attachment 2012. Alternatively, the reflector 2016 comprises a separate substrate from the attachment 2016. Exemplary coatings for the reflector 2016 include broadband coatings (e.g., silver, protected silver, and gold) and dielectric coatings. The attachment 2012, in certain exemplary embodiments shown in FIGS. 20A-B, is attached to the hand piece 2010 using a canted coil spring 2018 (e.g., Bal-Seal of Foothill Ranch, California U.S.A.). The canted coil spring 2018, in some cases can also provide an electrical connection between a one-wire authentication chip 2020 storing the machine-readable code and an electrical connection in the hand piece 2022, which is ultimately connected to a processor within the laser treatment system. An exemplary one-wire authentication chip is Part No. DS28C50 from Maxim Integrated of San Jose, California, U.S.A. The attachment 2012 shown in FIGS. 20A-B helps direct the laser beam intra-orally by reflecting the laser beam. In other embodiments, a consumable attachment is provided that does not reflect the laser beam.

Figure 21A:
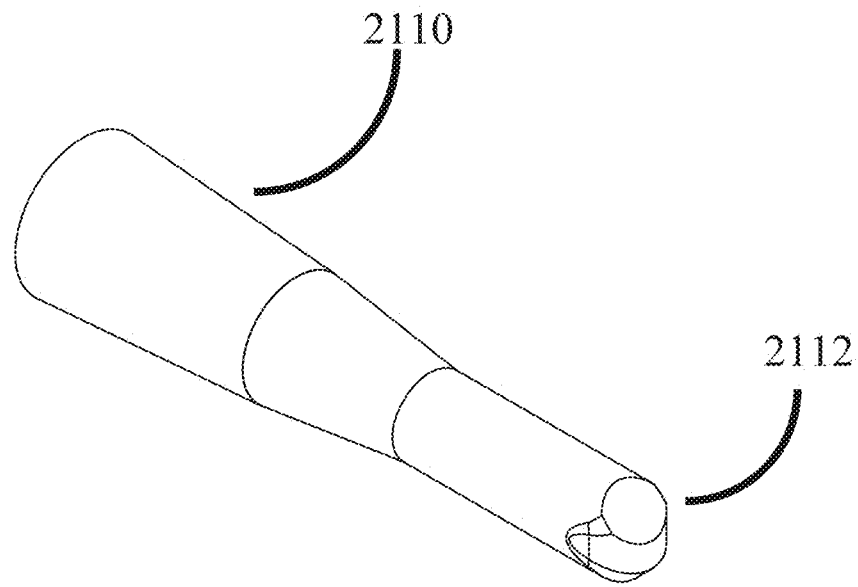
FIG. 21A illustrates a consumable dental laser attachment, in accordance with one embodiment.
Figure 21B:
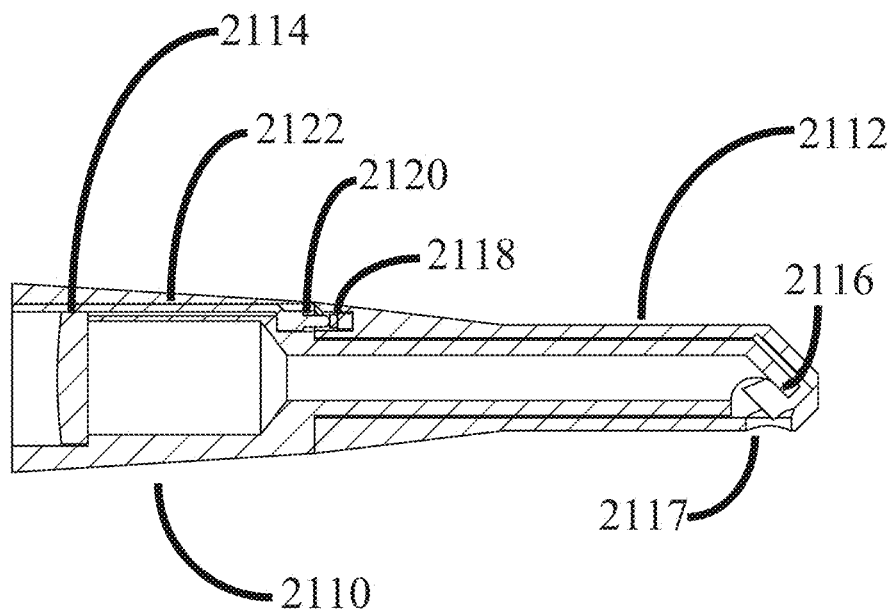
FIG. 21B illustrates a cross-sectional view a consumable dental laser attachment, in accordance with one embodiment.

Referring now to FIG. 21A a hand piece 2110 is shown with a consumable sheath attached 2112, in accordance with one embodiment. The consumable sheath 2112 allows for intra-oral use without need for sterilization of the hand piece 2110 in between patients. This is because only the sheath 2112 (during normal use) comes into contact with a patient. A new sheath therefore is used with each patient (and, therefore each new treatment). FIG. 21B illustrates a cross-sectional view of the hand piece 2110 and the sheath 2112 of FIG. 21A. A focus optic 2114 is positioned within the hand piece 2110. The focus optic 2114 is configured to converge a laser beam. Opposite and down-beam from the focus optic 2114 is a reflector 2116. Unlike the embodiment illustrated in FIGS. 20A-B, the reflector 2116 is not a part of the consumable attachment (the sheath) 2112. Instead, the reflector 2116 is an integrated component of the hand piece 2110. The reflector 2116 in some cases is a separate part from the rest of the hand piece 2110 and is therefore removable for maintenance. However, the reflector 2116 in this case is not intended for removal with each treatment. The reflector is configured to reflect the converging laser beam out of an aperture 2117 within the sheath 2112. In some embodiments, the sheath 2112 is attached to the hand piece in FIG. 21B by a snap feature (not shown). Alternative attachment of the sheath and the consumable attachment are also envisioned, for example fasteners, threads, clamps, magnets, and O-rings. The sheath 2116, in some embodiments, comprises a one-wire authentication chip 2118. The chip includes the machine-readable code. The hand piece 2110 comprises a pogo pin 2120 which is configured to make an electrical contact between the chip 2118 and an electrical connection 2122 within the hand piece 2110. The electrical connection within the hand piece communicates with a 5 processor in the laser treatment system, which verifies the machine-readable code. In another exemplary embodiment, the sheath comprises the machine-readable code in a different medium, for example a barcode, a 2D barcode, or an RFID tag.

To aid in practice of the claimed invention and parameter selection a table is provided below with exemplary ranges and nominal values for relevant parameters.

| Parameter | Min. | Max. | Nom. |
| --- | --- | --- | --- |
| Repetition Rate | 1 Hz | 10 KHz | 1 KHz |
| Pulse Energy | 1 µJ | 1 J | 10 mJ |
| Focal Region Width | 1 µm | 10 mm | 1 mm |
| Fluence | 0.01 J/cm$^2$ | 1 MJ/cm$^2$ | 1 J/cm$^2$ |
| Wavelength | 200-500 nm | 4000-12000 nm | 10.6 µm |
| Numerical Aperture (NA) | 0.00001 | 0.5 | 0.01 |
| Focal length | 10 mm | 1000 mm | 200 mm |
| Average Power | 1 mW | 100 W | 1 W |
| Peak Power | 50 mW | 5000 W | 500 W |
| Scan Speed | 0.001 mm/S | 10 mm/S | 100,000 mm/S |
| Scan Location Spacing | 0 | 0.5 x Focal Region Width | 10x Focal Region Width |
| Machine Readable Code Mediums | | Barcode, 2D Barcode, RFID Tag, Authentication Chip (e.g., One-Wire), Digital, Software Token (e.g., Google Authenticator), Paper Token (e.g., Transaction Authorization Number [TAN]), a consumable intra-oral component (e.g., hand piece attachment), and a film. | |
| Machine Readable Code Contents | | One Time Password (OTP), Hash Message Authentication Code, Digest, Transaction Authorization Number (TAN), are Encoded; are Encrypted; are Obfuscated (i.e., identification of valid coupons is held in secret); and, a digital signature. | |
| Fluoride Treatment Ingredients | | Sodium Fluoride, Stannous Fluoride, Titanium Tetrafluoride, Acidulated-Phosphate Fluoride, and Amine Fluoride | |

Figure 22:
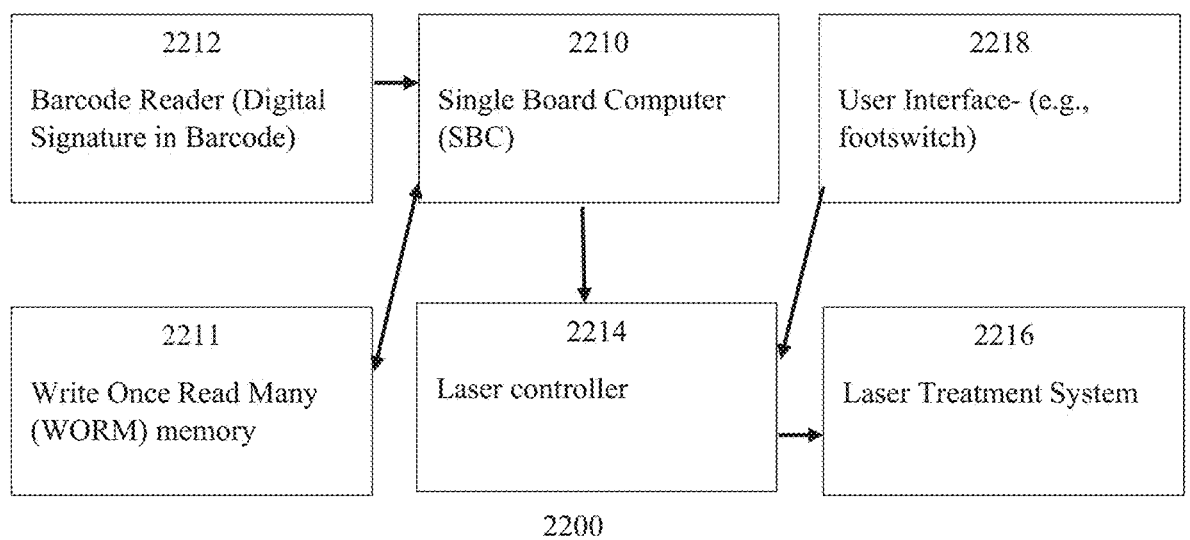
FIG. 22 illustrates a block diagram of a system for authenticating a laser treatment coupon, in accordance with one embodiment.

FIG. 22 illustrates a block diagram 2200 of a hardware configuration according to a certain exemplary embodiment. The hardware comprises a single board computer (SBC) 2210 (e.g., RaspberryPi Compute Module 4 Lite configured with a quad-core ARM Cortex-A72 processor). The SBC 2210 in some versions runs a Linux operating system. Software for the SBC 2210, including the operating system, in some cases is stored on an external write once read many (WORM) memory 2211 (e.g., a Flexxon 32 GB microSD WORM). The WORM 2211 storage allows data to be stored memory without risk of erasure. In some embodiments, a barcode reader 2212 is connected to the SBC and is configured to read a barcode, for example a high capacity 2D (HC2D) barcode. In some exemplary versions, the barcode reader 2212 comprises a digital camera and illuminator that together capture an image of a barcode. In some versions, the camera and illuminator are triggered to capture by a user interface button, which is hardwired to a GPIO digital input of the SBC 2210. An exemplary camera is a SONY IMX219 sensor that may be connected to the SBC 2210 by way of a dedicated standard CSI interface. The SBC 2210 communicates to a laser controller 2214, for example a HALaser E1701A. In some embodiments, the SBC communicates with the laser controller 2214 by way of an ethernet connection. The laser controller 2214 directly controls a laser treatment system 2216 and requisite treatment parameters for successful treatment. A user interface 2218, for example a footswitch, is also communicative with the laser controller 2216, and allows the clinician to perform a laser treatment.

The hardware configuration described in the block diagram 2200 above can be used, in certain exemplary embodiments, to (1) read a coupon; (2) decode and validate a coupon; and, (3) perform a preventive laser treatment. First, (1) a coupon is read. In certain cases, the coupon will comprise a 2D barcode, which is embellished upon a consumable component and reading the barcode will include use of a specialized barcode reader hardware 2212 located inside the device. Barcode reading hardware will, in some cases, include a camera and an illuminator. A high capacity 2-dimensional (2D) (HC2D) barcode (e.g., QR Code or similar) can be used to maximize the amount of information contained within the barcode. Once the coupon is read, it is time to (2) decode and validate the coupon. Each individual coupon must be used only once and therefore, in some versions, earlier uses of previous coupons are recorded and compared with each new coupon. Additionally, the veracity and validity of each coupon must be scrutinized. In certain exemplary embodiments, each coupon comprises a digital signature. The origin of the digital signature is decrypted with a key (e.g., public key) and the authenticity (i.e., known origin and unalteredness) of the resulting decrypted message is verified, for example by a one-way HASH algorithm. Once, the message is successfully decrypted and verified by HASH algorithm, it may be assumed that the coupon is valid (i.e., it truly represents one laser treatment). In some versions, the message is then compared to an enumerated list of previous messages already used in order to prevent double spending. A write once read many (WORM) memory 2211, in some versions, is employed to store the enumerated coupon messages representing spent coupons. Once the coupon is validated and spent (e.g., the message is saved to WORM memory), a laser treatment is authorized. Then, (3) the SBC 2210 allows the user to perform the laser treatment, for example by sending laser control parameters to the laser controller board 2214, which operates the laser system during treatment. Without these laser control parameters, the laser controller board 2214 is unable to operate the laser system 2216 and no treatment may be performed.

Figure 23:
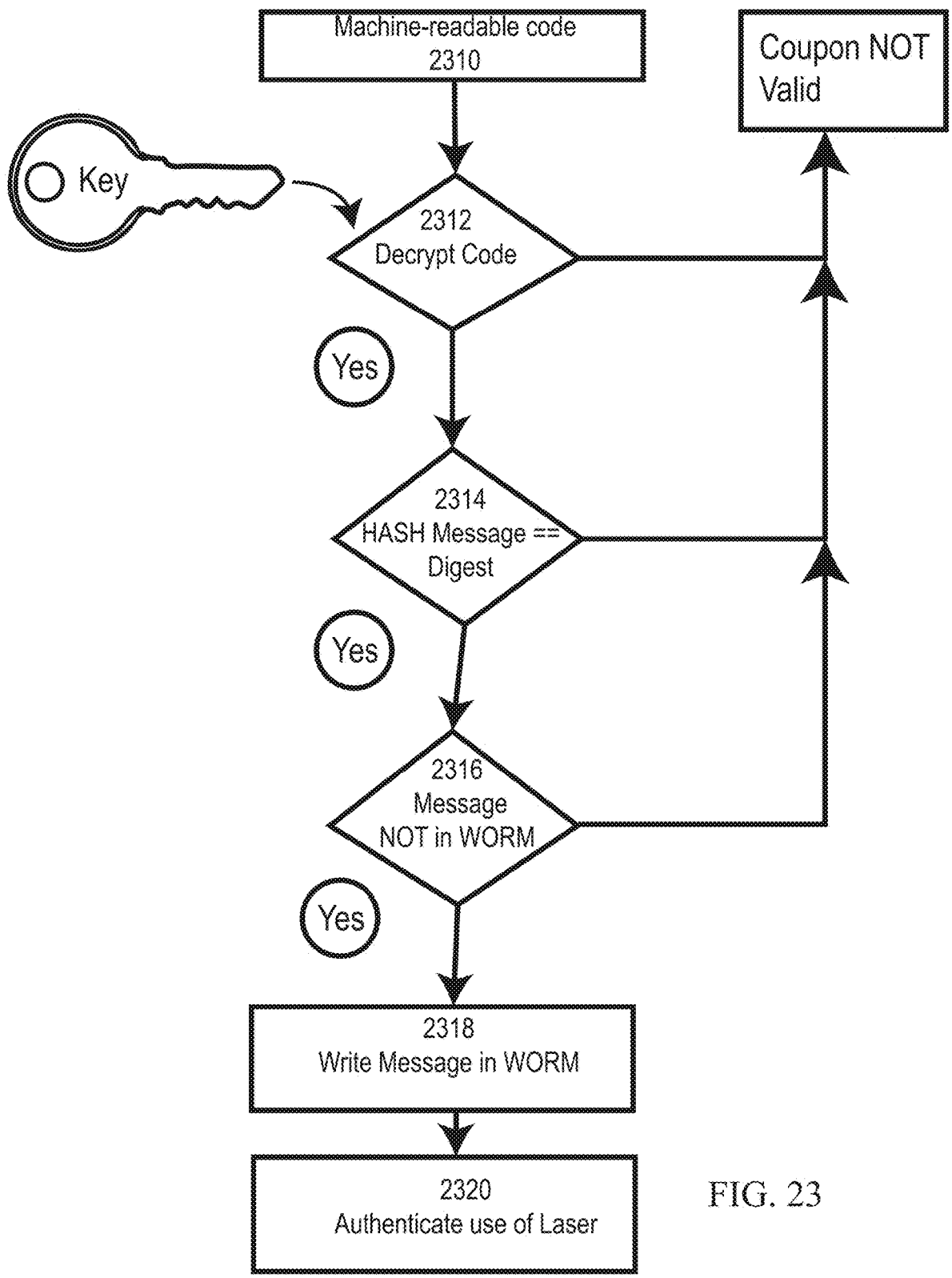
FIG. 23 illustrates a flow diagram of a method for authenticating a laser treatment coupon, in accordance with one embodiment; and, FIG. 24 illustrates a block diagram of a computer readable media comprising instructions performable by a processor, for authenticating a laser treatment coupon, in accordance with one embodiment.

FIG. 23 illustrates a flowchart 2300 describing a coupon authentication method, according to certain embodiments. First a machine-readable code is acquired 2310. For example, in some exemplary cases a barcode is scanned. The machine-readable data is then decrypted 2312, by way of a key. In some embodiments, the key is an asymmetric key (e.g., public key). By being able to decrypt the data from the barcode with a specific public key, the controller is able to ensure that the decrypted contents are from a specific source in possession of a private key. In this case, an authorized coupon issuer will generate and encrypt the coupons using a private key. The coupon will be assumed to be encrypted by the authorized coupon issuer if it is decrypted using a public key to the private key of the authorized coupon issuer. Within certain embodiments, the decrypted contents will contain a message and a digest. The message, in some cases, comprises a coupon code and the digest is the value of the message when it is run through a HASH algorithm. The decrypted message is run then through a specified HASH algorithm. The output results of the HASH algorithm are then compared to the decrypted digest 2314. If the two are equal, it is probable that the coupon has been unaltered, since it was encrypted by the authorized coupon issuer. The now validated message (e.g., coupon code) is then searched for on a write once read many (WORM) memory storage 2316. In some embodiments, the WORM is configured to store every "spent" coupon code. So, if a coupon code is located within the WORM it has already been spent. The current validated coupon code is not located on the WORM, the coupon code will be written to the WORM 2318 and the laser system will be authenticated for treatment 2320.

Figure 24:
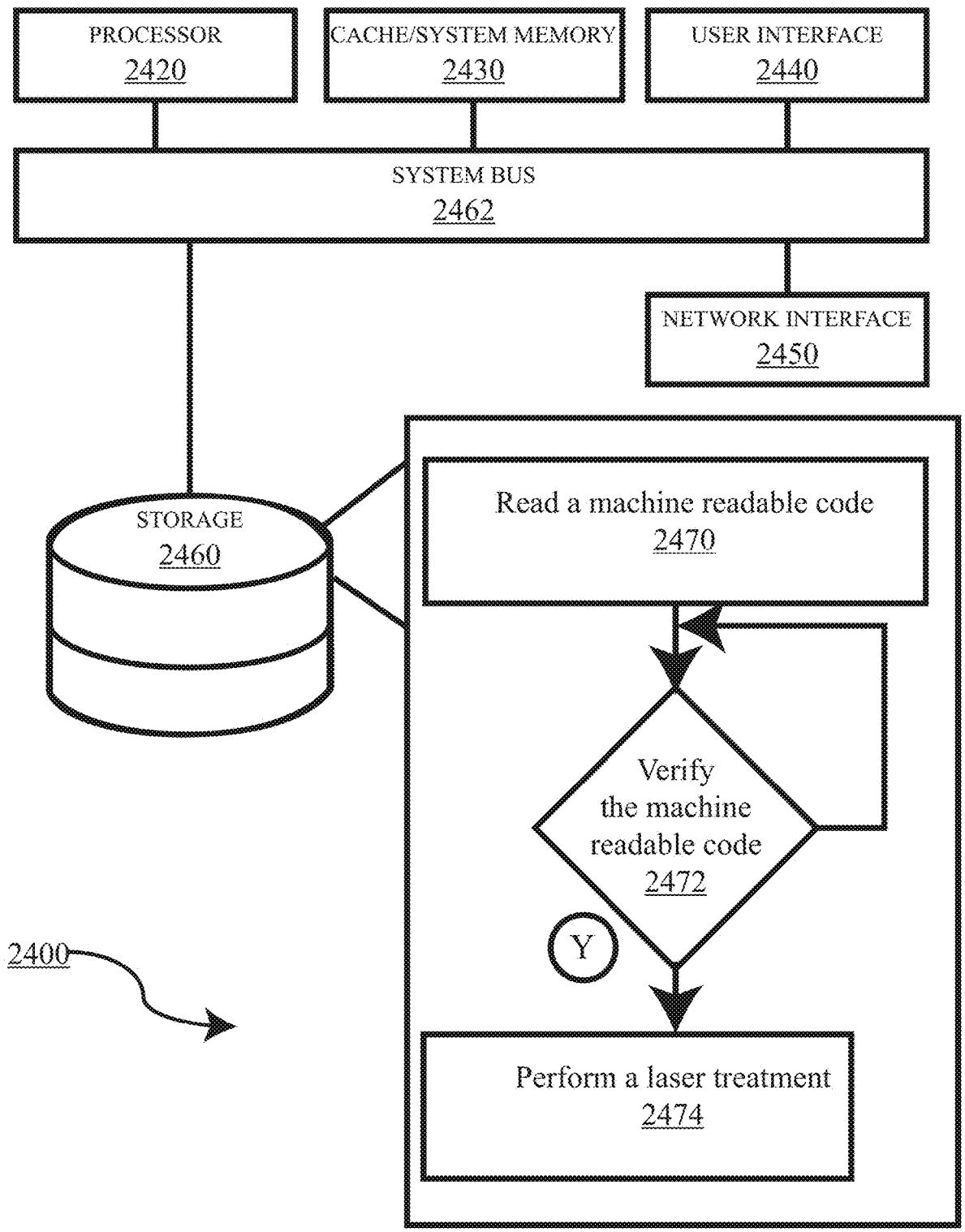

Referring now to FIG. 24, a system 2400 for authenticating a laser treatment coupon, in accordance with one embodiment, is shown. The system 2400 may include a processor 2420, a memory 2430, a user interface 2440, a network interface 2450, and storage 2460, all interconnected via one or more system buses 2462. It will be understood that FIG. 24 constitutes, in some respects, an abstraction and that the actual organization of the system 2400 and the components thereof may differ from what is illustrated.

The processor 2420 may be any hardware device capable of executing instructions stored on memory 2430 and/or in storage 2460, or otherwise any hardware device capable of processing data. As such, the processor 2420 may include a microprocessor, field programmable gate array (FPGA), an application-specific integrated circuit (ASIC), or other similar devices.

The memory 2430 may include various transient memories such as, for example L1, L2, or L3 cache or system memory. As such, the memory 2430 may include static random access memory (SRAM), dynamic RAM (DRAM), flash memory, read only memory (ROM), or other similar memory devices and configurations.

The user interface 2440 may include one or more devices for enabling communication with system operators and other personnel. For example, the user interface 2440 may include a display, a mouse, and a keyboard for receiving user commands. In some embodiments, the user interface 2440 may include a graphical user interface. The user interface 2440 may execute on a user device such as a PC, laptop, tablet, mobile device, or the like.

The network interface 2450 may include one or more devices for enabling communication with other remote devices. The network interface 2450 may also allow for downloading of updates to software applications or known "spent" coupon identifiers. For example, the network interface 2450 may include a network interface card (NIC) configured to communicate according to the Ethernet protocol. Additionally, the network interface 2450 may implement a TCP/IP stack for communication according to the TCP/IP protocols. Various alternative or additional hardware or configurations for the network interface 2450 will be apparent.

The storage 2460 may include one or more machine-readable storage media such as read-only memory (ROM), random-access memory (RAM), magnetic disk storage media, optical storage media, flash-memory devices, write once read many (WORM) memory, or similar storage media. In various embodiments, the storage 2460 may store instructions for execution by the processor 2420 or data upon which the processor 2420 may operate.

For example, the storage 2460 may include instructions to read a machine-readable code 270; verify the machine-readable code 2472; and, perform a laser treatment 2474. Instructions for performing the laser treatment may include instructions to: generating, using a laser arrangement, a laser beam; directing, using an optical arrangement, the laser beam toward a dental hard tissue; and, controlling, using a laser controller, a parameter of the laser beam in order to heat at least a portion of a surface of the dental hard tissue to a temperature above 400° Celsius.

The instructions may additionally include preventing future verification of the machine readable code. The instructions for preventing future verification of the machine-readable code may include one or more of broadcasting to a ledger, submitting to a coupon authority, destroying the machine-readable code, writing to a write once read many (WORM) memory, and overwriting the machine-readable code The instructions for verifying the machine-readable code 2472 may include one or more of querying a ledger, broadcasting to a ledger, decrypting the machine-readable code, recognizing a digest within the machine-readable code, querying a write once read many (WORM) memory, and querying a coupon authority.

The instructions may additionally include measuring a laser variable during the laser treatment. The laser variable may include one or more of a duration of laser treatment, an electrical energy delivered to the laser source during laser treatment, and a relative measure of laser energy generated by the laser source during laser treatment.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. For example, in some embodiments, fluoride treatment is omitted after laser treatment. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A system for preventative dental treatment comprising:
   a radiation source configured to generate a radiation having a wavelength in one or more of a first range between 100 and 500 nm and a second range between 8,000 and 12,000 nm;
   a diamond optic disposed to accept the radiation at a first end, internally reflect the radiation, and contact a dental hard tissue with one or more sides of the diamond optic; and, wherein the diamond optic is configured to couple at least a portion of the radiation into the dental hard tissue when placed in contact with the dental hard tissue on the one or more sides;
   a cooling system configured to cool the diamond optic, wherein the cooling system comprises:
   a fluidic pathway in fluidic communication with and sealed about the diamond optic; and
   a coolant configured to flow within the fluidic pathway and come into direct contact with the diamond optic; and
   a controller configured to control at least one parameter of the radiation to raise a temperature of a surface of the dental hard tissue to a temperature that is greater than 400° Celsius.

2. The system of claim 1, wherein the diamond optic comprises one or more of a rod, and a prism.

3. The system of claim 1, wherein the diamond optic is configured to couple at least a portion of the radiation into the dental hard tissue using one or more of attenuated total internal reflection (ATIR), frustrated total internal reflection (FTIR), and an evanescent wave.

4. The system of claim 1, wherein the diamond optic is further configured to couple substantially no portion of the radiation into a dental soft tissue when placed in contact with the dental soft tissue on the one or more sides.

5. The system of claim 1, wherein the diamond optic further comprises a diamond rod, having a diameter less than 2 mm, configured to be placed in between two teeth and in contact with an inter-proximal surface of the dental hard tissue.

6. The system of claim 1, further comprising a detector configured to detect at least one characteristic of the radiation as it exits a second end of the diamond optic.

7. The system of claim 1, further comprising a rod homogenizer disposed between the radiation source and the optic to homogenize the radiation into a flat top energy profile.

8. A method for preventative dental treatment comprising:
   generating, using a radiation source, a radiation having a wavelength in one or more of a first range between 100 and 500 nm and a second range between 8,000 and 12,000 nm;
   internally reflecting the radiation within a diamond optic disposed to accept the radiation at a first end;

contacting a dental hard tissue with one or more sides of the diamond optic;
coupling, using the diamond optic, at least a portion of the radiation into the dental hard tissue;
cooling the diamond optic, using a cooling system, wherein cooling the diamond optic comprises:
providing a fluidic pathway in fluidic communication with and sealed about the diamond optic; and
flowing, within the fluidic pathway, a coolant such that the coolant comes into direct contact with the diamond optic; and
controlling, using a controller, at least one parameter of the radiation to raise a temperature of a surface of the dental hard tissue to a temperature that is greater than 400° Celsius.

9. The method of claim 8, wherein the diamond optic comprises one or more of a rod, and a prism.

10. The method of claim 8, wherein coupling, using the diamond optic, at least a portion of the radiation into the dental hard tissue comprises one or more of attenuated total internal reflection (ATIR), frustrated total internal reflection (FTIR), and an evanescent wave.

11. The method of claim 8, further comprising:
contacting a dental soft tissue with the one or more sides of the diamond optic; and,
coupling, using the diamond optic, substantially no portion of the radiation into the dental soft tissue.

12. The method of claim 8, further comprising:
placing, using the diamond optic, having a diameter less than 2 mm, in between two teeth; and
contacting, using the diamond optic, an inter-proximal surface of the dental hard tissue.

13. The method of claim 8, further comprising detecting, using a detector, at least one characteristic of the radiation as it exits a second end of the diamond optic.

14. The method of claim 8, further comprising homogenizing the radiation into a flat top energy profile, using a rod homogenizer.

* * * * *